United States Patent
Younes

(10) Patent No.: US 9,763,589 B2
(45) Date of Patent: Sep. 19, 2017

(54) METHOD AND SOFTWARE TO DETERMINE PROBABILITY OF SLEEP/WAKE STATES AND QUALITY OF SLEEP AND WAKEFULNESS FROM AN ELECTROENCEPHALOGRAM

(71) Applicant: YRT Limited, Winnipeg, Manitoba (CA)

(72) Inventor: Magdy Younes, Winnepeg (CA)

(73) Assignee: YRT Limited (CA)

(*) Notice: Subject to any disclaimer, the term of this patent is extended or adjusted under 35 U.S.C. 154(b) by 0 days.

(21) Appl. No.: 14/426,533

(22) PCT Filed: Sep. 12, 2013

(86) PCT No.: PCT/CA2013/000769
§ 371 (c)(1),
(2) Date: Mar. 6, 2015

(87) PCT Pub. No.: WO2014/040167
PCT Pub. Date: Mar. 20, 2014

(65) Prior Publication Data
US 2015/0238103 A1    Aug. 27, 2015

Related U.S. Application Data

(60) Provisional application No. 61/700,615, filed on Sep. 13, 2012.

(51) Int. Cl.
*A61B 5/04* (2006.01)
*A61B 5/0476* (2006.01)
(Continued)

(52) U.S. Cl.
CPC ........ *A61B 5/04014* (2013.01); *A61B 5/0205* (2013.01); *A61B 5/0476* (2013.01);
(Continued)

(58) Field of Classification Search
CPC ..... A61B 5/04014; A61B 5/11; A61B 5/4818; A61B 5/725; A61B 5/4809; A61B 5/4812;
(Continued)

(56) References Cited

U.S. PATENT DOCUMENTS

2007/0016095 A1*  1/2007  Low .............. A61B 5/048
                                                        600/544

FOREIGN PATENT DOCUMENTS

WO    2004026133    4/2004

OTHER PUBLICATIONS

Dressler et al., "Awareness and the EEG Power Spectrum: Analysis of Frequencies" British Journal of Anaesthesia. vol. 93, No. 6, 2004, pp. 806-809.
(Continued)

*Primary Examiner* — Rex R Holmes
(74) *Attorney, Agent, or Firm* — Tarolli, Sundheim, Covell & Tummino LLP

(57) ABSTRACT

Method and software are provided to format a probability index that reflects where an electroencephalogram (EEG) pattern lies within the spectrum of wakefulness to deep sleep, which employs a computer/microprocessor that performs frequency domain analysis of one or more discrete sections (Bins) of the EEG to determine the EEG power at specified frequencies, optionally calculates the total power over specified frequency ranges, assigns a rank to the power at each frequency, or frequency range, assigns a code to the Bin that reflects the ranking of the different frequencies or frequency ranges, and determines an index that reflects where said EEG pattern within said Bin(s) lies within the spectrum of wakefulness to deep sleep by use of a reference source, such as a look-up table or other suitable decoding instrument. The reference source is obtained by calculating
(Continued)

the probability of Bins with different codes occurring in epochs scored as awake or asleep in reference files scored by one or more expert technologists or by an automatic scoring software.

15 Claims, 55 Drawing Sheets

(51) Int. Cl.
  *A61B 5/00*   (2006.01)
  *A61B 5/0205*  (2006.01)
  *A61B 5/11*   (2006.01)
  *G06F 19/00*  (2011.01)
  *A61B 5/024*  (2006.01)
  *A61B 5/08*   (2006.01)

(52) U.S. Cl.
  CPC .............. *A61B 5/11* (2013.01); *A61B 5/4809* (2013.01); *A61B 5/4812* (2013.01); *A61B 5/4815* (2013.01); *A61B 5/4818* (2013.01); *A61B 5/725* (2013.01); *A61B 5/7264* (2013.01); *A61B 5/02405* (2013.01); *A61B 5/0826* (2013.01); *G06F 19/3431* (2013.01)

(58) Field of Classification Search
  CPC ... A61B 5/7264; A61B 5/0205; A61B 5/4815; A61B 5/0476; A61B 5/0826; A61B 5/02405; G06F 19/3431
  See application file for complete search history.

(56) References Cited

OTHER PUBLICATIONS

Albertario, Claude L., et al. "Comparison of a frequency-based analysis of electroencephalograms (Z-ratio) and visual scoring on the multiple sleep latency test." Sleep 18.10 (1995): 836-843.

Extended European Search Report for corresponding EP 13 83 7396, dated May 13, 2016, pp. 1-6.

Office Action for corresponding Chinese Appl. No. 201380047826.7, dated Jul. 6, 2016, pp. 1-10.

\* cited by examiner

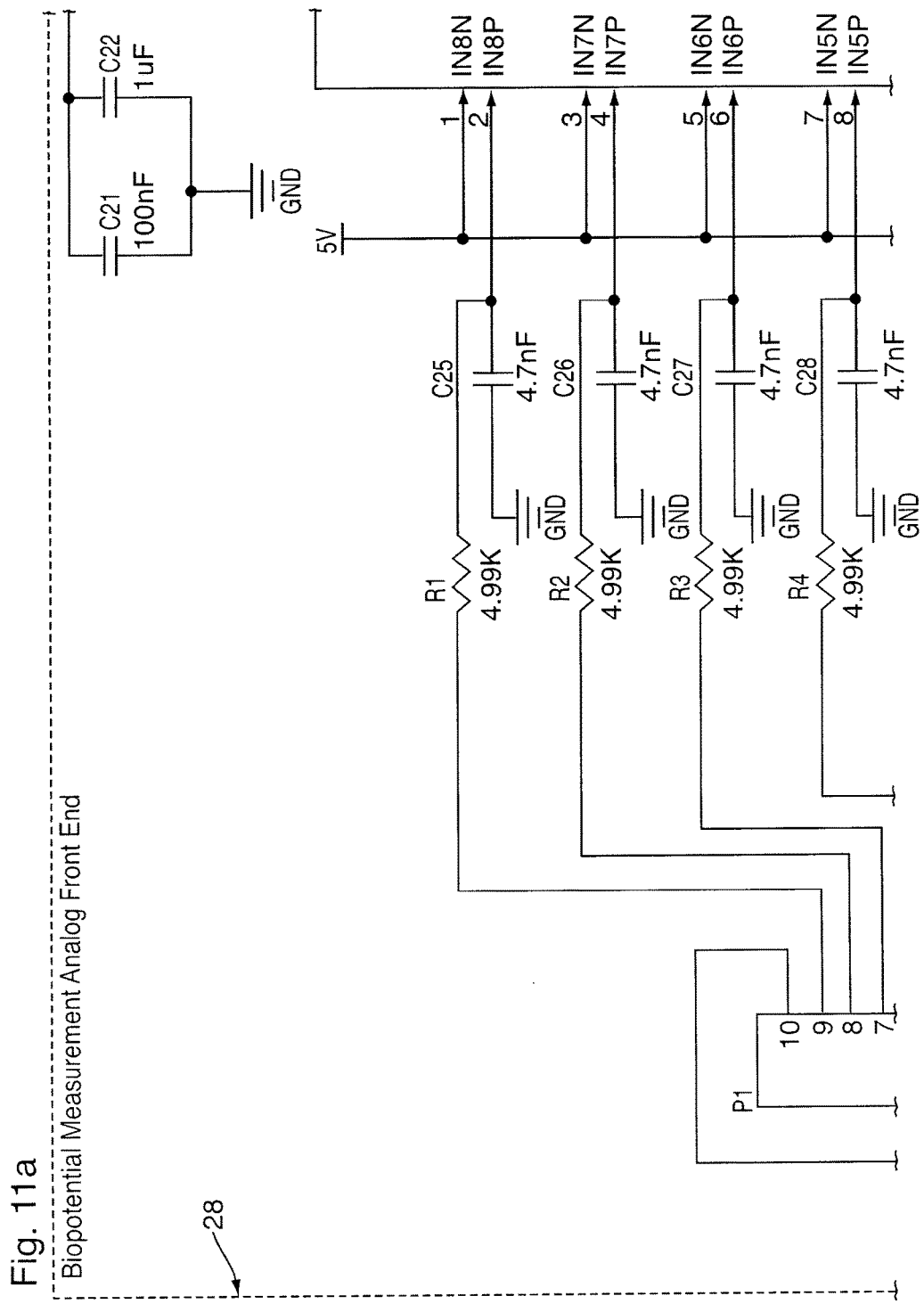
Fig. 11a Biopotential Measurement Analog Front End

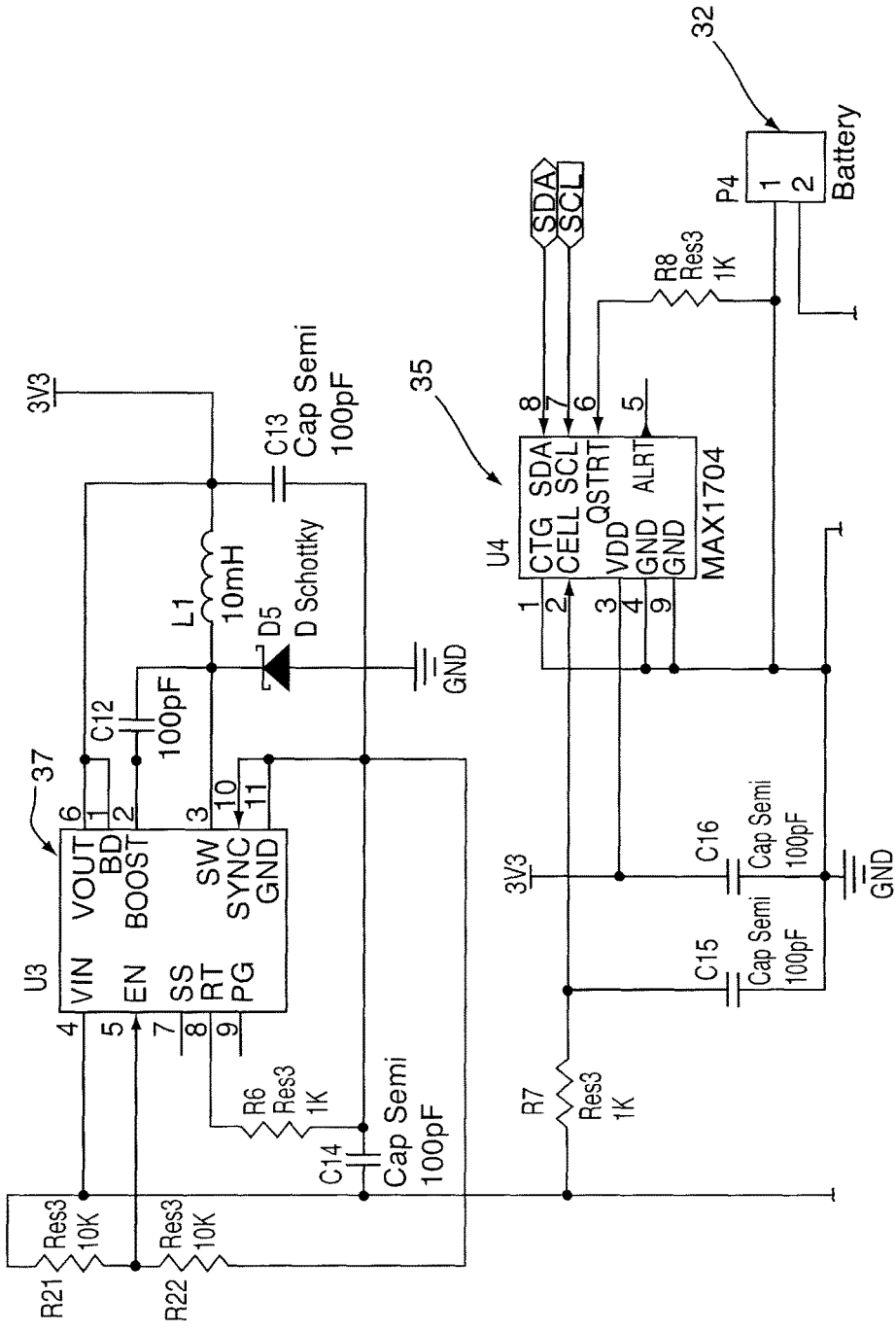
Fig. 13a Power System-Battery Charge and Measurement

Fig. 14a

|     | 0    | 1    | 2    | 3    | 4    | 5    | 6    | 7    | 8    | 9    | 10   | 11   | 12   |
| --- | ---- | ---- | ---- | ---- | ---- | ---- | ---- | ---- | ---- | ---- | ---- | ---- | ---- |
| 0   | 0.92 | 1.80 | 1.88 | 1.95 | 2.05 | 2.13 | 2.27 | 2.39 | 2.50 | 2.50 | 1.33 | 1.72 | 2.02 |
| 20  | 1.81 | 2.21 | 2.28 | 2.24 | 2.32 | 2.24 | 2.30 | 2.39 | 2.46 | 2.50 | 2.30 | 2.30 | 2.31 |
| 40  | 1.98 | 2.38 | 2.40 | 2.47 | 2.44 | 2.42 | 2.45 | 2.41 | 2.46 | 2.49 | 2.50 | 2.39 | 2.46 |
| 60  | 2.30 | 2.27 | 2.50 | 2.49 | 2.49 | 2.47 | 2.49 | 2.49 | 2.48 | 2.49 | 2.30 | 2.37 | 2.41 |
| 80  | 2.30 | 2.50 | 2.43 | 2.44 | 2.50 | 2.49 | 2.49 | 2.50 | 2.50 | 2.50 | 2.30 | 2.30 | 2.30 |
| 100 | 0.26 | 0.52 | 0.78 | 0.78 | 1.03 | 1.38 | 1.64 | 1.93 | 2.20 | 2.50 | 0.48 | 0.80 | 0.78 |
| 120 | 1.10 | 1.11 | 1.34 | 1.51 | 1.68 | 1.52 | 1.85 | 2.13 | 2.32 | 2.50 | 1.50 | 1.60 | 1.71 |
| 140 | 1.60 | 1.60 | 1.90 | 2.24 | 2.28 | 2.27 | 2.25 | 2.24 | 2.30 | 2.47 | 2.00 | 2.00 | 2.16 |
| 160 | 2.20 | 2.20 | 2.32 | 2.39 | 2.42 | 2.43 | 2.33 | 2.44 | 2.48 | 2.50 | 2.30 | 2.30 | 2.50 |
| 180 | 2.50 | 2.50 | 2.50 | 2.50 | 2.47 | 2.50 | 2.49 | 2.49 | 2.48 | 2.50 | 2.50 | 2.50 | 2.50 |
| 200 | 0.19 | 0.28 | 0.35 | 0.66 | 0.63 | 0.46 | 0.80 | 1.60 | 2.00 | 2.20 | 0.24 | 0.28 | 0.37 |
| 220 | 0.50 | 0.56 | 0.81 | 1.00 | 1.15 | 1.30 | 1.45 | 1.60 | 2.15 | 2.30 | 0.80 | 0.80 | 0.80 |
| 240 | 1.28 | 1.40 | 1.52 | 1.64 | 2.04 | 1.97 | 1.81 | 2.00 | 2.31 | 2.50 | 1.55 | 1.65 | 1.75 |
| 260 | 1.82 | 1.90 | 1.98 | 2.08 | 2.34 | 2.29 | 2.23 | 2.42 | 2.47 | 2.47 | 2.09 | 2.15 | 2.21 |
| 280 | 2.36 | 2.40 | 2.44 | 2.37 | 2.44 | 2.46 | 2.46 | 2.44 | 2.47 | 2.50 | 2.50 | 2.50 | 2.50 |
| 300 | 0.16 | 0.30 | 0.15 | 0.31 | 0.16 | 0.80 | 1.00 | 1.19 | 1.38 | 1.57 | 0.14 | 0.25 | 0.32 |
| 320 | 0.12 | 0.38 | 0.40 | 0.80 | 0.80 | 1.00 | 0.80 | 1.50 | 2.34 | 1.82 | 0.80 | 0.80 | 0.95 |
| 340 | 0.80 | 0.23 | 1.19 | 1.31 | 1.44 | 1.56 | 2.10 | 1.80 | 2.18 | 2.06 | 1.20 | 1.31 | 1.42 |
| 360 | 1.47 | 1.57 | 1.66 | 1.75 | 2.20 | 2.34 | 2.31 | 2.03 | 2.28 | 2.50 | 1.74 | 1.82 | 1.89 |
| 380 | 2.01 | 2.07 | 2.13 | 2.26 | 2.50 | 2.50 | 2.33 | 2.40 | 2.47 | 2.50 | 2.28 | 2.32 | 2.37 |
| 400 | 0.08 | 0.07 | 0.10 | 0.00 | 0.80 | 0.80 | 0.80 | 0.80 | 1.03 | 1.22 | 0.25 | 0.00 | 0.30 |
| 420 | 0.00 | 0.00 | 0.18 | 0.80 | 0.69 | 0.85 | 1.01 | 1.17 | 1.33 | 1.49 | 0.80 | 0.00 | 0.80 |
| 440 | 0.80 | 0.80 | 0.80 | 0.80 | 1.11 | 1.24 | 1.37 | 1.50 | 1.63 | 1.76 | 0.80 | 0.80 | 1.09 |
| 460 | 1.12 | 1.22 | 1.33 | 1.43 | 1.53 | 2.50 | 2.29 | 2.27 | 1.93 | 2.03 | 1.39 | 1.48 | 1.56 |
| 480 | 1.66 | 1.73 | 1.80 | 1.87 | 1.94 | 2.41 | 2.31 | 2.42 | 2.50 | 2.50 | 1.93 | 1.98 | 2.04 |
| 500 | 0.00 | 0.80 | 0.80 | 0.80 | 0.80 | 0.80 | 0.80 | 0.80 | 0.80 | 0.80 | 0.80 | 0.00 | 0.80 |

Fig. 14a'

| | | | | | | | | | | | | | | |
|---|---|---|---|---|---|---|---|---|---|---|---|---|---|---|
| 520 | 0.80 | 0.80 | 0.80 | 0.80 | 0.23 | 0.80 | 0.80 | 0.80 | 1.00 | 0.80 | 0.80 | 0.80 | 0.80 |
| 540 | 0.80 | 0.80 | 0.80 | 0.80 | 0.80 | 0.80 | 1.04 | 1.17 | 1.31 | 1.44 | 1.04 | 1.14 | 1.23 |
| 560 | 0.80 | 0.80 | 1.09 | 1.30 | 1.20 | 1.30 | 1.41 | 1.51 | 1.62 | 1.73 | 1.58 | 1.64 | 1.71 |
| 580 | 1.31 | 1.39 | 1.47 | 1.54 | 1.62 | 1.70 | 2.50 | 2.50 | 2.50 | 2.50 | 0.80 | 0.80 | 0.80 |
| 600 | 0.80 | 0.80 | 0.80 | 0.80 | 0.80 | 0.80 | 0.80 | 0.80 | 0.80 | 0.80 | 0.80 | 0.80 | 0.80 |
| 620 | 0.80 | 0.80 | 0.80 | 0.80 | 0.80 | 0.80 | 0.80 | 0.80 | 0.80 | 0.80 | 0.80 | 0.80 | 0.80 |
| 640 | 0.80 | 0.80 | 0.80 | 0.80 | 0.80 | 0.80 | 1.08 | 1.19 | 1.30 | 1.11 | 0.80 | 0.80 | 0.80 |
| 660 | 0.80 | 1.05 | 1.13 | 1.21 | 1.29 | 1.37 | 1.46 | 1.54 | 1.62 | 1.41 | 1.23 | 1.30 | 1.37 |
| 680 | 0.80 | 0.80 | 0.80 | 0.80 | 0.80 | 0.80 | 0.80 | 0.80 | 0.80 | 1.70 | 0.80 | 0.80 | 0.80 |
| 700 | 0.80 | 0.80 | 0.80 | 0.80 | 0.80 | 0.80 | 0.80 | 0.80 | 0.80 | 0.80 | 0.80 | 0.80 | 0.80 |
| 720 | 0.80 | 0.80 | 0.80 | 0.80 | 0.80 | 0.80 | 0.80 | 0.80 | 0.80 | 0.80 | 0.80 | 0.80 | 0.80 |
| 740 | 0.80 | 0.80 | 0.80 | 0.80 | 0.80 | 1.04 | 1.13 | 1.22 | 1.30 | 1.09 | 0.80 | 0.80 | 0.80 |
| 760 | 0.80 | 0.80 | 0.80 | 0.80 | 0.80 | 0.80 | 0.80 | 0.80 | 0.80 | 1.39 | 0.80 | 0.80 | 0.80 |
| 780 | 0.80 | 0.80 | 0.80 | 0.80 | 0.80 | 0.80 | 0.80 | 0.80 | 0.80 | 0.80 | 0.80 | 0.80 | 0.80 |
| 800 | 0.80 | 0.80 | 0.80 | 0.80 | 0.80 | 0.80 | 0.80 | 0.80 | 0.80 | 0.80 | 0.80 | 0.80 | 0.80 |
| 820 | 0.80 | 0.80 | 0.80 | 0.80 | 0.80 | 0.80 | 0.80 | 0.80 | 0.80 | 0.80 | 0.80 | 0.80 | 0.80 |
| 840 | 0.80 | 0.80 | 0.80 | 0.80 | 0.80 | 0.80 | 0.80 | 0.80 | 0.80 | 0.80 | 0.80 | 0.80 | 0.80 |
| 860 | 0.80 | 0.80 | 0.80 | 0.80 | 0.80 | 0.80 | 0.80 | 0.80 | 0.80 | 1.06 | 0.80 | 0.80 | 0.80 |
| 880 | 0.80 | 0.80 | 0.80 | 0.80 | 0.80 | 0.80 | 0.80 | 0.80 | 0.80 | 0.80 | 0.80 | 0.80 | 0.80 |
| 900 | 0.80 | 0.80 | 0.80 | 0.80 | 0.80 | 0.80 | 0.80 | 0.80 | 0.80 | 0.80 | 0.80 | 0.80 | 0.80 |
| 920 | 0.80 | 0.80 | 0.80 | 0.80 | 0.80 | 0.80 | 0.80 | 0.80 | 0.80 | 0.80 | 0.80 | 0.80 | 0.80 |
| 940 | 0.80 | 0.80 | 0.80 | 0.80 | 0.80 | 0.80 | 0.80 | 0.80 | 0.80 | 0.80 | 0.80 | 0.80 | 0.80 |
| 960 | 0.66 | 1.40 | 1.67 | 1.75 | 1.82 | 2.07 | 2.20 | 2.44 | 2.32 | 2.50 | 0.78 | 0.80 | 0.80 |
| 980 | 1.19 | 1.79 | 1.95 | 2.10 | 2.18 | 2.13 | 2.26 | 2.34 | 2.41 | 2.42 | 1.41 | 1.48 | 1.64 |
| 1000 | 1.64 | 1.74 | 2.29 | 2.35 | 2.30 | 2.37 | 2.42 | 2.49 | 2.45 | 2.50 | 1.87 | 2.02 | 2.06 |
| 1020 | 2.10 | 2.32 | 2.50 | 2.37 | 2.45 | 2.46 | 2.42 | 2.45 | 2.49 | 2.50 | 2.32 | 2.29 | 2.25 |
| 1040 | 2.50 | 2.50 | 2.50 | 2.50 | 2.50 | 2.48 | 2.50 | 2.50 | 2.50 | 2.50 | 2.50 | 2.50 | 2.44 |
| 1060 | | | | | | | | | | | | | |
| 1080 | | | | | | | | | | | | | 2.50 |

Fig. 14b

| | | | | | | | | | | | | | |
|---|---|---|---|---|---|---|---|---|---|---|---|---|---|
| 1100 | 0.23 | 0.47 | 0.74 | 1.05 | 0.90 | 1.12 | 1.69 | 1.82 | 2.34 | 2.22 | 0.35 | 0.63 | 0.81 |
| 1120 | 0.24 | 0.71 | 1.20 | 1.49 | 1.48 | 1.85 | 1.89 | 2.14 | 2.37 | 2.50 | 1.10 | 1.25 | 1.31 |
| 1140 | 1.32 | 1.46 | 1.76 | 1.97 | 1.91 | 2.23 | 2.28 | 2.25 | 2.41 | 2.43 | 1.55 | 1.67 | 2.18 |
| 1160 | 1.78 | 1.88 | 1.99 | 2.22 | 2.42 | 2.47 | 2.38 | 2.37 | 2.45 | 2.50 | 2.01 | 2.09 | 2.18 |
| 1180 | 2.23 | 2.31 | 2.50 | 2.36 | 2.47 | 2.50 | 2.48 | 2.50 | 2.47 | 2.47 | 2.50 | 2.50 | 2.50 |
| 1200 | 0.12 | 0.24 | 0.33 | 0.63 | 0.64 | 0.51 | 1.30 | 1.50 | 1.70 | 1.90 | 0.17 | 0.27 | 0.29 |
| 1220 | 0.26 | 0.50 | 0.55 | 0.87 | 0.79 | 1.11 | 1.31 | 1.83 | 2.29 | 2.50 | 0.14 | 0.60 | 0.73 |
| 1240 | 0.17 | 0.54 | 0.84 | 1.39 | 1.71 | 1.77 | 1.81 | 2.01 | 2.16 | 2.50 | 0.80 | 1.37 | 1.51 |
| 1260 | 1.46 | 1.59 | 1.71 | 2.08 | 2.20 | 2.16 | 2.31 | 2.36 | 2.35 | 2.45 | 1.69 | 1.80 | 2.16 |
| 1280 | 1.92 | 2.02 | 2.12 | 2.33 | 2.50 | 2.44 | 2.41 | 2.44 | 2.45 | 2.47 | 2.14 | 2.23 | 2.32 |
| 1300 | 0.07 | 0.16 | 0.22 | 0.36 | 0.31 | 0.80 | 0.80 | 1.18 | 1.38 | 1.58 | 0.10 | 0.20 | 0.19 |
| 1320 | 0.11 | 0.22 | 0.33 | 0.41 | 0.64 | 0.64 | 1.16 | 1.48 | 2.40 | 2.50 | 0.17 | 0.41 | 0.68 |
| 1340 | 0.00 | 0.80 | 1.00 | 0.82 | 1.25 | 1.18 | 1.40 | 1.59 | 1.95 | 2.50 | 0.19 | 0.80 | 1.00 |
| 1360 | 1.14 | 0.80 | 1.41 | 1.55 | 1.96 | 1.90 | 1.90 | 2.14 | 2.26 | 2.41 | 1.37 | 1.50 | 1.62 |
| 1380 | 1.60 | 1.71 | 1.83 | 1.94 | 2.41 | 2.40 | 2.29 | 2.32 | 2.41 | 2.48 | 1.83 | 1.93 | 2.03 |
| 1400 | 0.09 | 0.11 | 0.09 | 0.19 | 0.20 | 0.19 | 0.80 | 0.80 | 1.06 | 1.26 | 0.06 | 0.06 | 0.12 |
| 1420 | 0.00 | 0.00 | 0.18 | 0.49 | 0.38 | 0.39 | 0.80 | 1.18 | 1.36 | 1.54 | 0.10 | 0.29 | 0.18 |
| 1440 | 0.80 | 0.26 | 0.33 | 0.80 | 0.80 | 1.18 | 0.80 | 1.50 | 2.39 | 1.82 | 0.80 | 0.80 | 0.80 |
| 1460 | 0.80 | 0.21 | 0.16 | 1.25 | 1.39 | 1.53 | 1.67 | 1.82 | 1.96 | 2.50 | 0.80 | 0.80 | 0.80 |
| 1480 | 1.28 | 1.40 | 1.52 | 1.65 | 1.77 | 2.36 | 2.40 | 2.37 | 2.29 | 2.46 | 1.51 | 1.18 | 1.73 |
| 1500 | 0.00 | 0.00 | 0.09 | 0.00 | 0.00 | 0.80 | 0.80 | 0.80 | 0.75 | 0.95 | 0.00 | 0.20 | 0.00 |
| 1520 | 0.06 | 0.06 | 0.19 | 0.17 | 0.18 | 0.21 | 0.80 | 0.87 | 1.05 | 1.24 | 0.80 | 0.00 | 0.00 |
| 1540 | 0.80 | 0.80 | 0.13 | 0.36 | 1.09 | 0.87 | 0.80 | 1.20 | 1.36 | 1.53 | 0.80 | 0.80 | 0.80 |
| 1560 | 0.80 | 0.80 | 0.80 | 0.80 | 1.47 | 1.24 | 1.38 | 1.53 | 1.67 | 2.29 | 0.80 | 0.80 | 0.80 |
| 1580 | 0.96 | 1.09 | 1.22 | 1.35 | 0.80 | 1.60 | 2.16 | 2.23 | 2.17 | 2.11 | 1.19 | 1.31 | 1.01 |
| 1600 | 0.00 | 0.80 | 0.80 | 0.80 | 0.80 | 0.80 | 0.80 | 0.80 | 0.80 | 0.80 | 0.00 | 0.00 | 0.00 |
| 1620 | 0.80 | 0.00 | 0.15 | 0.00 | 0.00 | 0.21 | 0.80 | 0.87 | 0.80 | 0.95 | 0.80 | 0.00 | 0.00 |
| 1640 | 0.80 | 0.80 | 0.00 | 0.17 | 0.18 | 0.93 | 1.08 | 0.90 | 1.06 | 1.23 | 0.80 | 0.80 | 0.80 |
| 1660 | 0.80 | 0.80 | 0.80 | 0.80 | 0.80 | 0.93 | 1.08 | 1.23 | 1.38 | 1.53 | 0.80 | 0.80 | 0.70 |
| 1680 | 0.80 | 0.78 | 0.91 | 1.04 | 1.17 | 1.30 | 1.43 | 1.57 | 1.70 | 2.27 | 0.87 | 1.00 | 1.12 |

Fig. 14b'

| | | | | | | | | | | | | |
|---|---|---|---|---|---|---|---|---|---|---|---|---|
| 1700 | 0.80 | 0.80 | 0.80 | 0.80 | 0.80 | 0.80 | 0.80 | 0.80 | 0.80 | 0.80 | 0.80 | 0.80 |
| 1720 | 0.80 | 0.80 | 0.80 | 0.80 | 0.80 | 0.80 | 0.80 | 0.80 | 0.80 | 0.80 | 0.80 | 0.80 |
| 1740 | 0.80 | 0.80 | 0.80 | 0.80 | 0.80 | 0.80 | 0.80 | 0.80 | 0.80 | 0.80 | 0.80 | 0.80 |
| 1760 | 0.80 | 0.80 | 0.80 | 0.32 | 0.80 | 0.80 | 0.78 | 0.80 | 0.80 | 1.23 | 0.80 | 0.80 |
| 1780 | 0.80 | 0.80 | 0.80 | 0.80 | 0.80 | 1.00 | 1.13 | 1.27 | 1.40 | 1.54 | 0.80 | 0.81 |
| 1800 | 0.80 | 0.80 | 0.80 | 0.80 | 0.80 | 0.80 | 0.80 | 0.80 | 0.00 | 0.00 | 0.80 | 0.80 |
| 1820 | 0.80 | 0.80 | 0.80 | 0.80 | 0.80 | 0.80 | 0.80 | 0.80 | 0.12 | 0.30 | 0.80 | 0.80 |
| 1840 | 0.80 | 0.80 | 0.80 | 0.80 | 0.80 | 0.69 | 0.80 | 0.28 | 0.45 | 0.62 | 0.80 | 0.80 |
| 1860 | 0.80 | 0.80 | 0.80 | 0.80 | 0.80 | 0.80 | 0.80 | 0.62 | 0.78 | 0.93 | 0.80 | 0.80 |
| 1880 | 0.80 | 0.80 | 0.80 | 0.80 | 0.80 | 0.80 | 0.80 | 0.97 | 1.10 | 1.24 | 0.80 | 0.80 |
| 1900 | 0.80 | 0.80 | 0.80 | 0.00 | 0.80 | 0.80 | 0.80 | 0.80 | 0.80 | 0.80 | 0.80 | 0.80 |
| 1920 | 0.80 | 0.80 | 0.80 | 0.80 | 0.80 | 0.80 | 0.80 | 0.80 | 0.80 | 0.80 | 0.80 | 0.80 |
| 1940 | 0.80 | 0.80 | 0.80 | 0.80 | 0.80 | 0.80 | 0.80 | 0.80 | 0.14 | 0.31 | 0.80 | 0.80 |
| 1960 | 0.67 | 0.80 | 0.80 | 0.80 | 0.25 | 0.38 | 0.52 | 0.66 | 0.47 | 0.62 | 0.00 | 0.05 |
| 1980 | 0.21 | 1.18 | 1.53 | 1.92 | 1.79 | 2.12 | 2.09 | 2.28 | 0.80 | 0.94 | 0.53 | 0.92 |
| 2000 | 1.36 | 1.23 | 1.39 | 2.18 | 2.24 | 2.21 | 2.36 | 2.45 | 2.50 | 2.36 | 1.22 | 1.36 |
| 2020 | 1.64 | 1.50 | 2.12 | 2.29 | 2.20 | 2.46 | 2.40 | 2.38 | 2.42 | 2.50 | 1.50 | 1.63 |
| 2040 | 1.93 | 1.76 | 2.27 | 2.50 | 2.42 | 2.47 | 2.50 | 2.50 | 2.45 | 2.50 | 1.79 | 1.89 |
| 2060 | 0.17 | 2.02 | 2.50 | 2.50 | 2.50 | 2.46 | 2.50 | 2.43 | 2.48 | 2.50 | 2.07 | 2.15 |
| 2080 | 0.19 | 0.45 | 0.71 | 0.85 | 1.11 | 1.23 | 1.83 | 2.16 | 2.32 | 2.06 | 0.26 | 0.39 |
| 2100 | 0.00 | 0.54 | 0.72 | 0.97 | 1.38 | 1.64 | 1.78 | 2.22 | 2.31 | 2.41 | 0.00 | 0.76 |
| 2120 | 1.35 | 0.80 | 1.38 | 1.69 | 1.94 | 1.94 | 2.16 | 2.23 | 2.30 | 2.50 | 1.20 | 1.36 |
| 2140 | 1.63 | 1.50 | 1.65 | 2.13 | 2.22 | 2.27 | 2.42 | 2.46 | 2.44 | 2.45 | 1.49 | 1.64 |
| 2160 | 1.77 | 1.92 | 2.50 | 2.38 | 2.47 | 2.42 | 2.48 | 2.50 | 2.50 | 1.77 | 1.91 | 1.79 |
| 2180 | 1.63 | 1.77 | 1.92 | 2.50 | 2.38 | 2.47 | 2.42 | 2.48 | 2.50 | 2.50 | 1.77 | 2.06 |
| 2200 | 0.09 | 0.24 | 0.38 | 0.52 | 0.65 | 0.56 | 1.24 | 1.41 | 1.59 | 1.76 | 0.09 | 0.31 |

Fig. 14c

| | | | | | | | | | | | | | |
|---|---|---|---|---|---|---|---|---|---|---|---|---|---|
| 2220 | 0.18 | 0.35 | 0.40 | 0.72 | 0.79 | 1.08 | 1.49 | 1.78 | 2.18 | 2.50 | 0.15 | 0.46 | 0.79 |
| 2240 | 0.09 | 0.48 | 0.59 | 0.93 | 1.33 | 1.51 | 1.73 | 1.98 | 2.10 | 2.50 | 0.80 | 0.80 | 1.24 |
| 2260 | 0.80 | 0.80 | 1.38 | 1.76 | 1.84 | 2.08 | 2.21 | 2.18 | 2.18 | 2.45 | 1.19 | 1.35 | 1.52 |
| 2280 | 1.33 | 1.49 | 1.66 | 1.82 | 2.28 | 2.44 | 2.36 | 2.34 | 2.44 | 2.48 | 1.47 | 1.63 | 1.80 |
| 2300 | 0.04 | 0.08 | 0.14 | 0.27 | 0.31 | 0.58 | 0.80 | 1.11 | 1.29 | 1.46 | 0.05 | 0.05 | 0.23 |
| 2320 | 0.04 | 0.14 | 0.27 | 0.30 | 0.63 | 0.64 | 0.77 | 1.13 | 1.57 | 1.74 | 0.12 | 0.25 | 0.37 |
| 2340 | 0.20 | 0.15 | 0.46 | 0.48 | 0.91 | 1.01 | 1.41 | 1.42 | 1.99 | 2.31 | 0.36 | 0.32 | 0.65 |
| 2360 | 0.00 | 0.00 | 0.80 | 1.27 | 1.44 | 1.67 | 1.79 | 1.97 | 2.04 | 2.43 | 0.80 | 0.80 | 1.23 |
| 2380 | 0.80 | 0.80 | 1.38 | 1.55 | 2.08 | 2.04 | 2.29 | 2.38 | 2.24 | 2.43 | 1.17 | 1.34 | 1.52 |
| 2400 | 0.06 | 0.11 | 0.16 | 0.27 | 0.40 | 0.25 | 0.64 | 0.80 | 0.80 | 1.16 | 0.01 | 0.06 | 0.07 |
| 2420 | 0.00 | 0.05 | 0.09 | 0.13 | 0.12 | 0.42 | 0.58 | 1.10 | 1.28 | 1.45 | 0.08 | 0.18 | 0.26 |
| 2440 | 0.13 | 0.18 | 0.17 | 0.47 | 0.32 | 0.57 | 1.06 | 1.22 | 1.57 | 1.75 | 0.00 | 0.07 | 0.57 |
| 2460 | 0.80 | 0.28 | 0.44 | 0.80 | 1.16 | 1.33 | 1.54 | 1.68 | 1.50 | 2.50 | 0.80 | 0.80 | 0.80 |
| 2480 | 0.80 | 0.80 | 1.09 | 1.26 | 1.44 | 2.06 | 2.10 | 2.13 | 2.40 | 2.39 | 0.87 | 1.05 | 1.23 |
| 2500 | 0.02 | 0.03 | 0.00 | 0.07 | 0.15 | 0.80 | 0.80 | 0.80 | 0.80 | 0.80 | 0.02 | 0.05 | 0.05 |
| 2520 | 0.00 | 0.02 | 0.19 | 0.11 | 0.12 | 0.21 | 0.44 | 0.80 | 0.80 | 1.16 | 0.00 | 0.09 | 0.34 |
| 2540 | 0.00 | 0.18 | 0.40 | 0.24 | 0.43 | 0.80 | 0.60 | 0.80 | 1.29 | 1.46 | 0.00 | 0.09 | 0.23 |
| 2560 | 0.80 | 0.00 | 0.80 | 0.29 | 0.87 | 0.80 | 1.23 | 1.41 | 1.59 | 2.32 | 0.80 | 0.80 | 0.80 |
| 2580 | 0.80 | 0.80 | 0.80 | 0.80 | 1.16 | 1.34 | 1.52 | 2.05 | 2.07 | 2.26 | 0.80 | 0.80 | 0.80 |
| 2600 | 0.00 | 0.06 | 0.23 | 0.00 | 0.80 | 0.80 | 0.80 | 0.80 | 0.80 | 0.56 | 0.00 | 0.00 | 0.00 |
| 2620 | 0.06 | 0.14 | 0.13 | 0.29 | 0.10 | 0.09 | 0.31 | 0.80 | 0.80 | 0.87 | 0.00 | 0.00 | 0.16 |
| 2640 | 0.80 | 0.00 | 0.19 | 0.21 | 0.33 | 0.33 | 0.94 | 0.80 | 1.30 | 1.18 | 0.00 | 0.19 | 0.00 |
| 2660 | 0.80 | 0.80 | 0.21 | 0.80 | 0.00 | 0.80 | 1.24 | 1.42 | 1.61 | 1.48 | 0.80 | 0.80 | 0.80 |
| 2680 | 0.80 | 0.80 | 0.80 | 0.80 | 0.80 | 1.05 | 0.80 | 0.80 | 0.80 | 1.85 | 0.80 | 0.80 | 0.64 |
| 2700 | 0.00 | 0.00 | 0.00 | 0.00 | 0.80 | 0.80 | 0.80 | 0.80 | 0.80 | 0.80 | 0.19 | 0.00 | 0.21 |
| 2720 | 0.06 | 0.00 | 0.00 | 0.00 | 0.80 | 0.80 | 0.35 | 0.80 | 0.80 | 0.89 | 0.80 | 0.00 | 0.00 |
| 2740 | 0.80 | 0.80 | 0.80 | 0.80 | 0.80 | 0.80 | 0.80 | 0.80 | 0.80 | 0.80 | 0.80 | 0.00 | 0.80 |
| 2760 | 0.80 | 0.80 | 0.80 | 0.80 | 0.80 | 0.80 | 0.80 | 0.83 | 1.01 | 1.20 | 0.80 | 0.80 | 0.80 |

Fig. 14c'

| | | | | | | | | | | | | | |
|---|---|---|---|---|---|---|---|---|---|---|---|---|---|
| 2780 | 0.80 | 0.80 | 0.80 | 0.80 | 0.80 | 0.80 | 0.95 | 1.14 | 1.32 | 1.51 | 0.80 | 0.80 | 0.80 |
| 2800 | 0.80 | 0.80 | 0.80 | 0.80 | 0.80 | 0.80 | 0.80 | 0.80 | 0.80 | 0.80 | 0.80 | 0.80 | 0.80 |
| 2820 | 0.80 | 0.80 | 0.80 | 0.80 | 0.80 | 0.80 | 0.80 | 0.80 | 0.80 | 0.28 | 0.80 | 0.80 | 0.80 |
| 2840 | 0.80 | 0.80 | 0.80 | 0.80 | 0.80 | 0.80 | 0.80 | 0.54 | 0.41 | 0.59 | 0.80 | 0.80 | 0.80 |
| 2860 | 0.80 | 0.80 | 0.80 | 0.80 | 0.80 | 0.47 | 0.35 | 0.85 | 0.72 | 0.91 | 0.80 | 0.80 | 0.80 |
| 2880 | 0.80 | 0.80 | 0.80 | 0.80 | 0.80 | 0.80 | 0.66 | 0.80 | 1.04 | 1.22 | 0.80 | 0.80 | 0.80 |
| 2900 | 0.80 | 0.80 | 0.80 | 0.80 | 0.80 | 0.80 | 0.80 | 0.80 | 0.80 | 0.80 | 0.80 | 0.80 | 0.80 |
| 2920 | 0.80 | 0.80 | 0.80 | 0.80 | 0.80 | 0.80 | 0.80 | 0.25 | 0.12 | 0.30 | 0.80 | 0.80 | 0.80 |
| 2940 | 0.80 | 0.80 | 0.80 | 0.80 | 0.80 | 0.18 | 0.37 | 0.56 | 0.43 | 0.62 | 0.80 | 0.80 | 0.80 |
| 2960 | 0.80 | 0.80 | 0.80 | 0.80 | 0.80 | 2.22 | 1.89 | 2.34 | 0.75 | 0.93 | 0.60 | 1.06 | 1.74 |
| 2980 | 0.53 | 1.25 | 1.60 | 2.06 | 1.92 | 2.33 | 2.41 | 2.38 | 2.50 | 2.13 | 0.80 | 1.15 | 1.32 |
| 3000 | 0.80 | 1.10 | 1.26 | 1.42 | 2.11 | 2.45 | 2.30 | 2.44 | 2.45 | 2.50 | 1.07 | 1.25 | 1.43 |
| 3020 | 1.03 | 1.20 | 1.37 | 1.54 | 2.25 | 2.16 | 2.42 | 2.50 | 2.50 | 2.50 | 1.15 | 1.35 | 1.54 |
| 3040 | 1.11 | 1.30 | 1.49 | 1.70 | 2.50 | 2.50 | 2.50 | 2.50 | 2.50 | 2.50 | 1.24 | 1.45 | 1.65 |
| 3060 | 1.20 | 1.40 | 1.60 | 2.50 | 2.50 | 1.39 | 1.96 | 1.60 | 1.74 | 1.88 | 0.15 | 0.31 | 0.58 |
| 3080 | 0.16 | 0.50 | 0.85 | 1.00 | 1.31 | 1.68 | 1.84 | 2.21 | 2.35 | 2.50 | 0.11 | 0.23 | 0.80 |
| 3100 | 0.13 | 0.33 | 0.71 | 1.08 | 1.55 | 1.68 | 1.94 | 2.21 | 2.34 | 2.50 | 0.80 | 0.80 | 1.20 |
| 3120 | 0.80 | 0.80 | 1.14 | 1.32 | 1.90 | 2.21 | 2.23 | 2.22 | 2.34 | 2.47 | 0.90 | 1.11 | 1.32 |
| 3140 | 0.80 | 1.06 | 1.26 | 1.46 | 2.21 | 2.50 | 2.45 | 2.50 | 2.50 | 2.47 | 0.98 | 1.21 | 1.44 |
| 3160 | 0.94 | 1.16 | 1.38 | 2.38 | 2.39 | 0.77 | 1.21 | 1.35 | 1.49 | 1.63 | 0.04 | 0.17 | 0.25 |
| 3180 | 0.07 | 0.21 | 0.38 | 0.51 | 0.56 | 0.97 | 1.36 | 1.78 | 2.28 | 2.50 | 0.06 | 0.29 | 0.59 |
| 3200 | 0.06 | 0.22 | 0.42 | 0.47 | 0.74 | 1.35 | 1.51 | 1.73 | 2.24 | 2.35 | 0.80 | 0.47 | 0.80 |
| 3220 | 0.00 | 0.44 | 0.56 | 0.91 | 1.14 | 1.74 | 2.11 | 2.01 | 2.17 | 2.38 | 0.80 | 0.80 | 1.08 |
| 3240 | 0.80 | 0.80 | 1.02 | 1.22 | 1.91 | 2.06 | 2.33 | 2.36 | 2.36 | 2.45 | 0.80 | 0.80 | 1.20 |
| 3260 | 0.80 | 0.80 | 1.14 | 1.36 | 1.59 | 0.80 | 0.95 | 1.09 | 1.23 | 1.37 | 0.08 | 0.02 | 0.21 |
| 3280 | 0.05 | 0.13 | 0.13 | 0.28 | 0.30 | 0.38 | 0.92 | 1.29 | 1.49 | 1.65 | 0.05 | 0.19 | 0.23 |
| 3300 | 0.00 | 0.09 | 0.18 | 0.29 | 0.44 | | | | | | | | |

Fig. 14d

| | | | | | | | | | | | | |
|---|---|---|---|---|---|---|---|---|---|---|---|---|
| 3340 | 0.14 | 0.15 | 0.37 | 0.47 | 0.57 | 0.63 | 1.07 | 1.35 | 1.85 | 2.43 | 0.20 | 0.06 | 0.37 |
| 3360 | 0.21 | 0.10 | 0.54 | 0.80 | 1.06 | 1.03 | 1.59 | 1.52 | 1.95 | 2.41 | 0.80 | 0.80 | 0.80 |
| 3380 | 0.80 | 0.80 | 0.80 | 1.12 | 1.35 | 2.07 | 1.94 | 2.17 | 2.22 | 2.36 | 0.80 | 0.80 | 0.96 |
| 3400 | 0.02 | 0.05 | 0.11 | 0.23 | 0.28 | 0.08 | 0.80 | 0.80 | 0.98 | 1.12 | 0.03 | 0.07 | 0.04 |
| 3420 | 0.01 | 0.05 | 0.11 | 0.13 | 0.20 | 0.25 | 0.34 | 0.80 | 1.24 | 1.40 | 0.08 | 0.08 | 0.16 |
| 3440 | 0.05 | 0.18 | 0.18 | 0.39 | 0.35 | 0.44 | 0.70 | 1.28 | 1.50 | 1.69 | 0.06 | 0.11 | 0.15 |
| 3460 | 0.13 | 0.10 | 0.28 | 0.63 | 0.61 | 0.77 | 1.04 | 1.33 | 1.46 | 2.31 | 0.00 | 0.25 | 0.26 |
| 3480 | 0.80 | 0.80 | 0.80 | 0.87 | 0.80 | 1.33 | 1.56 | 1.77 | 2.00 | 2.41 | 0.80 | 0.80 | 0.80 |
| 3500 | 0.05 | 0.02 | 0.18 | 0.10 | 0.24 | 0.14 | 0.23 | 0.80 | 0.80 | 0.87 | 0.01 | 0.01 | 0.07 |
| 3520 | 0.00 | 0.00 | 0.09 | 0.10 | 0.13 | 0.24 | 0.36 | 0.52 | 0.80 | 1.15 | 0.00 | 0.05 | 0.10 |
| 3540 | 0.00 | 0.06 | 0.13 | 0.14 | 0.20 | 0.34 | 0.44 | 0.71 | 1.25 | 1.44 | 0.00 | 0.04 | 0.06 |
| 3560 | 0.80 | 0.00 | 0.15 | 0.45 | 0.33 | 0.80 | 0.83 | 1.13 | 1.51 | 1.72 | 0.80 | 0.00 | 0.29 |
| 3580 | 0.80 | 0.80 | 0.80 | 0.80 | 0.85 | 1.09 | 1.32 | 1.55 | 1.77 | 2.28 | 0.80 | 0.80 | 0.80 |
| 3600 | 0.00 | 0.06 | 0.11 | 0.00 | 0.00 | 0.80 | 0.80 | 0.80 | 0.80 | 0.80 | 0.00 | 0.00 | 0.00 |
| 3620 | 0.00 | 0.00 | 0.09 | 0.06 | 0.03 | 0.11 | 0.16 | 0.21 | 0.80 | 0.90 | 0.00 | 0.03 | 0.09 |
| 3640 | 0.12 | 0.00 | 0.00 | 0.14 | 0.19 | 0.15 | 0.28 | 0.43 | 0.80 | 1.19 | 0.00 | 0.07 | 0.00 |
| 3660 | 0.00 | 0.09 | 0.00 | 0.29 | 0.18 | 0.38 | 0.58 | 0.49 | 1.27 | 1.48 | 0.00 | 0.00 | 0.13 |
| 3680 | 0.80 | 0.80 | 0.80 | 0.23 | 0.61 | 0.80 | 0.80 | 1.30 | 1.53 | 1.76 | 0.80 | 0.80 | 0.80 |
| 3700 | 0.00 | 0.80 | 0.80 | 0.80 | 0.80 | 0.80 | 0.80 | 0.80 | 0.80 | 0.80 | 0.00 | 0.14 | 0.14 |
| 3720 | 0.00 | 0.12 | 0.10 | 0.15 | 0.00 | 0.11 | 0.14 | 0.80 | 0.80 | 0.80 | 0.00 | 0.00 | 0.07 |
| 3740 | 0.00 | 0.34 | 0.07 | 0.00 | 0.19 | 0.23 | 0.80 | 0.80 | 0.80 | 0.94 | 0.00 | 0.00 | 0.00 |
| 3760 | 0.80 | 0.00 | 0.80 | 0.00 | 0.16 | 0.16 | 0.82 | 1.05 | 1.02 | 1.23 | 0.80 | 0.80 | 0.80 |
| 3780 | 0.80 | 0.80 | 0.80 | 0.80 | 0.80 | 0.00 | 0.80 | 0.80 | 1.28 | 1.51 | 0.80 | 0.80 | 0.80 |
| 3800 | 0.80 | 0.80 | 0.80 | 0.80 | 0.80 | 0.80 | 0.80 | 0.80 | 0.80 | 0.80 | 0.80 | 0.80 | 0.80 |
| 3820 | 0.80 | 0.80 | 0.80 | 0.80 | 0.80 | 0.80 | 0.80 | 0.80 | 0.80 | 0.80 | 0.80 | 0.80 | 0.80 |
| 3840 | 0.80 | 0.80 | 0.80 | 0.80 | 0.80 | 0.23 | 0.80 | 0.80 | 0.77 | 0.69 | 0.80 | 0.80 | 0.80 |
| 3860 | 0.80 | 0.80 | 0.80 | 0.80 | 0.80 | 0.80 | 0.80 | 0.80 | 0.77 | 0.98 | 0.80 | 0.80 | 0.80 |
| 3880 | 0.80 | 0.80 | 0.80 | 0.80 | 0.80 | 0.80 | 0.57 | 0.80 | 1.03 | 1.27 | 0.80 | 0.80 | 0.80 |

Fig. 14d¹

| | | | | | | | | | | | | |
|---|---|---|---|---|---|---|---|---|---|---|---|---|
| 3900 | 0.80 | 0.80 | 0.80 | 0.80 | 0.80 | 0.80 | 0.80 | 0.80 | 0.80 | 0.80 | 0.80 | 0.80 |
| 3920 | 0.80 | 0.80 | 0.80 | 0.80 | 0.80 | 0.80 | 0.80 | 0.80 | 0.80 | 0.80 | 0.80 | 0.80 |
| 3940 | 0.80 | 0.80 | 0.80 | 0.80 | 0.80 | 0.80 | 0.80 | 0.80 | 0.80 | 0.44 | 0.80 | 0.80 |
| 3960 | 0.80 | 0.80 | 0.80 | 0.80 | 0.80 | 0.80 | 0.80 | 0.80 | 0.52 | 0.73 | 0.80 | 0.80 |
| 3980 | 0.80 | 0.80 | 1.73 | 2.18 | 2.30 | 0.80 | 0.32 | 0.55 | 0.78 | 1.02 | 0.80 | 0.80 |
| 4000 | 0.39 | 1.29 | 1.24 | 1.40 | 2.39 | 2.50 | 2.40 | 2.34 | 2.00 | 2.13 | 0.80 | 2.02 |
| 4020 | 0.80 | 1.08 | 1.29 | 1.47 | 1.66 | 2.41 | 2.22 | 2.50 | 2.50 | 2.36 | 0.80 | 1.27 |
| 4040 | 0.80 | 1.10 | 1.33 | 1.55 | 1.76 | 2.50 | 2.50 | 2.50 | 2.50 | 2.50 | 0.80 | 1.31 |
| 4060 | 0.80 | 1.12 | 1.38 | 1.62 | 1.86 | 2.50 | 2.50 | 2.50 | 2.50 | 2.50 | 0.80 | 1.35 |
| 4080 | 0.80 | 1.14 | 1.01 | 0.95 | 1.23 | 2.17 | 2.50 | 2.37 | 2.50 | 1.90 | 0.80 | 1.40 |
| 4100 | 0.19 | 0.55 | 0.80 | 0.80 | 1.33 | 1.49 | 1.50 | 1.63 | 1.77 | 2.50 | 0.10 | 0.76 |
| 4120 | 0.00 | 0.47 | 1.05 | 1.24 | 1.42 | 2.00 | 1.84 | 1.60 | 2.37 | 2.50 | 0.13 | 0.80 |
| 4140 | 0.80 | 0.80 | 0.80 | 1.31 | 1.52 | 2.22 | 2.04 | 2.33 | 2.30 | 2.46 | 0.80 | 0.80 |
| 4160 | 0.80 | 0.80 | 1.14 | 1.37 | 2.50 | 2.17 | 2.32 | 2.27 | 2.50 | 2.50 | 0.80 | 1.12 |
| 4180 | 0.80 | 0.80 | 0.38 | 0.73 | 0.80 | 1.13 | 2.50 | 2.50 | 2.50 | 1.67 | 0.01 | 1.16 |
| 4200 | 0.06 | 0.26 | 0.43 | 0.53 | 0.78 | 1.11 | 1.27 | 1.40 | 1.54 | 2.25 | 0.00 | 0.28 |
| 4220 | 0.03 | 0.21 | 0.41 | 0.61 | 1.19 | 1.37 | 1.41 | 1.77 | 2.14 | 2.50 | 0.00 | 0.53 |
| 4240 | 0.13 | 0.07 | 0.80 | 1.07 | 1.28 | 1.49 | 1.56 | 1.93 | 2.37 | 2.50 | 0.80 | 0.19 |
| 4260 | 0.80 | 0.80 | 0.80 | 1.14 | 1.37 | 2.20 | 2.22 | 2.10 | 2.35 | 2.38 | 0.80 | 0.88 |
| 4280 | 0.80 | 0.80 | 0.80 | 0.40 | 0.80 | 0.80 | 2.26 | 2.20 | 2.35 | 2.50 | 0.04 | 0.80 |
| 4300 | 0.05 | 0.06 | 0.21 | 0.29 | 0.45 | 0.73 | 1.04 | 1.17 | 1.30 | 1.44 | 0.03 | 0.21 |
| 4320 | 0.03 | 0.09 | 0.14 | 0.53 | 0.71 | 0.69 | 1.18 | 1.34 | 1.50 | 2.50 | 0.00 | 0.23 |
| 4340 | 0.00 | 0.16 | 0.24 | 0.80 | 0.80 | 1.26 | 1.02 | 1.28 | 1.80 | 2.30 | 0.00 | 0.27 |
| 4360 | 0.80 | 0.00 | 0.14 | 0.90 | 1.14 | 1.37 | 1.18 | 1.77 | 1.81 | 2.29 | 0.80 | 0.23 |
| 4380 | 0.80 | 0.80 | 0.80 | 0.36 | 0.20 | 0.80 | 1.86 | 2.22 | 2.18 | 2.36 | 0.80 | 0.80 |
| 4400 | 0.03 | 0.03 | 0.13 | 0.10 | 0.15 | 0.40 | 0.80 | 0.80 | 1.07 | 1.20 | 0.02 | 0.07 |
| 4420 | 0.02 | 0.12 | 0.07 | 0.37 | 0.32 | 0.30 | 0.82 | 0.79 | 1.26 | 2.36 | 0.02 | 0.12 |
| 4440 | 0.00 | 0.11 | 0.10 | 0.27 | 0.51 | 0.69 | 0.56 | 1.07 | 1.29 | 2.22 | 0.04 | 0.22 |
| 4460 | 0.09 | 0.00 | 0.23 | | | | 0.87 | | 1.36 | | 0.00 | 0.16 |

Fig. 14e

| | | | | | | | | | | | | | |
|---|---|---|---|---|---|---|---|---|---|---|---|---|---|
| 4480 | 0.80 | 0.21 | 0.17 | 0.34 | 0.80 | 0.78 | 1.64 | 1.54 | 1.90 | 2.13 | 0.80 | 0.80 | 0.80 |
| 4500 | 0.00 | 0.06 | 0.13 | 0.08 | 0.08 | 0.00 | 0.80 | 0.80 | 0.84 | 0.97 | 0.02 | 0.01 | 0.03 |
| 4520 | 0.00 | 0.03 | 0.06 | 0.10 | 0.17 | 0.23 | 0.52 | 0.64 | 1.03 | 1.19 | 0.00 | 0.01 | 0.06 |
| 4540 | 0.03 | 0.04 | 0.12 | 0.08 | 0.15 | 0.16 | 0.40 | 0.51 | 1.00 | 1.41 | 0.04 | 0.09 | 0.11 |
| 4560 | 0.00 | 0.11 | 0.03 | 0.16 | 0.31 | 0.30 | 0.71 | 0.90 | 1.01 | 1.63 | 0.00 | 0.00 | 0.11 |
| 4580 | 0.80 | 0.00 | 0.30 | 0.18 | 0.46 | 0.80 | 0.79 | 1.19 | 1.59 | 2.05 | 0.00 | 0.80 | 0.80 |
| 4600 | 0.02 | 0.00 | 0.20 | 0.17 | 0.00 | 0.80 | 0.80 | 0.80 | 0.80 | 0.74 | 0.07 | 0.05 | 0.04 |
| 4620 | 0.00 | 0.00 | 0.04 | 0.11 | 0.08 | 0.04 | 0.31 | 0.39 | 0.17 | 0.96 | 0.80 | 0.00 | 0.03 |
| 4640 | 0.00 | 0.01 | 0.06 | 0.06 | 0.15 | 0.12 | 0.18 | 0.19 | 0.80 | 1.17 | 0.80 | 0.00 | 0.08 |
| 4660 | 0.00 | 0.00 | 0.06 | 0.18 | 0.10 | 0.21 | 0.37 | 0.45 | 0.80 | 1.39 | 0.00 | 0.00 | 0.06 |
| 4680 | 0.80 | 0.05 | 0.03 | 0.07 | 0.29 | 0.48 | 0.60 | 0.76 | 1.18 | 1.61 | 0.00 | 0.09 | 0.80 |
| 4700 | 0.00 | 0.00 | 0.00 | 0.80 | 0.80 | 0.80 | 0.80 | 0.80 | 0.80 | 0.80 | 0.80 | 0.80 | 0.04 |
| 4720 | 0.00 | 0.00 | 0.16 | 0.03 | 0.00 | 0.15 | 0.12 | 0.06 | 0.80 | 0.72 | 0.80 | 0.00 | 0.00 |
| 4740 | 0.00 | 0.00 | 0.00 | 0.00 | 0.03 | 0.07 | 0.15 | 0.39 | 0.14 | 0.94 | 0.80 | 0.00 | 0.09 |
| 4760 | 0.00 | 0.00 | 0.00 | 0.00 | 0.09 | 0.23 | 0.13 | 0.63 | 0.37 | 1.16 | 0.80 | 0.00 | 0.18 |
| 4780 | 0.00 | 0.00 | 0.80 | 0.00 | 0.06 | 0.16 | 0.50 | 0.80 | 0.71 | 1.38 | 0.80 | 0.00 | 0.80 |
| 4800 | 0.80 | 0.80 | 0.11 | 0.80 | 0.80 | 0.80 | 0.80 | 0.80 | 0.80 | 0.80 | 0.80 | 0.80 | 0.17 |
| 4820 | 0.00 | 0.00 | 0.00 | 0.03 | 0.00 | 0.15 | 0.00 | 0.00 | 0.80 | 0.80 | 0.80 | 0.00 | 0.00 |
| 4840 | 0.80 | 0.00 | 0.00 | 0.00 | 0.00 | 0.10 | 0.00 | 0.00 | 0.80 | 0.80 | 0.80 | 0.00 | 0.00 |
| 4860 | 0.80 | 0.00 | 0.00 | 0.00 | 0.09 | 0.00 | 0.34 | 0.00 | 0.80 | 0.80 | 0.80 | 0.80 | 0.80 |
| 4880 | 0.80 | 0.00 | 0.80 | 0.00 | 0.00 | 0.10 | 0.15 | 0.80 | 0.80 | 1.14 | 0.80 | 0.80 | 0.80 |
| 4900 | 0.80 | 0.80 | 0.80 | 0.80 | 0.18 | 0.80 | 0.80 | 0.80 | 0.80 | 0.80 | 0.80 | 0.80 | 0.80 |
| 4920 | 0.80 | 0.80 | 0.80 | 0.80 | 0.80 | 0.80 | 0.80 | 0.80 | 0.80 | 0.80 | 0.80 | 0.80 | 0.80 |
| 4940 | 0.80 | 0.80 | 0.80 | 0.80 | 0.80 | 0.80 | 0.80 | 0.80 | 0.80 | 0.47 | 0.80 | 0.80 | 0.80 |
| 4960 | 0.80 | 0.80 | 0.80 | 0.80 | 0.80 | 0.80 | 0.80 | 0.27 | 0.48 | 0.69 | 0.80 | 0.80 | 0.00 |
| 4980 | 0.80 | 0.80 | 0.80 | 0.80 | 0.80 | 0.80 | 0.80 | 0.80 | 0.80 | 0.91 | 0.80 | 0.80 | 0.00 |
| 5000 | 0.59 | 1.02 | 2.01 | 2.30 | 2.35 | 2.19 | 2.41 | 2.50 | 1.99 | 2.13 | 0.80 | 1.02 | 1.19 |
| 5020 | 0.80 | 1.01 | 1.22 | 2.50 | 2.31 | 2.36 | 2.50 | 2.50 | 2.50 | 2.36 | 0.80 | 1.01 | 1.22 |

Fig. 14e¹

| | | | | | | | | | | | | |
|---|---|---|---|---|---|---|---|---|---|---|---|---|
| 5040 | 0.80 | 1.01 | 1.29 | 1.57 | 2.27 | 2.14 | 2.29 | 2.50 | 2.50 | 2.50 | 0.80 | 1.01 | 1.33 |
| 5060 | 0.80 | 1.01 | 1.36 | 1.71 | 2.07 | 2.50 | 2.50 | 2.50 | 2.50 | 2.50 | 0.80 | 1.01 | 1.40 |
| 5080 | 0.80 | 1.00 | 1.43 | 1.85 | 2.28 | 2.50 | 2.50 | 2.50 | 2.38 | 2.50 | 0.80 | 1.00 | 1.46 |
| 5100 | 0.20 | 0.94 | 1.19 | 1.11 | 1.25 | 1.39 | 2.28 | 1.67 | 2.50 | 1.94 | 0.08 | 0.39 | 0.80 |
| 5120 | 0.18 | 0.13 | 0.80 | 1.16 | 1.34 | 2.27 | 2.05 | 2.07 | 2.44 | 2.50 | 0.80 | 0.80 | 0.80 |
| 5140 | 0.80 | 0.80 | 0.80 | 1.21 | 1.43 | 1.65 | 1.88 | 2.33 | 2.50 | 2.50 | 0.80 | 0.80 | 0.99 |
| 5160 | 0.80 | 0.80 | 1.00 | 1.26 | 1.52 | 1.79 | 2.50 | 2.50 | 2.50 | 2.44 | 0.80 | 0.80 | 1.00 |
| 5180 | 0.80 | 0.80 | 1.01 | 1.31 | 1.61 | 1.92 | 2.32 | 2.50 | 2.50 | 2.50 | 0.06 | 0.28 | 1.01 |
| 5200 | 0.09 | 0.23 | 0.81 | 0.93 | 1.07 | 1.20 | 1.34 | 1.48 | 1.62 | 1.76 | 0.08 | 0.28 | 0.38 |
| 5220 | 0.00 | 0.12 | 0.31 | 0.80 | 1.12 | 1.29 | 1.46 | 1.63 | 2.43 | 2.50 | 0.80 | 0.80 | 0.49 |
| 5240 | 0.00 | 0.25 | 0.80 | 0.80 | 1.17 | 1.37 | 1.57 | 2.13 | 2.33 | 2.50 | 0.80 | 0.80 | 0.80 |
| 5260 | 0.80 | 0.80 | 0.80 | 0.99 | 0.80 | 1.45 | 1.69 | 2.13 | 2.35 | 2.36 | 0.80 | 0.80 | 0.75 |
| 5280 | 0.80 | 0.80 | 0.80 | 1.01 | 1.27 | 1.53 | 2.50 | 2.26 | 2.45 | 2.47 | 0.80 | 0.80 | 0.80 |
| 5300 | 0.06 | 0.21 | 0.50 | 0.80 | 0.80 | 1.02 | 1.16 | 1.30 | 1.44 | 1.58 | 0.03 | 0.21 | 0.20 |
| 5320 | 0.03 | 0.04 | 0.23 | 0.32 | 0.59 | 1.08 | 1.35 | 1.41 | 1.57 | 2.50 | 0.00 | 0.07 | 0.35 |
| 5340 | 0.00 | 0.22 | 0.32 | 0.36 | 0.78 | 0.72 | 1.33 | 1.52 | 2.22 | 2.44 | 0.00 | 0.00 | 0.14 |
| 5360 | 0.80 | 0.00 | 0.23 | 0.18 | 0.48 | 1.19 | 1.41 | 1.94 | 2.01 | 2.40 | 0.80 | 0.80 | 0.80 |
| 5380 | 0.80 | 0.80 | 0.80 | 0.76 | 1.01 | 1.25 | 1.50 | 2.10 | 2.18 | 2.41 | 0.80 | 0.80 | 0.80 |
| 5400 | 0.03 | 0.12 | 0.57 | 0.55 | 0.80 | 0.84 | 0.98 | 1.12 | 1.25 | 1.39 | 0.01 | 0.05 | 0.10 |
| 5420 | 0.00 | 0.05 | 0.17 | 0.17 | 0.40 | 0.50 | 0.73 | 1.20 | 1.37 | 1.53 | 0.00 | 0.00 | 0.08 |
| 5440 | 0.00 | 0.00 | 0.05 | 0.08 | 0.38 | 0.36 | 0.39 | 0.77 | 1.48 | 2.21 | 0.00 | 0.00 | 0.03 |
| 5460 | 0.00 | 0.00 | 0.11 | 0.30 | 0.31 | 0.37 | 0.90 | 1.13 | 1.73 | 2.41 | 0.00 | 0.15 | 0.15 |
| 5480 | 0.80 | 0.80 | 0.00 | 0.00 | 0.80 | 0.80 | 1.24 | 1.83 | 1.97 | 2.30 | 0.80 | 0.80 | 0.80 |
| 5500 | 0.01 | 0.02 | 0.21 | 0.33 | 0.80 | 0.80 | 0.79 | 0.93 | 1.07 | 1.21 | 0.00 | 0.02 | 0.07 |
| 5520 | 0.01 | 0.03 | 0.04 | 0.13 | 0.22 | 0.37 | 0.41 | 0.80 | 1.17 | 0.80 | 0.00 | 0.01 | 0.07 |
| 5540 | 0.03 | 0.00 | 0.05 | 0.12 | 0.26 | 0.23 | 0.31 | 0.60 | 1.26 | 2.26 | 0.00 | 0.03 | 0.06 |
| 5560 | 0.00 | 0.03 | 0.03 | 0.14 | 0.24 | 0.23 | 0.50 | 0.66 | 1.15 | 1.56 | 0.00 | 0.00 | 0.05 |
| 5580 | 0.80 | 0.00 | 0.00 | 0.23 | 0.24 | 0.54 | 0.81 | 1.03 | 1.53 | 2.05 | 0.80 | 0.80 | 0.00 |
| 5600 | 0.04 | 0.07 | 0.15 | 0.18 | 0.19 | 0.80 | 0.80 | 0.80 | 0.89 | 1.03 | 0.01 | 0.03 | 0.02 |

Fig. 14f

| | | | | | | | | | | | | |
|---|---|---|---|---|---|---|---|---|---|---|---|---|
| 5620 | 0.00 | 0.01 | 0.07 | 0.11 | 0.14 | 0.13 | 0.36 | 0.80 | 0.97 | 1.13 | 0.00 | 0.01 | 0.07 |
| 5640 | 0.00 | 0.03 | 0.09 | 0.03 | 0.12 | 0.21 | 0.22 | 0.43 | 0.80 | 1.24 | 0.00 | 0.02 | 0.06 |
| 5660 | 0.00 | 0.00 | 0.06 | 0.07 | 0.07 | 0.19 | 0.24 | 0.63 | 0.82 | 1.34 | 0.00 | 0.00 | 0.00 |
| 5680 | 0.00 | 0.00 | 0.16 | 0.04 | 0.09 | 0.23 | 0.35 | 0.68 | 1.19 | 1.27 | 0.80 | 0.00 | 0.00 |
| 5700 | 0.05 | 0.16 | 0.00 | 0.19 | 0.23 | 0.80 | 0.80 | 0.80 | 0.80 | 0.84 | 0.00 | 0.02 | 0.05 |
| 5720 | 0.02 | 0.00 | 0.04 | 0.05 | 0.08 | 0.12 | 0.00 | 0.18 | 0.80 | 0.94 | 0.00 | 0.06 | 0.02 |
| 5740 | 0.00 | 0.00 | 0.02 | 0.02 | 0.05 | 0.13 | 0.06 | 0.22 | 0.80 | 1.03 | 0.00 | 0.00 | 0.00 |
| 5760 | 0.00 | 0.00 | 0.05 | 0.04 | 0.04 | 0.08 | 0.14 | 0.28 | 0.51 | 1.13 | 0.80 | 0.17 | 0.07 |
| 5780 | 0.00 | 0.00 | 0.08 | 0.09 | 0.07 | 0.19 | 0.19 | 0.44 | 0.67 | 1.22 | 0.00 | 0.00 | 0.00 |
| 5800 | 0.80 | 0.80 | 0.80 | 0.80 | 0.80 | 0.80 | 0.80 | 0.80 | 0.80 | 0.80 | 0.00 | 0.00 | 0.00 |
| 5820 | 0.00 | 0.00 | 0.04 | 0.12 | 0.07 | 0.28 | 0.00 | 0.00 | 0.80 | 0.80 | 0.00 | 0.00 | 0.00 |
| 5840 | 0.00 | 0.00 | 0.04 | 0.04 | 0.04 | 0.08 | 0.06 | 0.00 | 0.80 | 0.80 | 0.00 | 0.00 | 0.00 |
| 5860 | 0.00 | 0.00 | 0.00 | 0.12 | 0.07 | 0.11 | 0.10 | 0.38 | 0.55 | 0.92 | 0.80 | 0.00 | 0.00 |
| 5880 | 0.80 | 0.80 | 0.80 | 0.00 | 0.13 | 0.05 | 0.14 | 0.80 | 0.80 | 0.80 | 0.00 | 0.00 | 0.00 |
| 5900 | 0.80 | 0.80 | 0.80 | 0.80 | 0.80 | 0.80 | 0.80 | 0.80 | 0.80 | 0.80 | 0.00 | 0.00 | 0.00 |
| 5920 | 0.80 | 0.80 | 0.80 | 0.23 | 0.80 | 0.00 | 0.80 | 0.80 | 0.80 | 0.80 | 0.80 | 0.00 | 0.00 |
| 5940 | 0.80 | 0.80 | 0.80 | 0.00 | 0.00 | 0.00 | 0.00 | 0.00 | 0.80 | 0.80 | 0.00 | 0.00 | 0.00 |
| 5960 | 0.80 | 0.80 | 0.00 | 0.00 | 0.00 | 0.00 | 0.00 | 0.00 | 0.00 | 0.80 | 0.00 | 0.00 | 0.00 |
| 5980 | 0.80 | 0.80 | 0.80 | 0.80 | 0.00 | 0.18 | 0.09 | 0.80 | 0.80 | 0.80 | 0.80 | 0.17 | 0.00 |
| 6000 | 0.16 | 1.04 | 1.22 | 2.36 | 2.27 | 2.50 | 1.93 | 2.11 | 2.29 | 2.47 | 0.80 | 0.00 | 1.27 |
| 6020 | 0.80 | 1.06 | 1.31 | 2.27 | 1.80 | 2.05 | 2.50 | 2.50 | 2.50 | 2.50 | 0.80 | 1.05 | 1.36 |
| 6040 | 0.80 | 1.08 | 1.40 | 1.72 | 2.03 | 2.35 | 2.50 | 2.50 | 2.50 | 2.50 | 0.80 | 1.07 | 1.44 |
| 6060 | 0.80 | 1.10 | 1.49 | 1.87 | 2.26 | 2.50 | 2.50 | 2.50 | 2.50 | 2.50 | 0.80 | 1.09 | 1.53 |
| 6080 | 0.80 | 1.13 | 1.58 | 2.03 | 2.48 | 2.50 | 2.50 | 2.50 | 2.50 | 2.50 | 0.80 | 1.12 | 1.62 |
| 6100 | 0.19 | 0.80 | 1.04 | 1.22 | 2.16 | 1.58 | 1.76 | 2.32 | 2.50 | 2.50 | 0.24 | 1.14 | 1.05 |
| 6120 | 0.80 | 0.80 | 1.06 | 1.27 | 1.48 | 2.33 | 2.19 | 2.50 | 2.50 | 2.50 | 0.80 | 0.80 | 1.06 |
| 6140 | 0.80 | 0.80 | 1.07 | 1.31 | 1.55 | 1.79 | 2.03 | 2.50 | 2.50 | 2.50 | 0.80 | 0.80 | 1.08 |
| 6160 | 0.80 | 0.80 | 1.09 | 1.36 | 1.63 | 1.90 | 2.17 | 2.50 | 2.50 | 2.50 | 0.80 | 0.80 | 1.09 |

Fig. 14f¹

| | | | | | | | | | | | | | |
|---|---|---|---|---|---|---|---|---|---|---|---|---|---|
| 6180 | 0.80 | 0.80 | 1.10 | 1.40 | 1.71 | 2.01 | 2.31 | 2.33 | 2.50 | 2.50 | 0.80 | 0.80 | 1.11 |
| 6200 | 0.19 | 0.55 | 0.87 | 1.04 | 1.22 | 2.38 | 2.32 | 1.76 | 1.94 | 2.11 | 0.15 | 0.31 | 0.80 |
| 6220 | 0.13 | 0.00 | 0.80 | 1.05 | 1.25 | 1.45 | 1.64 | 2.24 | 2.50 | 2.50 | 0.80 | 0.80 | 0.80 |
| 6240 | 0.80 | 0.80 | 0.80 | 1.06 | 1.28 | 1.49 | 1.71 | 1.92 | 2.50 | 2.50 | 0.80 | 0.80 | 0.80 |
| 6260 | 0.80 | 0.80 | 0.80 | 1.07 | 1.30 | 1.54 | 1.77 | 2.39 | 2.44 | 2.50 | 0.80 | 0.80 | 0.80 |
| 6280 | 0.80 | 0.80 | 0.80 | 1.07 | 1.33 | 1.58 | 2.50 | 2.09 | 2.46 | 2.50 | 0.02 | 0.15 | 0.21 |
| 6300 | 0.12 | 0.37 | 0.61 | 0.87 | 1.05 | 2.33 | 1.40 | 1.58 | 1.76 | 1.94 | 0.00 | 0.12 | 0.29 |
| 6320 | 0.04 | 0.04 | 0.04 | 0.80 | 0.80 | 1.24 | 1.43 | 2.29 | 2.34 | 2.50 | 0.80 | 0.00 | 0.18 |
| 6340 | 0.00 | 0.10 | 0.07 | 0.30 | 0.80 | 0.80 | 1.45 | 1.66 | 2.34 | 2.50 | 0.80 | 0.80 | 0.80 |
| 6360 | 0.00 | 0.00 | 0.16 | 0.80 | 0.80 | 1.26 | 1.48 | 1.69 | 2.30 | 2.50 | 0.80 | 0.80 | 0.80 |
| 6380 | 0.80 | 0.80 | 0.80 | 0.80 | 1.05 | 1.28 | 1.50 | 2.05 | 2.36 | 2.42 | 0.01 | 0.11 | 0.08 |
| 6400 | 0.04 | 0.47 | 0.80 | 0.69 | 0.87 | 1.05 | 1.22 | 1.40 | 1.58 | 1.76 | 0.03 | 0.05 | 0.08 |
| 6420 | 0.00 | 0.04 | 0.15 | 0.35 | 0.74 | 0.80 | 1.23 | 1.41 | 1.62 | 2.50 | 0.07 | 0.00 | 0.06 |
| 6440 | 0.00 | 0.04 | 0.03 | 0.25 | 0.38 | 0.56 | 0.80 | 1.43 | 1.94 | 2.50 | 0.80 | 0.80 | 0.00 |
| 6460 | 0.00 | 0.00 | 0.10 | 0.27 | 0.47 | 0.80 | 0.48 | 1.44 | 1.40 | 2.35 | 0.80 | 0.04 | 0.80 |
| 6480 | 0.80 | 0.80 | 0.80 | 0.80 | 0.81 | 0.80 | 1.24 | 1.45 | 2.07 | 2.47 | 0.00 | 0.00 | 0.14 |
| 6500 | 0.02 | 0.35 | 0.48 | 0.51 | 0.69 | 0.87 | 1.05 | 1.22 | 1.40 | 1.58 | 0.00 | 0.04 | 0.02 |
| 6520 | 0.00 | 0.02 | 0.00 | 0.08 | 0.17 | 0.49 | 0.80 | 1.22 | 1.40 | 2.50 | 0.00 | 0.00 | 0.03 |
| 6540 | 0.04 | 0.04 | 0.04 | 0.06 | 0.21 | 0.27 | 0.45 | 0.80 | 1.40 | 1.59 | 0.00 | 0.00 | 0.00 |
| 6560 | 0.00 | 0.00 | 0.00 | 0.10 | 0.28 | 0.29 | 0.45 | 0.73 | 1.48 | 2.31 | 0.00 | 0.03 | 0.80 |
| 6580 | 0.80 | 0.80 | 0.07 | 0.12 | 0.31 | 0.39 | 0.62 | 1.22 | 1.23 | 2.15 | 0.80 | 0.80 | 0.08 |
| 6600 | 0.02 | 0.05 | 0.80 | 0.80 | 0.51 | 0.80 | 0.87 | 1.05 | 1.21 | 1.40 | 0.01 | 0.01 | 0.01 |
| 6620 | 0.00 | 0.00 | 0.09 | 0.05 | 0.11 | 0.24 | 0.38 | 0.80 | 1.20 | 1.39 | 0.00 | 0.00 | 0.04 |
| 6640 | 0.00 | 0.00 | 0.00 | 0.04 | 0.05 | 0.10 | 0.18 | 0.56 | 0.63 | 1.38 | 0.00 | 0.00 | 0.03 |
| 6660 | 0.00 | 0.00 | 0.06 | 0.00 | 0.04 | 0.14 | 0.23 | 0.51 | 0.98 | 1.99 | 0.00 | 0.00 | 0.00 |
| 6680 | 0.00 | 0.00 | 0.04 | 0.00 | 0.10 | 0.26 | 0.27 | 0.58 | 1.05 | 1.84 | 0.80 | 0.00 | 0.80 |
| 6700 | 0.00 | 0.11 | 0.80 | 0.80 | 0.80 | 0.80 | 0.80 | 0.80 | 1.02 | 1.23 | 0.00 | 0.04 | 0.08 |
| 6720 | 0.00 | 0.03 | 0.00 | 0.09 | 0.02 | 0.07 | 0.30 | 0.80 | 0.80 | 1.20 | 0.00 | 0.03 | 0.02 |
| 6740 | 0.00 | 0.00 | 0.01 | 0.03 | 0.07 | 0.05 | 0.14 | 0.11 | 0.80 | 1.18 | 0.00 | 0.00 | 0.04 |

Fig. 14g

| | | | | | | | | | | | | | |
|---|---|---|---|---|---|---|---|---|---|---|---|---|---|
| 6760 | 0.00 | 0.00 | 0.00 | 0.02 | 0.03 | 0.04 | 0.09 | 0.15 | 0.26 | 0.64 | 1.16 | 0.00 | 0.00 | 0.00 |
| 6780 | 0.00 | 0.00 | 0.00 | 0.03 | 0.03 | 0.02 | 0.18 | 0.24 | 0.31 | 0.65 | 1.32 | 1.00 | 0.00 | 0.00 |
| 6800 | 0.00 | 0.03 | 0.00 | 0.00 | 0.80 | 0.80 | 0.80 | 0.80 | 0.80 | 0.80 | 1.05 | 0.00 | 0.04 | 0.05 |
| 6820 | 0.00 | 0.00 | 0.00 | 0.00 | 0.09 | 0.09 | 0.14 | 0.11 | 0.80 | 0.80 | 1.02 | 0.00 | 0.00 | 0.04 |
| 6840 | 0.00 | 0.00 | 0.00 | 0.02 | 0.02 | 0.02 | 0.07 | 0.12 | 0.11 | 0.80 | 0.99 | 0.00 | 0.00 | 0.02 |
| 6860 | 0.80 | 0.00 | 0.00 | 0.00 | 0.04 | 0.00 | 0.03 | 0.10 | 0.06 | 0.32 | 0.80 | 0.80 | 0.00 | 0.00 |
| 6880 | 0.80 | 0.80 | 0.00 | 0.80 | 0.00 | 0.80 | 0.14 | 0.09 | 0.17 | 0.21 | 0.70 | 0.00 | 0.00 | 0.00 |
| 6900 | 0.80 | 0.00 | 0.13 | 0.00 | 0.00 | 0.80 | 0.80 | 0.80 | 0.80 | 0.80 | 0.80 | 0.80 | 0.00 | 0.00 |
| 6920 | 0.80 | 0.13 | 0.00 | 0.00 | 0.00 | 0.80 | 0.23 | 0.80 | 0.80 | 0.80 | 0.80 | 0.80 | 0.00 | 0.00 |
| 6940 | 0.80 | 0.00 | 0.00 | 0.00 | 0.00 | 0.00 | 0.00 | 0.80 | 0.80 | 0.80 | 0.80 | 0.80 | 0.80 | 0.00 |
| 6960 | 0.80 | 0.80 | 0.00 | 0.00 | 0.00 | 0.00 | 0.05 | 0.09 | 0.00 | 0.15 | 0.72 | 0.82 | 1.05 | 1.28 |
| 6980 | 0.85 | 1.04 | 1.24 | 1.43 | 1.63 | 1.82 | 2.02 | 2.21 | 2.41 | 2.50 | 0.76 | 1.06 | 1.37 |
| 7000 | 0.79 | 1.06 | 1.32 | 1.59 | 1.86 | 2.12 | 2.39 | 2.50 | 2.50 | 2.50 | 0.80 | 1.08 | 1.45 |
| 7020 | 0.80 | 1.07 | 1.41 | 1.75 | 2.09 | 2.42 | 2.50 | 2.50 | 2.50 | 2.50 | 0.80 | 1.09 | 1.54 |
| 7040 | 0.80 | 1.09 | 1.50 | 1.90 | 2.31 | 2.50 | 2.50 | 2.50 | 2.50 | 2.50 | 0.80 | 1.11 | 1.62 |
| 7060 | 0.80 | 1.10 | 1.58 | 2.06 | 2.50 | 2.50 | 2.50 | 2.50 | 2.25 | 2.44 | 0.80 | 0.80 | 1.08 |
| 7080 | 0.80 | 0.88 | 1.08 | 1.27 | 1.47 | 1.76 | 1.86 | 2.05 | 2.25 | 2.50 | 0.80 | 0.80 | 1.08 |
| 7100 | 0.33 | 0.80 | 1.08 | 1.30 | 1.53 | 1.85 | 2.50 | 2.50 | 2.50 | 2.50 | 0.80 | 0.80 | 1.08 |
| 7120 | 0.80 | 0.80 | 1.08 | 1.34 | 1.59 | 1.94 | 2.23 | 2.50 | 2.50 | 2.50 | 0.80 | 0.80 | 1.08 |
| 7140 | 0.80 | 0.80 | 1.09 | 1.37 | 1.66 | 2.04 | 2.35 | 2.50 | 2.50 | 2.50 | 0.80 | 0.80 | 1.09 |
| 7160 | 0.80 | 0.80 | 1.09 | 1.40 | 1.72 | 1.50 | 1.69 | 2.27 | 2.50 | 2.50 | 0.80 | 0.80 | 1.09 |
| 7180 | 0.80 | 0.80 | 0.91 | 1.11 | 1.30 | 2.38 | 2.27 | 2.50 | 2.50 | 1.00 | 0.80 | 0.22 | 0.90 |
| 7200 | 0.06 | 0.80 | 0.89 | 1.10 | 1.31 | 2.38 | 2.35 | 2.50 | 2.50 | 1.00 | 0.00 | 0.22 | 0.90 |
| 7220 | 0.80 | 0.80 | 0.80 | 1.09 | 1.32 | 1.55 | 1.82 | 2.06 | 2.50 | 2.50 | 2.50 | 0.80 | 0.80 |
| 7240 | 0.80 | 0.80 | 0.84 | 1.09 | 1.33 | 1.58 | 1.86 | 2.31 | 2.50 | 2.50 | 2.46 | 0.80 | 0.83 |
| 7260 | 0.80 | 0.80 | 0.82 | 1.08 | 1.34 | 1.60 | 1.86 | 2.06 | 2.50 | 2.50 | 2.50 | 0.80 | 0.80 |
| 7280 | 0.80 | 0.80 | 0.75 | 0.95 | 1.14 | 1.34 | 1.53 | 1.73 | 1.92 | 2.12 | 0.04 | 0.16 | 0.16 |
| 7300 | 0.08 | 0.18 | | | | | | | | | | | |

Fig. 14g¹

| | | | | | | | | | | | | | |
|---|---|---|---|---|---|---|---|---|---|---|---|---|---|
| 7320 | 0.08 | 0.30 | 0.80 | 0.92 | 1.12 | 1.33 | 1.53 | 2.31 | 2.44 | 2.50 | 0.00 | 0.00 | 0.31 |
| 7340 | 0.00 | 0.14 | 0.80 | 0.89 | 1.10 | 1.32 | 1.53 | 2.25 | 2.18 | 2.50 | 0.80 | 0.80 | 0.80 |
| 7360 | 0.80 | 0.80 | 0.80 | 0.86 | 1.09 | 1.31 | 1.53 | 1.76 | 2.41 | 2.46 | 0.80 | 0.80 | 0.80 |
| 7380 | 0.80 | 0.80 | 0.80 | 0.83 | 1.07 | 1.30 | 1.53 | 2.38 | 2.24 | 2.48 | 0.80 | 0.80 | 0.80 |
| 7400 | 0.05 | 0.26 | 0.59 | 0.79 | 0.98 | 1.18 | 1.37 | 1.57 | 1.76 | 1.96 | 0.02 | 0.16 | 0.52 |
| 7420 | 0.00 | 0.04 | 0.16 | 0.45 | 0.80 | 1.15 | 1.35 | 2.30 | 2.23 | 2.50 | 0.00 | 0.05 | 0.09 |
| 7440 | 0.00 | 0.00 | 0.26 | 0.33 | 0.80 | 0.80 | 1.32 | 1.53 | 2.23 | 2.44 | 0.00 | 0.00 | 0.00 |
| 7460 | 0.00 | 0.00 | 0.00 | 0.80 | 0.80 | 0.80 | 1.30 | 1.51 | 2.27 | 2.41 | 0.80 | 0.80 | 0.80 |
| 7480 | 0.80 | 0.80 | 0.80 | 0.80 | 0.80 | 0.80 | 1.27 | 1.49 | 2.04 | 2.46 | 0.80 | 0.80 | 0.80 |
| 7500 | 0.06 | 0.43 | 0.80 | 0.80 | 0.82 | 1.06 | 1.21 | 1.40 | 1.60 | 1.79 | 0.01 | 0.04 | 0.10 |
| 7520 | 0.02 | 0.06 | 0.07 | 0.29 | 0.36 | 1.01 | 1.17 | 1.37 | 2.21 | 2.50 | 0.00 | 0.00 | 0.07 |
| 7540 | 0.00 | 0.06 | 0.05 | 0.21 | 0.19 | 0.97 | 0.69 | 1.33 | 2.11 | 2.43 | 0.00 | 0.00 | 0.00 |
| 7560 | 0.00 | 0.00 | 0.00 | 0.06 | 0.16 | 0.45 | 0.48 | 1.29 | 1.00 | 2.47 | 0.00 | 0.00 | 0.00 |
| 7580 | 0.80 | 0.80 | 0.80 | 0.00 | 0.09 | 0.23 | 0.80 | 1.25 | 1.70 | 2.36 | 0.80 | 0.80 | 0.80 |
| 7600 | 0.00 | 0.22 | 0.00 | 1.00 | 0.80 | 0.80 | 1.05 | 1.24 | 1.44 | 1.63 | 0.00 | 0.02 | 0.16 |
| 7620 | 0.00 | 0.04 | 0.04 | 0.22 | 0.11 | 0.85 | 0.54 | 1.19 | 2.36 | 2.50 | 0.01 | 0.00 | 0.03 |
| 7640 | 0.00 | 0.00 | 0.00 | 0.08 | 0.07 | 0.58 | 0.45 | 0.80 | 1.33 | 2.35 | 0.00 | 0.00 | 0.00 |
| 7660 | 0.00 | 0.00 | 0.04 | 0.06 | 0.05 | 0.16 | 0.16 | 0.48 | 1.28 | 2.32 | 0.00 | 0.00 | 0.00 |
| 7680 | 0.00 | 0.00 | 0.00 | 0.04 | 0.17 | 0.11 | 0.33 | 0.71 | 1.23 | 2.24 | 0.00 | 0.00 | 0.00 |
| 7700 | 0.00 | 0.13 | 0.07 | 0.80 | 0.49 | 0.13 | 0.88 | 1.08 | 1.27 | 1.47 | 0.00 | 0.80 | 0.06 |
| 7720 | 0.00 | 0.01 | 0.02 | 0.11 | 0.13 | 0.69 | 0.80 | 0.80 | 1.21 | 1.41 | 0.80 | 0.00 | 0.00 |
| 7740 | 0.00 | 0.00 | 0.01 | 0.00 | 0.06 | 0.16 | 0.37 | 0.31 | 0.80 | 1.34 | 0.00 | 0.01 | 0.01 |
| 7760 | 0.00 | 0.00 | 0.03 | 0.02 | 0.02 | 0.21 | 0.14 | 0.18 | 0.63 | 2.05 | 0.00 | 0.00 | 0.00 |
| 7780 | 0.00 | 0.00 | 0.00 | 0.14 | 0.02 | 0.10 | 0.20 | 0.31 | 0.57 | 1.60 | 0.00 | 0.00 | 0.00 |
| 7800 | 0.09 | 0.17 | 0.00 | 0.05 | 0.33 | 0.11 | 0.72 | 0.92 | 1.11 | 1.31 | 0.80 | 0.80 | 0.00 |
| 7820 | 0.00 | 0.00 | 0.00 | 0.01 | 0.05 | 0.53 | 0.80 | 0.85 | 1.04 | 1.23 | 0.00 | 0.01 | 0.01 |
| 7840 | 0.00 | 0.00 | 0.04 | 0.01 | 0.06 | 0.14 | 0.15 | 0.30 | 0.36 | 1.16 | 0.00 | 0.00 | 0.00 |
| 7860 | 0.00 | 0.00 | 0.00 | 0.01 | 0.02 | 0.08 | 0.10 | 0.10 | 0.30 | 1.09 | 0.00 | 0.00 | 0.00 |

Fig. 14h

| | | | | | | | | | | | | | |
|---|---|---|---|---|---|---|---|---|---|---|---|---|---|
| 7880 | 0.00 | 0.00 | 0.00 | 0.02 | 0.00 | 0.04 | 0.06 | 0.16 | 0.28 | 1.35 | 0.80 | 0.00 | 0.00 |
| 7900 | 0.80 | 0.80 | 0.80 | 0.80 | 0.80 | 0.80 | 0.80 | 0.80 | 0.95 | 1.14 | 0.00 | 0.00 | 0.00 |
| 7920 | 0.00 | 0.00 | 0.00 | 0.00 | 0.00 | 0.16 | 0.17 | 0.80 | 0.87 | 1.06 | 0.00 | 0.00 | 0.00 |
| 7940 | 0.00 | 0.00 | 0.00 | 0.00 | 0.06 | 0.11 | 0.07 | 0.15 | 0.80 | 0.98 | 0.00 | 0.00 | 0.00 |
| 7960 | 0.00 | 0.00 | 0.00 | 0.00 | 0.02 | 0.02 | 0.02 | 0.00 | 0.19 | 0.80 | 0.80 | 0.00 | 0.00 |
| 7980 | 0.00 | 0.00 | 0.00 | 1.33 | 0.00 | 0.02 | 0.09 | 0.12 | 0.11 | 0.95 | 0.71 | 0.80 | 0.00 |
| 8000 | 0.80 | 0.93 | 1.13 | 1.66 | 1.53 | 1.73 | 1.93 | 2.12 | 2.32 | 2.50 | 0.66 | 0.97 | 1.23 |
| 8020 | 0.73 | 1.01 | 1.34 | 2.00 | 1.99 | 2.32 | 2.50 | 2.50 | 2.50 | 2.50 | 0.61 | 1.05 | 1.44 |
| 8040 | 0.68 | 1.09 | 1.54 | 2.33 | 2.45 | 2.50 | 2.50 | 2.50 | 2.50 | 2.50 | 0.55 | 1.13 | 1.64 |
| 8060 | 0.63 | 1.16 | 1.75 | 2.50 | 2.50 | 2.50 | 2.50 | 2.50 | 2.50 | 2.50 | 0.50 | 1.20 | 1.85 |
| 8080 | 0.58 | 1.24 | 1.95 | 2.50 | 2.50 | 2.50 | 2.50 | 2.50 | 2.50 | 2.50 | 0.80 | 1.28 | 2.05 |
| 8100 | 0.53 | 0.80 | 0.99 | 1.19 | 1.39 | 1.59 | 1.78 | 1.98 | 2.18 | 2.38 | 0.52 | 0.79 | 1.02 |
| 8120 | 0.80 | 0.80 | 1.05 | 1.30 | 1.56 | 1.81 | 2.06 | 2.32 | 2.50 | 2.50 | 0.47 | 0.80 | 1.08 |
| 8140 | 0.54 | 0.80 | 1.11 | 1.42 | 1.73 | 2.04 | 2.35 | 2.50 | 2.50 | 2.50 | 0.41 | 0.81 | 1.14 |
| 8160 | 0.80 | 0.80 | 1.17 | 1.53 | 1.90 | 2.26 | 2.50 | 2.50 | 2.50 | 2.50 | 0.36 | 0.81 | 1.20 |
| 8180 | 0.44 | 0.80 | 1.23 | 1.65 | 2.07 | 2.49 | 2.50 | 2.50 | 2.50 | 2.24 | 0.80 | 0.80 | 1.26 |
| 8200 | 0.39 | 0.81 | 0.80 | 1.05 | 1.25 | 1.44 | 1.64 | 1.84 | 2.04 | 2.50 | 0.80 | 0.80 | 0.80 |
| 8220 | 0.80 | 0.80 | 0.80 | 1.09 | 1.32 | 1.55 | 1.78 | 2.01 | 2.50 | 2.50 | 0.80 | 0.80 | 0.80 |
| 8240 | 0.80 | 0.80 | 0.80 | 0.80 | 1.39 | 1.65 | 1.91 | 2.27 | 2.39 | 2.50 | 0.80 | 0.80 | 0.80 |
| 8260 | 0.80 | 0.80 | 0.80 | 0.80 | 1.46 | 1.76 | 2.05 | 2.34 | 2.40 | 2.10 | 0.80 | 0.80 | 0.80 |
| 8280 | 0.80 | 0.80 | 0.80 | 1.21 | 1.54 | 1.86 | 2.18 | 2.50 | 2.50 | 2.50 | 0.00 | 0.80 | 0.80 |
| 8300 | 0.80 | 0.80 | 0.71 | 0.91 | 1.11 | 1.30 | 1.50 | 1.70 | 1.90 | 2.50 | 0.80 | 0.80 | 0.80 |
| 8320 | 0.00 | 0.21 | 0.80 | 0.80 | 1.13 | 1.35 | 1.56 | 2.40 | 2.50 | 2.50 | 0.80 | 0.80 | 0.80 |
| 8340 | 0.80 | 0.18 | 0.80 | 0.92 | 1.15 | 1.39 | 1.63 | 1.86 | 2.39 | 1.96 | 0.80 | 0.80 | 0.80 |
| 8360 | 0.80 | 0.80 | 0.80 | 0.80 | 1.18 | 1.43 | 1.69 | 2.50 | 2.40 | 2.50 | 0.80 | 0.80 | 0.80 |
| 8380 | 0.80 | 0.80 | 0.80 | 0.77 | 1.20 | 1.47 | 1.75 | 2.02 | 2.50 | 2.50 | 0.04 | 0.80 | 0.80 |
| 8400 | 0.80 | 0.80 | 0.80 | 0.80 | 0.96 | 1.16 | 1.36 | 1.56 | 1.76 | 1.96 | 0.00 | 0.16 | 0.33 |
| 8420 | 0.00 | 0.34 | 0.80 | 0.80 | 0.96 | 1.17 | 1.38 | 2.35 | 2.50 | 2.50 | 0.80 | 0.80 | 0.00 |
| 8440 | 0.80 | 0.00 | 0.00 | 0.80 | 0.95 | 1.18 | 1.40 | 1.62 | 2.42 | 2.50 | 0.80 | 0.80 | 0.80 |

Fig. 14h'

| | | | | | | | | | | | | | |
|---|---|---|---|---|---|---|---|---|---|---|---|---|---|
| 8460 | 0.80 | 0.80 | 0.80 | 0.80 | 0.95 | 1.18 | 2.29 | 2.32 | 2.32 | 2.50 | 0.80 | 0.80 | 0.80 |
| 8480 | 0.80 | 0.80 | 0.80 | 0.80 | 0.94 | 1.19 | 1.43 | 1.68 | 2.50 | 2.48 | 0.80 | 0.80 | 0.80 |
| 8500 | 0.00 | 0.09 | 0.80 | 0.63 | 0.82 | 1.02 | 1.22 | 1.42 | 1.62 | 1.82 | 0.00 | 0.00 | 0.06 |
| 8520 | 0.00 | 0.00 | 0.09 | 0.28 | 0.80 | 1.00 | 1.21 | 1.41 | 1.62 | 2.50 | 0.00 | 0.00 | 0.28 |
| 8540 | 0.00 | 0.00 | 0.10 | 0.11 | 0.38 | 0.19 | 1.20 | 1.41 | 2.31 | 2.50 | 0.80 | 0.00 | 0.10 |
| 8560 | 0.80 | 0.00 | 0.00 | 0.09 | 0.00 | 0.80 | 1.19 | 1.40 | 1.62 | 2.47 | 0.00 | 0.00 | 0.00 |
| 8580 | 0.80 | 0.80 | 0.80 | 0.80 | 0.80 | 0.80 | 1.17 | 1.40 | 1.62 | 2.42 | 0.80 | 0.80 | 0.80 |
| 8600 | 0.00 | 0.14 | 0.34 | 0.48 | 0.68 | 0.88 | 1.08 | 1.28 | 1.48 | 1.68 | 0.00 | 0.00 | 0.14 |
| 8620 | 0.00 | 0.02 | 0.03 | 0.00 | 0.16 | 0.47 | 1.05 | 1.25 | 2.50 | 2.50 | 0.00 | 0.02 | 0.06 |
| 8640 | 0.00 | 0.00 | 0.03 | 0.03 | 0.04 | 0.14 | 0.80 | 1.22 | 2.05 | 2.50 | 0.00 | 0.00 | 0.03 |
| 8660 | 0.00 | 0.00 | 0.00 | 0.09 | 0.11 | 0.18 | 0.16 | 0.80 | 1.40 | 2.37 | 0.00 | 0.00 | 0.00 |
| 8680 | 0.80 | 0.00 | 0.00 | 0.07 | 0.07 | 0.33 | 0.39 | 0.80 | 1.52 | 2.36 | 0.80 | 0.80 | 0.06 |
| 8700 | 0.00 | 0.00 | 0.00 | 0.80 | 0.54 | 0.74 | 0.94 | 1.14 | 1.34 | 1.53 | 0.00 | 0.00 | 0.03 |
| 8720 | 0.00 | 0.00 | 0.00 | 0.12 | 0.12 | 0.80 | 0.80 | 1.09 | 2.35 | 2.50 | 0.00 | 0.00 | 0.00 |
| 8740 | 0.00 | 0.02 | 0.00 | 0.02 | 0.02 | 0.15 | 0.41 | 0.65 | 1.24 | 2.50 | 0.80 | 0.00 | 0.06 |
| 8760 | 0.00 | 0.00 | 0.00 | 0.07 | 0.08 | 0.02 | 0.32 | 0.55 | 0.97 | 2.29 | 0.00 | 0.00 | 0.03 |
| 8780 | 0.00 | 0.02 | 0.03 | 0.05 | 0.10 | 0.08 | 0.15 | 0.32 | 0.75 | 2.28 | 0.00 | 0.00 | 0.00 |
| 8800 | 0.00 | 0.00 | 0.80 | 0.80 | 0.80 | 0.80 | 0.80 | 1.00 | 1.20 | 1.39 | 0.80 | 0.80 | 0.00 |
| 8820 | 0.00 | 0.00 | 0.00 | 0.03 | 0.00 | 0.33 | 0.80 | 0.94 | 1.13 | 1.33 | 0.00 | 0.00 | 0.04 |
| 8840 | 0.00 | 0.05 | 0.00 | 0.01 | 0.01 | 0.08 | 0.34 | 0.37 | 0.80 | 2.36 | 0.00 | 0.00 | 0.00 |
| 8860 | 0.00 | 0.00 | 0.00 | 0.03 | 0.03 | 0.04 | 0.04 | 0.14 | 0.58 | 2.18 | 0.80 | 0.00 | 0.00 |
| 8880 | 0.00 | 0.00 | 0.80 | 0.80 | 0.26 | 0.06 | 0.08 | 0.17 | 0.38 | 1.91 | 0.00 | 0.00 | 0.00 |
| 8900 | 0.00 | 0.00 | 0.00 | 0.06 | 0.07 | 0.46 | 0.66 | 0.86 | 1.05 | 1.25 | 0.00 | 0.00 | 0.04 |
| 8920 | 0.00 | 0.00 | 0.00 | 0.00 | 0.02 | 0.10 | 0.59 | 0.78 | 0.98 | 1.17 | 0.00 | 0.00 | 0.00 |
| 8940 | 0.00 | 0.00 | 0.01 | 0.00 | 0.03 | 0.00 | 0.06 | 0.21 | 0.80 | 1.09 | 0.80 | 0.00 | 0.00 |
| 8960 | 0.00 | 0.00 | 0.00 | 0.00 | 0.01 | 0.03 | 0.05 | 0.10 | 0.17 | 1.02 | 0.00 | 0.00 | 0.00 |
| 8980 | 0.00 | 0.00 | 0.00 | 0.00 | 0.03 | 0.04 | 0.02 | 0.04 | 0.15 | 1.10 | 0.80 | 0.00 | 0.00 |
| 9000 | 0.98 | 1.14 | 1.30 | 1.47 | 1.63 | 1.79 | 1.95 | 2.11 | 2.28 | 2.44 | 1.02 | 1.19 | 1.36 |
| 9020 | 1.06 | 1.24 | 1.41 | 1.59 | 1.76 | 1.94 | 2.11 | 2.29 | 2.46 | 2.50 | 1.10 | 1.28 | 1.46 |

Fig. 14i

| | | | | | | | | | | | | | |
|---|---|---|---|---|---|---|---|---|---|---|---|---|---|
| 9040 | 1.14 | 1.33 | 1.52 | 1.71 | 1.90 | 2.08 | 2.27 | 2.46 | 2.50 | 2.50 | 1.18 | 1.38 | 1.57 |
| 9060 | 1.22 | 1.42 | 1.62 | 1.83 | 2.03 | 2.23 | 2.43 | 2.50 | 2.50 | 2.50 | 1.26 | 1.47 | 1.68 |
| 9080 | 1.30 | 1.52 | 1.73 | 1.95 | 2.16 | 2.38 | 2.50 | 2.50 | 2.50 | 2.50 | 1.34 | 1.56 | 1.78 |
| 9100 | 0.75 | 0.91 | 1.07 | 1.24 | 1.40 | 1.56 | 1.72 | 1.88 | 2.05 | 2.21 | 0.79 | 0.96 | 1.12 |
| 9120 | 0.83 | 1.00 | 1.18 | 1.35 | 1.52 | 1.69 | 1.87 | 2.04 | 2.21 | 2.38 | 0.87 | 1.05 | 1.23 |
| 9140 | 0.91 | 1.09 | 1.28 | 1.46 | 1.64 | 1.83 | 2.01 | 2.19 | 2.38 | 2.50 | 0.95 | 1.14 | 1.33 |
| 9160 | 0.99 | 1.18 | 1.38 | 1.57 | 1.76 | 1.96 | 2.15 | 2.35 | 2.50 | 2.50 | 1.03 | 1.23 | 1.43 |
| 9180 | 1.07 | 1.27 | 1.48 | 1.68 | 1.89 | 2.09 | 2.30 | 2.50 | 2.50 | 2.50 | 1.11 | 1.32 | 1.53 |
| 9200 | 0.52 | 0.68 | 0.84 | 1.01 | 1.17 | 1.33 | 1.49 | 1.65 | 1.82 | 1.98 | 0.56 | 0.73 | 0.89 |
| 9220 | 0.60 | 0.77 | 0.94 | 1.12 | 1.29 | 1.46 | 1.63 | 1.80 | 1.97 | 2.15 | 0.64 | 0.82 | 0.99 |
| 9240 | 0.68 | 0.86 | 1.04 | 1.22 | 1.41 | 1.59 | 1.77 | 1.95 | 2.13 | 2.50 | 0.72 | 0.91 | 1.09 |
| 9260 | 0.76 | 0.95 | 1.14 | 1.33 | 1.52 | 1.71 | 1.91 | 2.10 | 2.29 | 2.50 | 0.80 | 1.00 | 1.19 |
| 9280 | 0.84 | 1.04 | 1.24 | 1.44 | 1.64 | 1.84 | 2.04 | 2.24 | 2.44 | 2.50 | 0.88 | 1.09 | 1.29 |
| 9300 | 0.29 | 0.45 | 0.61 | 0.78 | 0.94 | 1.10 | 1.26 | 1.42 | 1.59 | 1.75 | 0.33 | 0.50 | 0.66 |
| 9320 | 0.37 | 0.54 | 0.71 | 0.88 | 1.06 | 1.23 | 1.40 | 1.57 | 2.33 | 2.50 | 0.41 | 0.59 | 0.76 |
| 9340 | 0.45 | 0.63 | 0.81 | 0.99 | 1.17 | 1.35 | 1.53 | 1.71 | 2.05 | 2.50 | 0.49 | 0.68 | 0.86 |
| 9360 | 0.53 | 0.72 | 0.91 | 1.10 | 1.29 | 1.48 | 1.67 | 1.86 | 2.20 | 2.50 | 0.57 | 0.76 | 0.96 |
| 9380 | 0.61 | 0.81 | 1.01 | 1.21 | 1.40 | 1.60 | 1.80 | 2.00 | 2.50 | 2.50 | 0.65 | 0.85 | 1.06 |
| 9400 | 0.00 | 0.22 | 0.39 | 0.55 | 0.71 | 0.87 | 1.03 | 1.19 | 1.36 | 1.52 | 0.10 | 0.27 | 0.43 |
| 9420 | 0.14 | 0.31 | 0.48 | 0.65 | 0.82 | 1.00 | 1.17 | 1.34 | 2.50 | 2.50 | 0.18 | 0.36 | 0.53 |
| 9440 | 0.22 | 0.40 | 0.58 | 0.76 | 0.94 | 1.12 | 1.30 | 1.48 | 2.50 | 2.50 | 0.26 | 0.44 | 0.63 |
| 9460 | 0.30 | 0.49 | 0.68 | 0.87 | 1.05 | 1.24 | 1.43 | 1.62 | 1.81 | 2.45 | 0.34 | 0.53 | 0.73 |
| 9480 | 0.38 | 0.58 | 0.78 | 0.97 | 1.17 | 1.37 | 1.57 | 1.76 | 2.37 | 2.50 | 0.42 | 0.62 | 0.82 |
| 9500 | 0.00 | 0.15 | 0.16 | 0.32 | 0.48 | 0.64 | 0.80 | 0.97 | 1.13 | 1.29 | 0.00 | 0.13 | 0.20 |
| 9520 | -0.09 | 0.08 | 0.25 | 0.42 | 0.59 | 0.76 | 0.94 | 1.11 | 1.28 | 1.45 | 0.00 | 0.00 | 0.00 |
| 9540 | 0.00 | 0.00 | 0.35 | 0.53 | 0.71 | 0.89 | 1.07 | 1.25 | 2.50 | 2.42 | 0.03 | 0.21 | 0.40 |
| 9560 | 0.07 | 0.26 | 0.45 | 0.63 | 0.82 | 1.01 | 1.20 | 1.39 | 2.32 | 2.50 | 0.11 | 0.30 | 0.50 |
| 9580 | 0.15 | 0.35 | 0.54 | 0.74 | 0.94 | 1.13 | 1.33 | 2.29 | 2.38 | 2.48 | 0.19 | 0.39 | 0.59 |
| 9600 | 0.00 | -0.24 | -0.07 | 0.09 | 0.25 | 0.41 | 0.57 | 0.74 | 0.90 | 1.06 | 0.00 | 0.00 | 0.00 |

Fig. 14i'

| | | | | | | | | | | | | | |
|---|---|---|---|---|---|---|---|---|---|---|---|---|---|
| 9620 | 0.00 | 0.00 | 0.00 | 0.00 | 0.21 | 0.53 | 0.70 | 0.87 | 2.50 | 2.50 | 0.00 | 0.00 | 0.07 |
| 9640 | 0.00 | 0.00 | 0.00 | 0.00 | 0.00 | 0.00 | 0.84 | 1.01 | 2.13 | 2.44 | 0.00 | 0.00 | 0.00 |
| 9660 | 0.00 | 0.00 | 0.00 | 0.16 | 0.17 | 0.00 | 0.97 | 1.15 | 1.34 | 2.50 | 0.00 | 0.07 | 0.26 |
| 9680 | 0.00 | 0.12 | 0.31 | 0.00 | 0.00 | 0.00 | 1.10 | 1.29 | 1.49 | 2.46 | 0.00 | 0.16 | 0.36 |
| 9700 | 0.00 | 0.00 | 0.00 | -0.14 | 0.02 | 0.18 | 0.34 | 0.51 | 0.67 | 0.83 | 0.00 | 0.00 | 0.00 |
| 9720 | 0.00 | 0.00 | 0.00 | 0.00 | 0.00 | 0.30 | 0.47 | 0.64 | 0.81 | 0.99 | 0.00 | 0.00 | 0.00 |
| 9740 | 0.00 | 0.00 | 0.00 | 0.00 | 0.12 | 0.16 | 0.28 | 0.78 | 2.13 | 2.50 | 0.00 | 0.00 | 0.00 |
| 9760 | 0.80 | 0.13 | 0.00 | 0.00 | 0.06 | 0.04 | 0.16 | 0.50 | 1.11 | 2.44 | 0.00 | 0.00 | 0.13 |
| 9780 | 0.00 | 0.00 | 0.04 | 0.00 | 0.00 | 0.04 | 0.19 | 0.40 | 1.19 | 2.44 | 0.00 | 0.00 | 0.00 |
| 9800 | 0.00 | 0.00 | 0.04 | 0.00 | 0.00 | 0.00 | 0.11 | 0.28 | 0.44 | 0.60 | 0.00 | 0.00 | 0.00 |
| 9820 | 0.00 | 0.00 | 0.00 | 0.00 | 0.03 | 0.21 | 0.17 | 0.41 | 0.58 | 0.75 | 0.00 | 0.00 | 0.00 |
| 9840 | 0.00 | 0.00 | 0.00 | 0.00 | 0.05 | 0.21 | 0.17 | 0.55 | 0.73 | 0.91 | 0.00 | 0.00 | 0.00 |
| 9860 | 0.00 | 0.00 | 0.00 | 0.00 | 0.00 | 0.04 | 0.10 | 0.11 | 0.65 | 2.35 | 0.00 | 0.00 | 0.00 |
| 9880 | 0.00 | 0.00 | 0.00 | 0.00 | 0.00 | 0.04 | 0.04 | 0.10 | 0.46 | 2.28 | 0.00 | 0.00 | 0.00 |
| 9900 | 0.00 | 0.00 | 0.00 | 0.00 | 0.03 | 0.00 | 0.00 | 0.05 | 0.21 | 0.37 | 0.00 | 0.00 | 0.00 |
| 9920 | 0.00 | 0.00 | 0.00 | 0.01 | 0.00 | 0.02 | 0.01 | 0.18 | 0.35 | 0.52 | 0.00 | 0.00 | 0.00 |
| 9940 | 0.00 | 0.01 | 0.01 | 0.00 | 0.03 | 0.02 | 0.03 | 0.26 | 0.50 | 0.68 | 0.00 | 0.00 | 0.00 |
| 9960 | 0.00 | 0.00 | 0.00 | 0.00 | 0.00 | 0.00 | 0.03 | 0.13 | 0.50 | 2.23 | 0.00 | 0.00 | 0.00 |
| 9980 | 0.00 | 0.00 | 0.00 | 0.01 | 0.01 | 0.01 | 0.03 | 0.07 | 0.16 | 1.94 | 0.00 | 0.00 | 0.00 |

Fig. 14j

| 13 | 14 | 15 | 16 | 17 | 18 | 19 |
|---|---|---|---|---|---|---|
| 2.14 | 1.97 | 2.08 | 2.26 | 2.42 | 2.43 | 2.50 |
| 2.39 | 2.37 | 2.39 | 2.34 | 2.41 | 2.45 | 2.50 |
| 2.46 | 2.48 | 2.50 | 2.49 | 2.45 | 2.49 | 2.50 |
| 2.50 | 2.50 | 2.47 | 2.49 | 2.48 | 2.49 | 2.50 |
| 2.50 | 2.50 | 2.50 | 2.50 | 2.50 | 2.50 | 2.50 |
| 0.95 | 0.97 | 1.15 | 1.63 | 1.97 | 2.32 | 2.50 |
| 1.85 | 2.06 | 1.94 | 2.18 | 2.21 | 2.39 | 2.41 |
| 2.40 | 2.29 | 2.46 | 2.34 | 2.45 | 2.42 | 2.50 |
| 2.47 | 2.44 | 2.43 | 2.45 | 2.49 | 2.47 | 2.49 |
| 2.50 | 2.50 | 2.50 | 2.50 | 2.48 | 2.50 | 2.50 |
| 0.62 | 0.48 | 0.58 | 0.80 | 1.60 | 2.35 | 2.50 |
| 1.04 | 1.28 | 1.52 | 1.76 | 1.96 | 2.03 | 2.50 |
| 1.85 | 2.19 | 2.29 | 2.11 | 2.21 | 2.30 | 2.50 |
| 2.20 | 2.43 | 2.39 | 2.45 | 2.37 | 2.48 | 2.48 |
| 2.50 | 2.50 | 2.50 | 2.50 | 2.47 | 2.49 | 2.50 |
| 0.18 | 0.24 | 0.36 | 1.17 | 1.35 | 1.52 | 1.69 |
| 0.80 | 1.23 | 1.37 | 1.52 | 1.66 | 1.80 | 1.94 |
| 1.53 | 1.64 | 2.02 | 1.86 | 2.43 | 2.33 | 2.50 |
| 1.97 | 2.50 | 2.39 | 2.46 | 2.39 | 2.44 | 2.55 |
| 2.41 | 2.46 | 2.50 | 2.50 | 2.45 | 2.50 | 2.50 |
| 0.12 | 0.00 | 0.80 | 0.80 | 1.01 | 1.18 | 1.36 |
| 0.80 | 0.80 | 0.80 | 1.19 | 1.33 | 1.48 | 1.62 |
| 1.20 | 1.32 | 1.43 | 1.55 | 1.66 | 1.78 | 1.89 |
| 1.65 | 2.50 | 2.41 | 2.42 | 2.44 | 2.26 | 2.50 |
| 2.10 | 2.15 | 2.21 | 2.26 | 2.50 | 2.50 | 2.50 |
| 0.80 | 0.80 | 0.80 | 0.80 | 0.80 | 0.80 | 1.01 |
| 0.80 | 0.80 | 0.80 | 0.80 | 1.00 | 1.15 | 1.30 |
| 0.80 | 0.80 | 1.11 | 1.22 | 1.34 | 1.46 | 1.58 |
| 1.32 | 1.41 | 2.50 | 2.29 | 2.27 | 1.78 | 1.87 |
| 1.77 | 1.83 | 1.90 | 1.96 | 2.50 | 2.40 | 2.50 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 1.02 | 1.14 | 1.26 |
| 0.80 | 1.08 | 1.17 | 1.27 | 1.37 | 1.46 | 1.56 |
| 1.44 | 1.51 | 1.58 | 1.64 | 1.71 | 1.78 | 1.85 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |

Fig. 14j'

| | | | | | | |
|---|---|---|---|---|---|---|
| 0.80 | 0.80 | 0.80 | 0.80 | 1.04 | 1.14 | 1.24 |
| 1.10 | 1.17 | 1.25 | 1.32 | 1.39 | 1.47 | 1.54 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 1.07 | 1.14 | 1.22 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 2.05 | 2.04 | 2.17 | 2.25 | 2.36 | 2.41 | 2.50 |
| 2.05 | 2.31 | 2.32 | 2.40 | 2.45 | 2.41 | 2.50 |
| 2.38 | 2.38 | 2.50 | 2.50 | 2.44 | 2.46 | 2.48 |
| 2.41 | 2.50 | 2.46 | 2.50 | 2.47 | 2.49 | 2.48 |
| 2.50 | 2.50 | 2.50 | 2.50 | 2.50 | 2.50 | 2.50 |
| 0.85 | 1.22 | 1.17 | 1.64 | 2.13 | 2.39 | 2.30 |
| 1.72 | 1.79 | 2.10 | 1.98 | 2.19 | 2.37 | 2.50 |
| 2.15 | 2.17 | 2.25 | 2.35 | 2.43 | 2.36 | 2.45 |
| 2.39 | 2.42 | 2.43 | 2.45 | 2.45 | 2.47 | 2.49 |
| 2.50 | 2.39 | 2.43 | 2.50 | 2.50 | 2.50 | 2.50 |
| 0.53 | 0.56 | 0.80 | 1.19 | 1.37 | 1.83 | 2.01 |
| 1.11 | 1.18 | 1.51 | 1.51 | 1.74 | 2.12 | 2.50 |
| 1.67 | 1.83 | 2.15 | 2.08 | 2.15 | 2.21 | 2.47 |
| 2.11 | 2.28 | 2.25 | 2.32 | 2.36 | 2.30 | 2.48 |
| 2.41 | 2.49 | 2.40 | 2.50 | 2.48 | 2.49 | 2.49 |
| 0.16 | 0.56 | 0.63 | 0.80 | 1.33 | 1.52 | 1.71 |
| 0.65 | 0.67 | 1.12 | 1.18 | 1.83 | 2.07 | 2.31 |
| 1.00 | 1.00 | 1.66 | 1.74 | 1.98 | 2.16 | 2.50 |
| 1.74 | 1.96 | 2.13 | 2.18 | 2.26 | 2.31 | 2.37 |
| 2.13 | 2.50 | 2.43 | 2.46 | 2.48 | 2.49 | 2.47 |
| 0.26 | 0.18 | 0.40 | 0.80 | 0.80 | 1.21 | 1.40 |
| 0.80 | 0.46 | 0.80 | 0.80 | 1.34 | 1.51 | 1.68 |
| 0.80 | 1.20 | 1.35 | 1.51 | 1.66 | 2.02 | 2.26 |
| 1.45 | 1.58 | 1.90 | 1.91 | 1.99 | 2.14 | 2.50 |
| 1.84 | 1.96 | 2.26 | 2.20 | 2.43 | 2.50 | 2.47 |

Fig. 14k

| | | | | | | |
|---|---|---|---|---|---|---|
| 0.20 | 0.11 | 0.00 | 0.80 | 0.80 | 0.90 | 1.09 |
| 0.32 | 0.80 | 0.13 | 0.80 | 1.04 | 1.21 | 1.38 |
| 0.19 | 0.80 | 1.05 | 1.21 | 1.36 | 1.52 | 1.67 |
| 0.80 | 1.28 | 1.42 | 2.25 | 2.20 | 2.20 | 2.27 |
| 1.55 | 1.66 | 1.78 | 1.90 | 2.50 | 2.43 | 2.33 |
| 0.00 | 0.80 | 0.80 | 0.80 | 0.80 | 0.80 | 0.80 |
| 0.19 | 0.80 | 0.80 | 0.80 | 0.80 | 0.80 | 0.80 |
| 0.80 | 0.80 | 0.80 | 0.80 | 1.06 | 1.22 | 1.38 |
| 0.80 | 0.98 | 1.12 | 1.26 | 1.40 | 1.54 | 1.68 |
| 1.24 | 1.36 | 1.49 | 1.61 | 1.73 | 2.50 | 2.50 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.60 | 0.76 | 0.80 | 0.80 |
| 0.80 | 0.80 | 0.81 | 0.96 | 1.10 | 1.24 | 1.38 |
| 0.93 | 1.06 | 1.19 | 1.31 | 1.44 | 1.56 | 1.69 |
| 0.80 | 0.80 | 0.80 | 0.80 | 0.80 | 0.00 | 0.15 |
| 0.80 | 0.80 | 0.80 | 0.80 | 0.80 | 0.28 | 0.46 |
| 0.80 | 0.80 | 0.80 | 0.80 | 0.45 | 0.61 | 0.77 |
| 0.80 | 0.80 | 0.80 | 0.80 | 0.79 | 0.94 | 1.08 |
| 0.80 | 0.80 | 0.88 | 1.01 | 1.14 | 1.27 | 1.40 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.14 | 0.30 | 0.46 |
| 0.80 | 0.05 | 0.20 | 0.34 | 0.49 | 0.63 | 0.78 |
| 0.31 | 0.44 | 0.57 | 0.70 | 0.84 | 0.97 | 1.10 |
| 1.95 | 1.95 | 2.01 | 2.10 | 2.31 | 2.41 | 2.50 |
| 2.22 | 2.23 | 2.32 | 2.35 | 2.41 | 2.47 | 2.50 |
| 2.33 | 2.46 | 2.50 | 2.50 | 2.44 | 2.50 | 2.50 |
| 2.50 | 2.45 | 2.46 | 2.50 | 2.50 | 2.47 | 2.50 |
| 2.32 | 2.50 | 2.50 | 2.50 | 2.45 | 2.50 | 2.50 |
| 1.00 | 1.19 | 1.47 | 1.51 | 1.88 | 2.21 | 2.50 |
| 1.12 | 1.50 | 1.92 | 1.95 | 2.16 | 2.42 | 2.50 |
| 2.18 | 2.26 | 2.19 | 2.23 | 2.40 | 2.41 | 2.47 |
| 2.38 | 2.33 | 2.32 | 2.40 | 2.46 | 2.42 | 2.48 |
| 2.50 | 2.50 | 2.43 | 2.50 | 2.47 | 2.48 | 2.49 |
| 0.49 | 0.74 | 0.82 | 1.24 | 1.63 | 1.72 | 2.50 |
| 0.90 | 0.86 | 1.39 | 1.53 | 1.67 | 2.21 | 2.50 |

Fig. 14k$^I$

| | | | | | | |
|---|---|---|---|---|---|---|
| 1.39 | 1.65 | 1.92 | 2.03 | 1.99 | 2.26 | 2.47 |
| 1.68 | 2.24 | 2.33 | 2.33 | 2.28 | 2.36 | 2.42 |
| 1.96 | 2.23 | 2.44 | 2.35 | 2.48 | 2.47 | 2.50 |
| 0.23 | 0.36 | 0.41 | 1.06 | 1.25 | 1.43 | 1.60 |
| 0.39 | 0.66 | 0.82 | 0.90 | 1.52 | 1.91 | 2.50 |
| 0.74 | 1.31 | 1.50 | 1.61 | 1.73 | 2.12 | 2.40 |
| 1.41 | 1.58 | 1.89 | 2.16 | 2.07 | 2.21 | 2.47 |
| 1.69 | 1.86 | 2.24 | 2.42 | 2.42 | 2.48 | 2.50 |
| 0.06 | 0.17 | 0.26 | 0.41 | 0.80 | 0.80 | 1.31 |
| 0.29 | 0.36 | 0.60 | 0.79 | 1.02 | 1.43 | 1.60 |
| 0.63 | 0.71 | 1.34 | 0.99 | 1.54 | 1.83 | 2.30 |
| 0.80 | 1.30 | 1.48 | 1.34 | 2.02 | 1.85 | 2.38 |
| 1.41 | 1.59 | 1.77 | 2.40 | 2.36 | 2.46 | 2.48 |
| 0.06 | 0.18 | 0.22 | 0.17 | 0.80 | 0.80 | 1.00 |
| 0.14 | 0.12 | 0.33 | 0.50 | 0.80 | 1.14 | 1.31 |
| 0.25 | 0.80 | 0.80 | 0.80 | 1.26 | 1.44 | 1.65 |
| 0.80 | 1.01 | 1.19 | 1.37 | 1.56 | 1.74 | 1.92 |
| 1.12 | 1.30 | 1.49 | 2.14 | 2.23 | 2.35 | 2.46 |
| 0.07 | 0.00 | 0.80 | 0.80 | 0.80 | 0.80 | 0.71 |
| 0.09 | 0.00 | 0.80 | 0.80 | 0.80 | 0.84 | 1.02 |
| 0.12 | 0.80 | 0.13 | 0.80 | 0.97 | 0.80 | 1.33 |
| 0.80 | 0.80 | 0.80 | 0.34 | 1.27 | 1.46 | 1.64 |
| 0.80 | 1.02 | 1.20 | 1.39 | 1.57 | 2.39 | 2.21 |
| 0.80 | 0.80 | 0.80 | 0.80 | 0.80 | 0.80 | 0.80 |
| 0.80 | 0.80 | 0.00 | 0.80 | 0.80 | 0.80 | 0.80 |
| 0.80 | 0.80 | 0.80 | 0.80 | 0.80 | 0.86 | 1.04 |
| 0.80 | 0.80 | 0.80 | 0.80 | 0.98 | 1.17 | 1.35 |
| 0.80 | 0.80 | 0.91 | 1.10 | 2.27 | 2.37 | 2.36 |
| 0.80 | 0.80 | 0.80 | 0.80 | 0.80 | 0.80 | 0.80 |
| 0.80 | 0.80 | 0.80 | 0.80 | 0.80 | 0.26 | 0.43 |
| 0.80 | 0.80 | 0.80 | 0.80 | 0.39 | 0.57 | 0.75 |
| 0.80 | 0.80 | 0.32 | 0.51 | 0.69 | 0.88 | 1.07 |
| 0.24 | 0.43 | 0.62 | 0.81 | 1.00 | 1.19 | 1.38 |
| 0.80 | 0.80 | 0.80 | 0.80 | 0.80 | 0.80 | 0.80 |
| 0.80 | 0.80 | 0.80 | 0.80 | 0.80 | 0.80 | 0.14 |
| 0.80 | 0.80 | 0.80 | 0.80 | 0.09 | 0.27 | 0.46 |
| 0.80 | 0.80 | 0.80 | 0.21 | 0.40 | 0.59 | 0.78 |

Fig. 14I

| | | | | | | |
|---|---|---|---|---|---|---|
| 0.80 | 0.14 | 0.33 | 0.52 | 0.71 | 0.90 | 1.09 |
| 1.94 | 2.19 | 2.03 | 2.36 | 2.31 | 2.41 | 2.50 |
| 1.48 | 2.14 | 2.06 | 2.34 | 2.45 | 2.44 | 2.50 |
| 2.31 | 2.50 | 2.41 | 2.50 | 2.50 | 2.50 | 2.50 |
| 1.74 | 2.50 | 2.12 | 2.50 | 2.44 | 2.50 | 2.50 |
| 1.86 | 2.07 | 2.28 | 2.50 | 2.50 | 2.50 | 2.50 |
| 1.10 | 1.21 | 1.58 | 1.80 | 2.05 | 2.37 | 2.01 |
| 1.25 | 1.33 | 1.83 | 2.10 | 2.01 | 2.36 | 2.50 |
| 1.39 | 1.58 | 2.01 | 2.02 | 2.24 | 2.42 | 2.44 |
| 1.53 | 2.25 | 2.37 | 2.32 | 2.40 | 2.40 | 2.50 |
| 1.67 | 1.90 | 2.50 | 2.44 | 2.43 | 2.48 | 2.50 |
| 0.50 | 0.85 | 0.76 | 1.31 | 1.77 | 2.12 | 1.76 |
| 0.71 | 0.83 | 0.98 | 1.43 | 1.94 | 2.19 | 2.40 |
| 0.80 | 1.34 | 1.50 | 1.94 | 2.14 | 2.08 | 2.50 |
| 1.29 | 1.51 | 2.23 | 1.96 | 2.33 | 2.21 | 2.48 |
| 1.44 | 1.67 | 2.50 | 2.29 | 2.42 | 2.45 | 2.48 |
| 0.25 | 0.30 | 0.51 | 0.78 | 1.21 | 1.36 | 1.51 |
| 0.33 | 0.58 | 0.65 | 1.27 | 1.31 | 1.84 | 2.50 |
| 0.55 | 1.02 | 0.95 | 1.02 | 1.72 | 2.06 | 2.27 |
| 1.05 | 1.26 | 1.25 | 1.81 | 1.96 | 2.11 | 2.47 |
| 1.19 | 1.43 | 2.14 | 2.33 | 2.38 | 2.43 | 2.45 |
| 0.07 | 0.19 | 0.30 | 0.52 | 0.80 | 1.11 | 1.26 |
| 0.17 | 0.37 | 0.46 | 0.60 | 0.92 | 1.37 | 1.54 |
| 0.51 | 0.58 | 0.86 | 0.96 | 1.27 | 1.63 | 2.35 |
| 0.55 | 0.80 | 1.00 | 1.40 | 1.40 | 1.69 | 2.34 |
| 0.95 | 1.19 | 2.21 | 2.25 | 2.31 | 2.39 | 2.44 |
| 0.14 | 0.15 | 0.12 | 0.23 | 0.80 | 0.86 | 1.01 |
| 0.18 | 0.09 | 0.34 | 0.25 | 0.80 | 0.80 | 1.30 |
| 0.24 | 0.15 | 0.39 | 0.62 | 0.87 | 1.38 | 2.31 |
| 0.18 | 0.33 | 0.87 | 1.21 | 1.09 | 1.71 | 1.86 |
| 0.80 | 0.94 | 1.18 | 1.89 | 2.05 | 2.28 | 2.28 |
| 0.12 | 0.15 | 0.13 | 0.21 | 0.80 | 0.80 | 0.80 |
| 0.00 | 0.12 | 0.29 | 0.07 | 0.34 | 0.00 | 1.05 |
| 0.05 | 0.16 | 0.52 | 0.61 | 0.80 | 0.80 | 1.33 |
| 0.28 | 0.80 | 0.80 | 0.80 | 1.18 | 1.40 | 1.62 |
| 0.80 | 0.80 | 0.93 | 1.18 | 1.42 | 2.36 | 2.34 |
| 0.23 | 0.15 | 0.00 | 0.80 | 0.80 | 0.80 | 0.80 |

Fig. 14I'

| 0.00 | 0.08 | 0.80 | 0.10 | 0.80 | 0.80 | 0.81 |
|------|------|------|------|------|------|------|
| 0.21 | 0.07 | 0.26 | 0.10 | 0.80 | 0.89 | 1.08 |
| 0.17 | 0.13 | 0.80 | 0.80 | 0.80 | 1.15 | 1.37 |
| 0.80 | 0.80 | 0.80 | 0.93 | 1.17 | 2.13 | 1.66 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.64 | 0.83 |
| 0.80 | 0.80 | 0.23 | 0.80 | 0.68 | 0.90 | 1.12 |
| 0.80 | 0.80 | 0.80 | 0.68 | 0.92 | 1.17 | 1.41 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.38 | 0.58 |
| 0.80 | 0.80 | 0.80 | 0.80 | 0.43 | 0.65 | 0.87 |
| 0.80 | 0.80 | 0.80 | 0.43 | 0.67 | 0.92 | 1.16 |
| 2.35 | 2.20 | 2.30 | 2.50 | 2.28 | 2.50 | 2.25 |
| 1.44 | 1.61 | 1.79 | 2.50 | 2.28 | 2.50 | 2.50 |
| 1.51 | 1.71 | 2.31 | 2.50 | 2.32 | 2.50 | 2.50 |
| 1.58 | 1.81 | 2.03 | 2.26 | 2.49 | 2.50 | 2.50 |
| 1.65 | 1.90 | 2.16 | 2.50 | 2.50 | 2.40 | 2.50 |
| 0.80 | 1.50 | 1.43 | 1.90 | 2.17 | 2.50 | 2.50 |
| 1.20 | 1.38 | 1.55 | 2.03 | 2.33 | 2.46 | 2.50 |
| 1.27 | 1.47 | 1.67 | 2.20 | 2.38 | 2.41 | 2.44 |
| 1.34 | 1.56 | 2.14 | 2.34 | 2.50 | 2.45 | 2.46 |
| 1.41 | 1.66 | 2.50 | 2.50 | 2.42 | 2.50 | 2.50 |
| 0.56 | 0.97 | 1.30 | 1.72 | 1.49 | 1.63 | 1.78 |
| 0.69 | 0.90 | 1.14 | 1.31 | 1.88 | 2.41 | 2.50 |
| 0.80 | 1.23 | 1.43 | 1.63 | 1.88 | 2.20 | 2.46 |
| 1.10 | 1.33 | 1.55 | 1.99 | 2.15 | 2.43 | 2.47 |
| 1.17 | 1.42 | 2.20 | 2.50 | 2.47 | 2.50 | 2.48 |
| 0.26 | 0.48 | 0.71 | 0.80 | 1.25 | 2.39 | 1.55 |
| 0.29 | 0.46 | 0.59 | 0.94 | 1.51 | 1.79 | 2.29 |
| 0.55 | 0.57 | 0.96 | 1.20 | 1.51 | 1.87 | 2.33 |
| 0.37 | 1.09 | 1.32 | 1.87 | 1.63 | 1.87 | 2.30 |
| 0.94 | 1.19 | 2.12 | 2.14 | 2.41 | 2.48 | 2.46 |
| 0.23 | 0.28 | 0.60 | 0.64 | 0.80 | 1.17 | 0.80 |
| 0.24 | 0.23 | 0.36 | 0.72 | 0.71 | 1.36 | 2.31 |
| 0.28 | 0.42 | 0.49 | 0.62 | 1.11 | 1.45 | 2.17 |

Fig. 14m

| 0.44 | 0.59 | 0.88 | 1.15 | 1.38 | 1.46 | 2.31 |
| --- | --- | --- | --- | --- | --- | --- |
| 0.80 | 0.95 | 2.14 | 1.45 | 2.26 | 2.32 | 2.39 |
| 0.05 | 0.07 | 0.28 | 0.29 | 0.80 | 0.93 | 1.08 |
| 0.10 | 0.17 | 0.27 | 0.41 | 0.47 | 0.80 | 1.30 |
| 0.15 | 0.21 | 0.21 | 0.36 | 0.75 | 1.32 | 1.52 |
| 0.21 | 0.25 | 0.39 | 0.47 | 0.90 | 1.14 | 1.83 |
| 0.80 | 0.72 | 0.96 | 2.04 | 1.82 | 2.26 | 2.31 |
| 0.05 | 0.00 | 0.28 | 0.09 | 0.80 | 0.70 | 0.85 |
| 0.09 | 0.08 | 0.17 | 0.25 | 0.37 | 0.80 | 1.06 |
| 0.03 | 0.05 | 0.21 | 0.27 | 0.36 | 0.51 | 1.28 |
| 0.09 | 0.27 | 0.27 | 0.36 | 0.70 | 1.28 | 1.50 |
| 0.00 | 0.33 | 0.80 | 0.98 | 1.83 | 2.00 | 2.13 |
| 0.09 | 0.17 | 0.25 | 0.21 | 0.80 | 0.80 | 0.80 |
| 0.06 | 0.03 | 0.06 | 0.07 | 0.29 | 0.80 | 0.83 |
| 0.04 | 0.09 | 0.13 | 0.15 | 0.24 | 0.32 | 1.05 |
| 0.00 | 0.27 | 0.19 | 0.23 | 0.44 | 0.37 | 1.27 |
| 0.80 | 0.18 | 0.50 | 0.74 | 0.99 | 1.96 | 2.12 |
| 0.80 | 0.80 | 0.80 | 0.80 | 0.80 | 0.80 | 0.80 |
| 0.20 | 0.00 | 0.00 | 0.19 | 0.80 | 0.80 | 0.80 |
| 0.00 | 0.00 | 0.80 | 0.26 | 0.00 | 0.23 | 0.80 |
| 0.16 | 0.00 | 0.20 | 0.09 | 0.80 | 0.80 | 0.80 |
| 0.80 | 0.80 | 0.80 | 0.51 | 0.76 | 1.00 | 1.25 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |
| 0.80 | 0.80 | 0.80 | 0.80 | 0.80 | 0.80 | 0.58 |
| 0.80 | 0.80 | 0.80 | 0.80 | 0.80 | 0.58 | 0.80 |
| 0.80 | 0.80 | 0.80 | 0.80 | 0.52 | 0.77 | 1.02 |
| 1.36 | 2.50 | 1.71 | 2.38 | 2.50 | 2.50 | 2.41 |
| 1.43 | 2.50 | 2.50 | 2.31 | 2.29 | 2.50 | 2.50 |
| 1.64 | 1.96 | 2.28 | 2.60 | 2.50 | 2.50 | 2.50 |
| 1.78 | 2.17 | 2.50 | 2.50 | 2.50 | 2.50 | 2.50 |
| 1.92 | 2.38 | 2.50 | 2.50 | 2.50 | 2.50 | 2.50 |
| 1.14 | 1.30 | 2.06 | 1.61 | 2.43 | 2.50 | 2.09 |
| 1.19 | 1.39 | 1.59 | 1.79 | 2.25 | 2.50 | 2.37 |
| 1.24 | 1.48 | 1.72 | 1.96 | 2.33 | 2.43 | 2.50 |
| 1.28 | 1.57 | 1.85 | 2.34 | 2.50 | 2.41 | 2.50 |
| 1.33 | 1.66 | 1.99 | 2.31 | 2.50 | 2.50 | 2.50 |

Fig. 14m¹

| | | | | | | |
|---|---|---|---|---|---|---|
| 1.04 | 1.33 | 1.25 | 1.40 | 2.24 | 2.38 | 1.86 |
| 0.80 | 1.14 | 1.33 | 1.51 | 2.01 | 2.19 | 2.50 |
| 0.80 | 1.19 | 1.41 | 1.63 | 2.08 | 2.22 | 2.45 |
| 1.00 | 1.24 | 1.49 | 2.06 | 2.08 | 2.40 | 2.50 |
| 1.02 | 1.30 | 1.58 | 2.34 | 2.45 | 2.50 | 2.48 |
| 0.46 | 0.82 | 1.05 | 1.20 | 1.35 | 1.51 | 1.66 |
| 0.50 | 0.50 | 0.62 | 1.05 | 1.46 | 2.03 | 2.40 |
| 0.46 | 0.80 | 0.80 | 1.37 | 1.56 | 1.94 | 2.31 |
| 0.80 | 0.80 | 1.22 | 1.45 | 1.96 | 2.08 | 2.43 |
| 0.76 | 1.02 | 2.29 | 1.54 | 2.25 | 2.40 | 2.50 |
| 0.29 | 0.36 | 0.49 | 0.80 | 1.16 | 1.31 | 1.46 |
| 0.27 | 0.23 | 0.44 | 0.50 | 1.25 | 1.42 | 2.38 |
| 0.36 | 0.37 | 0.42 | 0.58 | 0.92 | 1.54 | 2.27 |
| 0.06 | 0.48 | 0.60 | 0.83 | 1.35 | 1.52 | 2.33 |
| 0.80 | 0.78 | 1.03 | 2.07 | 2.26 | 2.28 | 2.36 |
| 0.15 | 0.15 | 0.48 | 0.80 | 0.80 | 1.12 | 1.27 |
| 0.13 | 0.23 | 0.13 | 0.32 | 0.39 | 1.00 | 1.39 |
| 0.15 | 0.15 | 0.26 | 0.38 | 0.56 | 0.97 | 2.02 |
| 0.12 | 0.33 | 0.43 | 0.63 | 0.87 | 1.16 | 1.93 |
| 0.00 | 0.80 | 0.80 | 1.03 | 1.84 | 2.17 | 2.08 |
| 0.13 | 0.06 | 0.22 | 0.80 | 0.78 | 0.93 | 1.08 |
| 0.04 | 0.14 | 0.19 | 0.27 | 0.15 | 0.80 | 1.18 |
| 0.05 | 0.08 | 0.16 | 0.29 | 0.43 | 0.67 | 1.29 |
| 0.07 | 0.08 | 0.15 | 0.35 | 0.58 | 0.75 | 1.88 |
| 0.10 | 0.80 | 0.47 | 0.81 | 1.43 | 1.67 | 1.98 |
| 0.08 | 0.23 | 0.22 | 0.80 | 0.80 | 0.80 | 0.89 |
| 0.03 | 0.09 | 0.03 | 0.10 | 0.16 | 0.80 | 0.99 |
| 0.00 | 0.00 | 0.06 | 0.14 | 0.32 | 0.80 | 1.08 |
| 0.08 | 0.07 | 0.08 | 0.19 | 0.38 | 0.35 | 1.18 |
| 0.00 | 0.21 | 0.35 | 0.61 | 1.29 | 1.26 | 1.89 |
| 0.00 | 0.80 | 0.00 | 0.80 | 0.80 | 0.80 | 0.80 |
| 0.08 | 0.04 | 0.00 | 0.17 | 0.00 | 0.80 | 0.80 |
| 0.00 | 0.08 | 0.06 | 0.09 | 0.00 | 0.36 | 0.80 |
| 0.04 | 0.04 | 0.10 | 0.04 | 0.23 | 0.25 | 0.15 |
| 0.00 | 0.80 | 0.20 | 0.80 | 0.61 | 1.47 | 1.94 |
| 0.80 | 0.80 | 0.80 | 0.80 | 0.80 | 0.80 | 0.80 |
| 0.80 | 0.80 | 0.80 | 0.80 | 0.80 | 0.80 | 0.80 |

Fig. 14n

| | | | | | | |
|---|---|---|---|---|---|---|
| 0.80 | 0.15 | 0.18 | 0.80 | 0.00 | 0.80 | 0.80 |
| 0.80 | 0.00 | 0.00 | 0.00 | 0.00 | 0.80 | 0.80 |
| 0.80 | 0.80 | 0.80 | 0.19 | 0.41 | 0.80 | 2.01 |
| 1.48 | 2.50 | 1.90 | 2.50 | 2.50 | 2.50 | 2.50 |
| 1.64 | 1.92 | 2.20 | 2.48 | 2.50 | 2.50 | 2.50 |
| 1.79 | 2.14 | 2.49 | 2.50 | 2.50 | 2.50 | 2.50 |
| 1.95 | 2.37 | 2.50 | 2.50 | 2.50 | 2.50 | 2.50 |
| 2.11 | 2.50 | 2.50 | 2.50 | 2.50 | 2.50 | 2.50 |
| 1.24 | 1.44 | 2.50 | 2.40 | 2.50 | 2.50 | 2.41 |
| 1.29 | 1.51 | 2.38 | 1.60 | 2.36 | 2.50 | 2.41 |
| 1.33 | 1.59 | 2.27 | 2.10 | 2.50 | 2.50 | 2.50 |
| 1.38 | 1.67 | 1.95 | 2.24 | 2.50 | 2.50 | 2.50 |
| 1.43 | 1.74 | 2.06 | 2.38 | 2.50 | 2.42 | 2.50 |
| 1.05 | 1.24 | 2.03 | 2.16 | 2.22 | 2.40 | 2.17 |
| 1.06 | 1.26 | 1.47 | 2.31 | 2.40 | 2.50 | 2.50 |
| 1.06 | 1.29 | 1.51 | 1.74 | 2.31 | 2.50 | 2.44 |
| 1.07 | 1.31 | 1.56 | 1.80 | 2.31 | 2.50 | 2.50 |
| 1.08 | 1.34 | 1.60 | 2.50 | 2.40 | 2.46 | 2.50 |
| 0.71 | 1.05 | 1.23 | 1.41 | 2.21 | 2.38 | 1.97 |
| 0.80 | 0.80 | 1.24 | 1.44 | 1.64 | 2.23 | 2.50 |
| 0.80 | 0.80 | 1.26 | 1.47 | 1.68 | 2.18 | 2.41 |
| 0.80 | 1.05 | 1.27 | 1.49 | 2.33 | 2.22 | 2.50 |
| 0.80 | 1.05 | 1.28 | 2.50 | 2.45 | 2.39 | 2.50 |
| 0.46 | 0.80 | 1.04 | 1.23 | 1.41 | 2.50 | 1.80 |
| 0.12 | 0.63 | 0.53 | 0.80 | 1.42 | 2.18 | 2.39 |
| 0.24 | 0.28 | 0.56 | 1.23 | 1.43 | 1.93 | 2.42 |
| 0.35 | 0.23 | 1.03 | 0.80 | 1.65 | 1.86 | 2.47 |
| 0.80 | 0.80 | 1.02 | 1.24 | 2.37 | 2.39 | 2.39 |
| 0.25 | 0.80 | 0.80 | 1.04 | 1.22 | 1.40 | 1.58 |
| 0.09 | 0.25 | 0.53 | 0.48 | 0.80 | 1.40 | 2.50 |
| 0.03 | 0.14 | 0.25 | 0.47 | 0.58 | 1.45 | 2.24 |
| 0.06 | 0.18 | 0.41 | 0.56 | 0.77 | 1.34 | 2.23 |
| 0.80 | 0.80 | 0.80 | 1.23 | 2.07 | 2.08 | 2.34 |
| 0.07 | 0.13 | 0.36 | 0.80 | 0.80 | 1.22 | 1.40 |
| 0.06 | 0.14 | 0.25 | 0.28 | 0.45 | 1.20 | 1.39 |
| 0.14 | 0.07 | 0.15 | 0.21 | 0.42 | 0.93 | 2.02 |
| 0.07 | 0.07 | 0.23 | 0.42 | 0.39 | 0.87 | 1.92 |

Fig. 14n'

| | | | | | | |
|---|---|---|---|---|---|---|
| 0.00 | 0.38 | 0.29 | 0.78 | 1.29 | 1.43 | 2.18 |
| 0.11 | 0.13 | 0.00 | 0.34 | 0.80 | 1.04 | 1.21 |
| 0.00 | 0.06 | 0.04 | 0.29 | 0.38 | 1.01 | 1.19 |
| 0.05 | 0.00 | 0.17 | 0.19 | 0.21 | 0.39 | 1.17 |
| 0.00 | 0.05 | 0.12 | 0.10 | 0.32 | 0.38 | 1.00 |
| 0.00 | 0.13 | 0.28 | 0.54 | 0.98 | 1.01 | 1.82 |
| 0.00 | 0.00 | 0.00 | 0.80 | 0.80 | 0.80 | 1.03 |
| 0.02 | 0.05 | 0.05 | 0.00 | 0.80 | 0.80 | 1.00 |
| 0.03 | 0.04 | 0.05 | 0.02 | 0.32 | 0.00 | 0.80 |
| 0.12 | 0.03 | 0.03 | 0.11 | 0.09 | 0.20 | 0.80 |
| 0.12 | 0.17 | 0.26 | 0.27 | 0.59 | 1.04 | 1.65 |
| 0.80 | 0.80 | 0.80 | 0.80 | 0.80 | 0.80 | 0.80 |
| 0.00 | 0.00 | 0.00 | 0.10 | 0.80 | 0.80 | 0.80 |
| 0.04 | 0.00 | 0.00 | 0.00 | 0.00 | 0.00 | 0.80 |
| 0.00 | 0.00 | 0.04 | 0.00 | 0.12 | 0.07 | 0.73 |
| 0.80 | 0.80 | 0.00 | 0.80 | 0.80 | 1.25 | 1.77 |
| 1.51 | 1.74 | 1.97 | 2.20 | 2.44 | 2.50 | 2.50 |
| 1.67 | 1.97 | 2.27 | 2.50 | 2.50 | 2.50 | 2.50 |
| 1.83 | 2.20 | 2.50 | 2.50 | 2.50 | 2.50 | 2.50 |
| 1.98 | 2.43 | 2.50 | 2.50 | 2.50 | 2.50 | 2.50 |
| 2.14 | 2.50 | 2.50 | 2.50 | 2.50 | 2.50 | 2.50 |
| 1.29 | 1.50 | 1.71 | 1.92 | 2.50 | 2.50 | 2.50 |
| 1.32 | 1.56 | 1.80 | 2.50 | 2.50 | 2.50 | 2.50 |
| 1.35 | 1.63 | 1.90 | 2.50 | 2.50 | 2.50 | 2.50 |
| 1.39 | 1.69 | 1.99 | 2.29 | 2.50 | 2.50 | 2.50 |
| 1.42 | 1.75 | 2.08 | 2.42 | 2.50 | 2.50 | 2.50 |
| 1.11 | 1.31 | 1.51 | 1.72 | 2.50 | 2.31 | 2.50 |
| 0.80 | 1.32 | 1.54 | 1.76 | 2.33 | 2.50 | 2.50 |
| 1.09 | 1.33 | 1.56 | 1.80 | 2.04 | 2.50 | 2.50 |
| 1.08 | 1.33 | 1.59 | 1.84 | 2.09 | 2.50 | 2.50 |
| 1.07 | 1.34 | 1.61 | 1.88 | 2.26 | 2.50 | 2.50 |
| 0.93 | 1.13 | 1.33 | 1.53 | 2.50 | 2.50 | 2.50 |
| 0.80 | 1.11 | 1.32 | 1.53 | 2.35 | 2.43 | 2.50 |
| 0.80 | 0.80 | 1.31 | 1.53 | 2.24 | 2.50 | 2.50 |
| 0.85 | 1.08 | 1.31 | 1.53 | 1.76 | 2.37 | 2.50 |
| 0.82 | 1.06 | 1.30 | 2.27 | 2.50 | 2.46 | 2.48 |
| 0.53 | 0.96 | 1.16 | 1.36 | 2.32 | 2.50 | 2.50 |

Fig. 14o

| | | | | | | |
|---|---|---|---|---|---|---|
| 0.21 | 0.80 | 1.13 | 1.33 | 1.54 | 2.39 | 2.41 |
| 0.19 | 0.29 | 0.80 | 1.31 | 1.52 | 2.24 | 2.50 |
| 0.80 | 0.33 | 1.07 | 1.29 | 1.50 | 2.01 | 2.44 |
| 0.80 | 0.82 | 1.04 | 2.33 | 2.35 | 2.32 | 2.47 |
| 0.38 | 0.80 | 0.99 | 1.19 | 1.38 | 2.32 | 2.50 |
| 0.07 | 0.09 | 0.65 | 1.15 | 1.35 | 2.31 | 2.50 |
| 0.04 | 0.22 | 0.23 | 0.60 | 1.31 | 1.51 | 2.35 |
| 0.07 | 0.35 | 0.35 | 0.38 | 1.27 | 2.02 | 2.33 |
| 0.80 | 0.80 | 1.03 | 1.23 | 1.96 | 2.17 | 2.44 |
| 0.08 | 0.80 | 0.82 | 1.02 | 1.22 | 1.41 | 1.61 |
| 0.11 | 0.25 | 0.16 | 0.44 | 0.80 | 1.36 | 1.56 |
| 0.05 | 0.07 | 0.22 | 0.24 | 0.80 | 1.31 | 2.15 |
| 0.03 | 0.14 | 0.07 | 0.36 | 0.56 | 1.05 | 2.09 |
| 0.00 | 0.09 | 0.37 | 0.80 | 1.01 | 1.70 | 2.34 |
| 0.12 | 0.80 | 0.80 | 0.85 | 1.05 | 1.24 | 1.44 |
| 0.14 | 0.08 | 0.08 | 0.38 | 0.80 | 1.18 | 1.37 |
| 0.04 | 0.08 | 0.10 | 0.22 | 0.28 | 1.12 | 2.50 |
| 0.01 | 0.03 | 0.05 | 0.21 | 0.21 | 0.51 | 1.88 |
| 0.00 | 0.04 | 0.19 | 0.37 | 0.83 | 1.12 | 1.99 |
| 0.18 | 0.80 | 0.80 | 0.69 | 0.88 | 1.08 | 1.27 |
| 0.04 | 0.08 | 0.06 | 0.05 | 0.80 | 0.80 | 1.20 |
| 0.01 | 0.01 | 0.02 | 0.07 | 0.29 | 0.42 | 1.12 |
| 0.02 | 0.01 | 0.01 | 0.06 | 0.16 | 0.25 | 1.38 |
| 0.00 | 0.03 | 0.03 | 0.18 | 0.35 | 0.53 | 1.86 |
| 0.80 | 0.80 | 0.80 | 0.80 | 0.80 | 0.91 | 1.10 |
| 0.00 | 0.05 | 0.05 | 0.22 | 0.80 | 0.80 | 1.02 |
| 0.05 | 0.00 | 0.04 | 0.11 | 0.04 | 0.34 | 0.94 |
| 0.02 | 0.02 | 0.05 | 0.02 | 0.05 | 0.09 | 0.80 |
| 0.11 | 0.00 | 0.04 | 0.21 | 0.21 | 0.74 | 1.60 |
| 1.50 | 1.76 | 2.02 | 2.28 | 2.50 | 2.50 | 2.50 |
| 1.83 | 2.22 | 2.50 | 2.50 | 2.50 | 2.50 | 2.50 |
| 2.16 | 2.68 | 2.50 | 2.50 | 2.50 | 2.50 | 2.50 |
| 2.50 | 2.50 | 2.50 | 2.50 | 2.50 | 2.50 | 2.50 |
| 2.50 | 2.50 | 2.50 | 2.50 | 2.50 | 2.50 | 2.50 |
| 1.25 | 1.47 | 1.70 | 1.92 | 2.15 | 2.38 | 2.50 |
| 1.36 | 1.64 | 1.92 | 2.20 | 2.49 | 2.50 | 2.50 |
| 1.48 | 1.81 | 2.15 | 2.49 | 2.50 | 2.50 | 2.50 |

Fig. 14o'

| | | | | | | |
|---|---|---|---|---|---|---|
| 1.59 | 1.98 | 2.37 | 2.50 | 2.50 | 2.50 | 2.38 |
| 1.70 | 2.15 | 2.50 | 2.50 | 2.50 | 2.50 | 2.50 |
| 1.07 | 1.28 | 1.50 | 2.50 | 2.50 | 2.50 | 2.50 |
| 1.11 | 1.36 | 1.60 | 1.85 | 2.09 | 2.50 | 2.50 |
| 1.15 | 1.43 | 1.70 | 1.98 | 2.26 | 2.40 | 2.50 |
| 1.19 | 1.50 | 1.81 | 2.11 | 2.42 | 2.50 | 2.50 |
| 1.24 | 1.57 | 1.91 | 2.25 | 2.50 | 2.50 | 2.50 |
| 0.91 | 1.12 | 2.29 | 2.27 | 2.50 | 2.50 | 2.50 |
| 0.91 | 1.14 | 1.37 | 1.59 | 2.31 | 2.50 | 2.50 |
| 0.80 | 1.17 | 1.41 | 1.66 | 2.33 | 2.50 | 2.50 |
| 0.80 | 1.19 | 1.45 | 1.72 | 2.50 | 2.38 | 2.46 |
| 0.80 | 1.21 | 1.50 | 1.78 | 2.06 | 2.50 | 2.50 |
| 0.80 | 0.96 | 1.17 | 2.36 | 2.40 | 2.50 | 2.50 |
| 0.80 | 0.96 | 1.17 | 1.39 | 2.29 | 2.43 | 2.42 |
| 0.80 | 0.80 | 0.80 | 2.27 | 2.40 | 2.50 | 2.46 |
| 0.80 | 0.95 | 1.18 | 1.42 | 1.66 | 2.42 | 2.50 |
| 0.80 | 0.94 | 1.19 | 1.44 | 2.29 | 2.44 | 2.48 |
| 0.80 | 0.81 | 1.01 | 1.22 | 1.42 | 1.62 | 1.82 |
| 0.80 | 0.09 | 1.00 | 1.20 | 1.41 | 2.26 | 2.50 |
| 0.19 | 0.00 | 0.80 | 1.19 | 1.41 | 2.43 | 2.50 |
| 0.80 | 0.23 | 0.80 | 0.80 | 1.40 | 1.62 | 2.45 |
| 0.80 | 0.71 | 0.94 | 1.17 | 2.22 | 2.31 | 2.43 |
| 0.30 | 0.80 | 0.86 | 1.06 | 1.26 | 1.46 | 1.66 |
| 0.08 | 0.11 | 0.27 | 0.80 | 1.23 | 2.50 | 2.50 |
| 0.04 | 0.17 | 0.04 | 0.29 | 1.21 | 1.41 | 2.43 |
| 0.16 | 0.14 | 0.28 | 0.29 | 0.80 | 1.39 | 2.43 |
| 0.00 | 0.00 | 0.80 | 0.93 | 1.15 | 1.94 | 2.44 |
| 0.29 | 0.80 | 0.72 | 0.92 | 1.11 | 1.31 | 1.51 |
| 0.00 | 0.00 | 0.15 | 0.80 | 0.80 | 1.27 | 2.50 |
| 0.03 | 0.09 | 0.03 | 0.21 | 0.44 | 1.22 | 2.33 |
| 0.02 | 0.02 | 0.10 | 0.29 | 0.17 | 0.77 | 2.29 |
| 0.00 | 0.04 | 0.12 | 0.38 | 0.90 | 1.17 | 2.34 |
| 0.24 | 0.10 | 0.80 | 0.80 | 0.97 | 1.16 | 1.36 |
| 0.00 | 0.08 | 0.10 | 0.36 | 0.80 | 1.10 | 1.30 |
| 0.01 | 0.01 | 0.09 | 0.18 | 0.14 | 0.80 | 2.39 |
| 0.01 | 0.05 | 0.01 | 0.10 | 0.18 | 0.42 | 2.02 |
| 0.00 | 0.02 | 0.06 | 0.24 | 0.33 | 0.64 | 2.04 |

Fig. 14p

| 1.59 | 1.98 | 2.37 | 2.50 | 2.50 | 2.50 | 2.38 |
|---|---|---|---|---|---|---|
| 1.70 | 2.15 | 2.50 | 2.50 | 2.50 | 2.50 | 2.50 |
| 1.07 | 1.28 | 1.50 | 2.50 | 2.50 | 2.50 | 2.50 |
| 1.11 | 1.36 | 1.60 | 1.85 | 2.09 | 2.50 | 2.50 |
| 1.15 | 1.43 | 1.70 | 1.98 | 2.26 | 2.40 | 2.50 |
| 1.19 | 1.50 | 1.81 | 2.11 | 2.42 | 2.50 | 2.50 |
| 1.24 | 1.57 | 1.91 | 2.25 | 2.50 | 2.50 | 2.50 |
| 0.91 | 1.12 | 2.29 | 2.27 | 2.50 | 2.50 | 2.50 |
| 0.91 | 1.14 | 1.37 | 1.59 | 2.31 | 2.50 | 2.50 |
| 0.80 | 1.17 | 1.41 | 1.66 | 2.33 | 2.50 | 2.50 |
| 0.80 | 1.19 | 1.45 | 1.72 | 2.50 | 2.38 | 2.46 |
| 0.80 | 1.21 | 1.50 | 1.78 | 2.06 | 2.50 | 2.50 |
| 0.80 | 0.96 | 1.17 | 2.36 | 2.40 | 2.50 | 2.50 |
| 0.80 | 0.96 | 1.17 | 1.39 | 2.29 | 2.43 | 2.42 |
| 0.80 | 0.80 | 0.80 | 2.27 | 2.40 | 2.50 | 2.46 |
| 0.80 | 0.95 | 1.18 | 1.42 | 1.66 | 2.42 | 2.50 |
| 0.80 | 0.94 | 1.19 | 1.44 | 2.29 | 2.44 | 2.48 |
| 0.80 | 0.81 | 1.01 | 1.22 | 1.42 | 1.62 | 1.82 |
| 0.80 | 0.09 | 1.00 | 1.20 | 1.41 | 2.26 | 2.50 |
| 0.19 | 0.00 | 0.80 | 1.19 | 1.41 | 2.43 | 2.50 |
| 0.80 | 0.23 | 0.80 | 0.80 | 1.40 | 1.62 | 2.45 |
| 0.80 | 0.71 | 0.94 | 1.17 | 2.22 | 2.31 | 2.43 |
| 0.30 | 0.80 | 0.86 | 1.06 | 1.26 | 1.46 | 1.66 |
| 0.08 | 0.11 | 0.27 | 0.80 | 1.23 | 2.50 | 2.50 |
| 0.04 | 0.17 | 0.04 | 0.29 | 1.21 | 1.41 | 2.43 |
| 0.16 | 0.14 | 0.28 | 0.29 | 0.80 | 1.39 | 2.43 |
| 0.00 | 0.00 | 0.80 | 0.93 | 1.15 | 1.94 | 2.44 |
| 0.29 | 0.80 | 0.72 | 0.92 | 1.11 | 1.31 | 1.51 |
| 0.00 | 0.00 | 0.15 | 0.80 | 0.80 | 1.27 | 2.50 |
| 0.03 | 0.09 | 0.03 | 0.21 | 0.44 | 1.22 | 2.33 |
| 0.02 | 0.02 | 0.10 | 0.29 | 0.17 | 0.77 | 2.29 |
| 0.00 | 0.04 | 0.12 | 0.38 | 0.90 | 1.17 | 2.34 |
| 0.24 | 0.10 | 0.80 | 0.80 | 0.97 | 1.16 | 1.36 |
| 0.00 | 0.08 | 0.10 | 0.36 | 0.80 | 1.10 | 1.30 |
| 0.01 | 0.01 | 0.09 | 0.18 | 0.14 | 0.80 | 2.39 |
| 0.01 | 0.05 | 0.01 | 0.10 | 0.18 | 0.42 | 2.02 |
| 0.00 | 0.02 | 0.06 | 0.24 | 0.33 | 0.64 | 2.04 |

Fig. 14p'

| | | | | | | |
|---|---|---|---|---|---|---|
| 0.00 | 0.80 | 0.43 | 0.62 | 0.82 | 1.02 | 1.21 |
| 0.03 | 0.09 | 0.05 | 0.00 | 0.80 | 0.94 | 1.13 |
| 0.01 | 0.05 | 0.02 | 0.03 | 0.16 | 0.40 | 1.05 |
| 0.00 | 0.02 | 0.01 | 0.04 | 0.08 | 0.20 | 1.42 |
| 0.00 | 0.02 | 0.03 | 0.08 | 0.22 | 0.39 | 1.61 |
| 1.53 | 1.69 | 1.86 | 2.03 | 2.20 | 2.37 | 2.50 |
| 1.65 | 1.83 | 2.01 | 2.19 | 2.37 | 2.50 | 2.50 |
| 1.77 | 1.96 | 2.16 | 2.35 | 2.50 | 2.50 | 2.50 |
| 1.89 | 2.10 | 2.30 | 2.50 | 2.50 | 2.50 | 2.50 |
| 2.01 | 2.23 | 2.45 | 2.50 | 2.50 | 2.50 | 2.50 |
| 1.29 | 1.46 | 1.63 | 1.79 | 1.96 | 2.13 | 2.30 |
| 1.40 | 1.58 | 1.76 | 1.94 | 2.12 | 2.29 | 2.47 |
| 1.52 | 1.70 | 1.89 | 2.08 | 2.27 | 2.46 | 2.50 |
| 1.63 | 1.83 | 2.02 | 2.22 | 2.42 | 2.50 | 2.50 |
| 1.74 | 1.95 | 2.16 | 2.37 | 2.50 | 2.50 | 2.50 |
| 1.06 | 1.23 | 1.39 | 1.56 | 1.73 | 1.89 | 2.06 |
| 1.17 | 1.35 | 1.52 | 1.70 | 1.88 | 2.05 | 2.23 |
| 1.28 | 1.46 | 1.65 | 1.84 | 2.02 | 2.21 | 2.50 |
| 1.39 | 1.58 | 1.78 | 1.97 | 2.17 | 2.37 | 2.50 |
| 1.50 | 1.70 | 1.91 | 2.11 | 2.32 | 2.50 | 2.50 |
| 0.83 | 1.00 | 1.16 | 1.33 | 1.50 | 1.66 | 1.83 |
| 0.94 | 1.11 | 1.29 | 1.46 | 1.64 | 1.82 | 1.99 |
| 1.05 | 1.23 | 1.41 | 1.60 | 1.78 | 2.33 | 2.40 |
| 1.15 | 1.35 | 1.54 | 1.73 | 1.93 | 2.50 | 2.50 |
| 1.26 | 1.46 | 1.67 | 1.87 | 2.07 | 2.28 | 2.50 |
| 0.60 | 0.77 | 0.93 | 1.10 | 1.27 | 1.43 | 1.60 |
| 0.71 | 0.88 | 1.06 | 1.23 | 1.41 | 1.58 | 2.40 |
| 0.81 | 1.00 | 1.18 | 1.37 | 1.55 | 1.73 | 2.50 |
| 0.92 | 1.11 | 1.31 | 1.50 | 1.69 | 2.50 | 2.50 |
| 1.03 | 1.23 | 1.43 | 1.63 | 2.50 | 2.29 | 2.50 |
| 0.37 | 0.54 | 0.70 | 0.87 | 1.04 | 1.20 | 1.37 |
| 0.48 | 0.65 | 0.83 | 1.00 | 1.18 | 2.50 | 2.39 |
| 0.58 | 0.77 | 0.95 | 1.13 | 1.32 | 1.50 | 2.50 |
| 0.69 | 0.88 | 1.07 | 1.26 | 1.46 | 1.65 | 2.48 |
| 0.79 | 0.99 | 1.20 | 1.40 | 1.60 | 2.50 | 2.49 |
| 0.14 | 0.23 | 0.80 | 0.80 | 0.81 | 0.97 | 1.14 |
| 0.00 | 0.14 | 0.60 | 0.77 | 0.94 | 1.12 | 2.50 |

Fig. 14q

| | | | | | | |
|---|---|---|---|---|---|---|
| 0.00 | 0.12 | 0.24 | 0.90 | 1.08 | 2.14 | 2.47 |
| 0.46 | 0.65 | 0.84 | 1.03 | 1.22 | 1.42 | 2.46 |
| 0.56 | 0.76 | 0.96 | 1.16 | 1.36 | 2.17 | 2.48 |
| 0.00 | 0.08 | 0.24 | 0.41 | 0.57 | 0.74 | 0.91 |
| 0.10 | 0.00 | 0.35 | 0.54 | 0.71 | 2.22 | 2.50 |
| 0.00 | 0.04 | 0.05 | 0.14 | 0.85 | 1.04 | 2.47 |
| 0.10 | 0.15 | 0.00 | 0.17 | 0.47 | 1.18 | 2.40 |
| 0.00 | 0.53 | 0.13 | 0.28 | 1.13 | 1.49 | 2.44 |
| 0.12 | 0.00 | 0.00 | 0.18 | 0.34 | 0.51 | 0.68 |
| 0.02 | 0.07 | 0.04 | 0.05 | 0.48 | 0.66 | 2.35 |
| 0.02 | 0.07 | 0.04 | 0.05 | 0.62 | 0.80 | 2.35 |
| 0.02 | 0.01 | 0.08 | 0.11 | 0.14 | 0.58 | 2.34 |
| 0.00 | 0.03 | 0.03 | 0.09 | 0.15 | 0.63 | 2.38 |
| 0.00 | 0.00 | 0.00 | 0.00 | 0.11 | 0.28 | 0.45 |
| 0.02 | 0.04 | 0.00 | 0.05 | 0.19 | 0.43 | 0.60 |
| 0.00 | 0.00 | 0.04 | 0.06 | 0.16 | 0.64 | 2.26 |
| 0.00 | 0.01 | 0.01 | 0.03 | 0.07 | 0.29 | 1.98 |
| 0.02 | 0.00 | 0.03 | 0.04 | 0.12 | 0.17 | 2.35 |

METHOD AND SOFTWARE TO DETERMINE PROBABILITY OF SLEEP/WAKE STATES AND QUALITY OF SLEEP AND WAKEFULNESS FROM AN ELECTROENCEPHALOGRAM

FIELD OF THE INVENTION

The invention relates to the determination of the probability of sleep/wake states and quality of sleep and wakefulness from an electroencephalogram.

BACKGROUND TO THE INVENTION

Determining whether a patient/individual is awake or asleep is an essential first step in the analysis of sleep records obtained during investigation of sleep disorders. In some cases such investigations require only knowledge of whether the patient was awake or asleep. An example would be home monitoring for the diagnosis of sleep apnea. Here, if a patient does not show evidence of sleep apnea (e.g. dips in oxygen saturation, interrupted snoring) a diagnostic dilemma arises in that one does not know whether the negative study was because the patient did not sleep. In other cases, it is necessary to have a more comprehensive description of sleep, such as amount of time spent in each of the different sleep stages, which reflect the type rapid edge movement (REM vs. non-REM) and depth (stages N1, N2, N3) of sleep. This information is needed to evaluate the quality of sleep and is particularly useful in cases of excessive somnolence and insomnia. In the latter cases, distinguishing a sleep state from an awake state is a first step towards determining which stage the patient is in. Typically, once it is clear that the patient is asleep, decisions as to what sleep stage the patient is in is based on the presence of specific features in an electroencephalogram (EEG), Eye movements (EOG), intensity of chin muscle activity (chin EMG), among other findings.

Apart from analysis of formal sleep records, it is of considerable importance to be able to determine the level of vigilance in situations that require a high level of alertness such as during driving long distances, operating heavy machinery or equipment of critical nature such as air-traffic control. It is well known that decreased alertness, for example, as a result of boredom, alcohol, drugs, or sleep deprivation, are responsible for numerous driving and occupational accidents. There are different levels to what is considered as wakefulness. These range from fully alert to drowsy to having periods (a few seconds) of micro-sleep. Cognitive and motor performance is impaired as level vigilance decreases even if the subject is still technically awake. To my knowledge, there are currently no methods that identify different levels of wakefulness.

The present invention deals with a method for developing a continuous quantitative scale that describes the level of vigilance/consciousness across the whole spectrum from full alertness to the deepest sleep. When embedded in appropriate equipment this method can be used to a) evaluate the level of vigilance in situations requiring alertness, b) determine whether a subject is awake or asleep, c) determine the quality of sleep in sleep studies and, d) as an initial step in detailed sleep scoring with the subsequent steps relying on identification of the additional features using any of well described approaches in prior art. The current method does not cover steps to classify sleep into its various conventional stages. Rather, the current process generates a value (Probability of being awake ($P_W$); Odds Ratio Product (ORP)), which reflects the probability of any given section of the EEG record falling in a period that would be staged as awake by experienced scorers or by validated automatic scoring systems. I have established the presence of a clear negative correlation between this value ($P_W$, ORP) and depth of sleep as measured by conventional visual criteria. As such, P $P_W$/ORP can be used as a continuous scale that describes the quality of wakefulness or sleep in certain sections of the record or as a lumped average for the whole night. Every sleep technologist recognizes that within any given conventional sleep stage there is a continuum of sleep quality. For example, an EEG pattern that is now classified as stage N1 according to conventional criteria could be very close to an awake pattern on one end of the spectrum or very close to the deeper stage 2 on the other end. Likewise, there is a huge range of patterns in what is now classified as an awake state, ranging from full wakefulness to quite wakefulness, to wakefulness interrupted by mini-sleep periods, and so on. The use of this index ($P_W$ ORP) allows an expression of the quality of sleep on a continuous scale regardless of the conventional classification. It also can be used to reflect the overall quality of sleep in one number. This is much easier to understand and interpret than the conventional histogram of the different stages vs. time (the Hypnogram).

The current accepted practice for scoring sleep records is manual scoring by expert technologists. This is time consuming, and by extension, quite expensive. Manual scoring is also highly subjective with different experts producing different results. As indicated above, the EEC; pattern in many of the epochs (usually 30 seconds in length) are on the border between two stages (e.g. awake vs. N1). Some may score these epochs one way while others may score it another way. Also, there are large differences in how experts interpret the guidelines, which are often vague. Manual scoring is also an extremely tedious task and is often associated with gross errors related to inattention. Automation, accordingly, has many potential advantages, if it can be shown to be accurate.

Manual scoring of sleep relies primarily on visual appreciation of the different EEG patterns. There have been many attempts at automating EEG scoring but the results have not been up to what is required for acceptance. Virtually all automated methods rely on frequency analysis of the EEG. This analysis produces the power in different frequencies. The relevant frequency content of the EEG is 0.3 to 40 Hz. Any EEG pattern can be accurately described by the power spectrum of the EEG, namely the power in each of the relevant frequencies. Many previous approaches have been described that exploit the power spectrum of the EEG to arrive at sleep stages. These approaches typically use various complex signal analysis models. The problem is that there is a huge number of frequency spectra that could be called awake and another huge number of patterns that could fall in what the eye perceives as sleep, and so many patterns that could be called either by eye. A high power in the beta range (>14 Hz) may be present in full wakefulness or in the deepest sleep. Likewise, a high alpha power (7 to 14) could be present in wakefulness or in any of the other sleep stages. Thus, the interpretation of power in a given frequency must take into account the power in other relevant frequencies. Yet, as indicated earlier, the various combinations of powers that can be encountered during wakefulness or sleep are enormous and do not lend themselves to a unitary quantitative model. Hence in this invention we use an empiric approach by assigning codes to thousands of EEG frequency patterns and simply determining how often each code is found in epochs that expert scorers score as awake or asleep.

Once a reference resource is established (probability of each code to be scored awake or asleep), scoring of un-scored files simply entails determining the spectral code of selected EEG intervals and determining the probability of Sleep/Wake state by use of the reference resource.

SUMMARY OF THE INVENTION

1) The present invention takes a radically different approach to scoring the EEG for determining the level of vigilance or sleep. It starts by performing frequency analysis of the EEG on discrete time intervals (Bins; e.g. 3 seconds, but clearly other intervals may be used). Also, as done with other methods, the power or amplitude in certain ranges of frequency is combined to reduce the number of variables to a manageable level. For example, the total power in frequencies between 0.3 and 2.5 is added, giving the power in the slowest range of waves (generally called Delta power). The ranges need not conform to any conventional classification (e.g. Delta, Theta, alpha, sigma, beta1, beta 2) and may or not be overlapping. Clearly, the more ranges are used, the greater the resolution. But, this greatly affects the number of combinations to be rated and, by extension, processing time and number of files to be expertly scored to produce the reference resource (look-up table, equation . . . etc). In our preferred embodiment, we have selected four frequency ranges (0.3 to 2.33 Hz (Delta); 2.67 Hz to 6.33 Hz (Theta); 7.33 Hz to 14.00 Hz (Alpha/Sigma); and >14 Hz (Beta)). The frequency range from 6.67 to 7.00 was not included in the Theta power as some alpha waves in clearly awake regions can occasionally be seen in this range in some patients.

2) The next step is to assign the power or amplitude in each frequency range in each Bin a rank (expressed as a number, letter or symbol) that reflects its relative magnitude. This is basically a normalization process that takes into account the entire range of powers or amplitudes observed in the relevant frequency range across as many sleep studies as possible. For this step, a number of EEG studies (files) that represent the full spectrum of relevant clinical conditions are scored manually or by a validated automatic system. The power or amplitude in each frequency range (selected in step 1), is then determined in Bins of equal length in these reference files. For example, we used initially 40 files, each about 8 hours long or 9600 3-sec Bins (8*60*20), for a total of approximately 400,000 bins. These values were then sorted in ascending order. The entire range was broken into smaller ranges of equal number. Clearly any number of ranges can be used. In the extreme, the actual power in each Range may be used as the rank. The larger the number of ranges the better the resolution but the more processing power and time are required. We used 10 ranges and each range was assigned a rank (we used numerical rank, 0 to 9). Thus, we divided the entire range of Delta power in the 400,000 samples into 10 equal ranges, the lowest range (Rank 0) includes all values in the lowest 10 percentile and Rank 1 includes all values between the $10^{th}$ and $20^{th}$ percentile, and so on until Rank 9 which includes all values above the $90^{th}$ percentile. The same was done for the other frequency ranges. The result was a table (e.g. Table 1) that can be looked up to determine a Rank to assign to the power in each frequency range in the Bin being examined.

TABLE 1

| Rank | Delta | Theta | Alpha/Sigma | Beta |
|---|---|---|---|---|
| 0 | 5.85 | 4.55 | 3.0 | 0.95 |
| 1 | 9.38 | 6.97 | 4.6 | 1.3 |
| 2 | 13.67 | 9.63 | 6.2 | 1.68 |
| 3 | 19.48 | 12.9 | 8.1 | 2.11 |
| 4 | 28.01 | 17.15 | 10.4 | 2.63 |
| 5 | 41.93 | 22.98 | 13.3 | 3.33 |
| 6 | 66.76 | 31.37 | 17.3 | 4.36 |
| 7 | 117.71 | 44.64 | 23.5 | 6.19 |
| 8 | 258.26 | 70.84 | 36.1 | 10.91 |
| 9 | 258.27+ | 70.85+ | 36.08+ | 10.92+ |

This Table is a fixed look-up table in the software. It is based on our results analyzing 40 files obtained from two academic sleep laboratories. Clearly other tables can be used with different frequency groupings, different ranking procedure or different Bin widths. Also, in some laboratories, extrinsic noise or other technical differences can result in somewhat different table values if a large number of files from that laboratory were subjected to the same ranking procedure. An optional feature is therefore to have the ranking table used in a certain laboratory developed specifically from files generated by that laboratory to allow for the technical differences. A variety of Ranking tables can then be available in the library and the appropriate one is selected when scoring files from laboratories that do not subscribe to recommended guidelines for data acquisition or which have specific noise issues. However, we have found the above table to be satisfactory when used to score files from a variety of laboratories.

Optionally, a similar table can be developed if other (than spectral power) features of the EEG in the specified frequency ranges are used (e.g. amplitude, Mean Absolute Amplitude (MABs), Total Variation (TV) . . . etc). In this case, the reference files are processed to generate the feature selected, and the total range of the feature in the reference files is broken into a number of sub-ranges for use in assigning Bin Codes.

The software determines the power (or amplitude . . . etc) in each of the selected frequency ranges (4 ranges in the preferred embodiment) in consecutive Bins (3 seconds in the preferred embodiment). Each Bin is then assigned a 4-digit Code based on the value of the feature (power, amplitude . . . etc) in each frequency range and the corresponding ranks in the look up table. For example, by use of numerical ranks, as in the preferred embodiment, if the powers in the Delta, Theta, Alpha/Sigma and Beta ranges in a given Bin were 52, 10, 17, and 7, the Bin Code would be 6368. This Code then indicates that the power spectrum in this Bin is composed of moderate Delta, relatively low Theta, moderate Alpha/Sigma and High Beta. If letters or symbols are used instead of numbers, the Code is a series of letters and/or symbols that reflect the ranks in the different ranges. From the above description, it is clear that a large number of Bin Codes would result. By using 10 ranks in each of 4 frequency ranges, there results 10,000 different Bin Codes, representing 10,000 different frequency spectra. Clearly this number can be expanded or reduced by different manufacturers of the software. However, we found that this combination provides satisfactory resolution.

3) Determining the Awake/Sleep probability for each Bin Code ($P_W$, ORP): A large number of sleep files, which could be the same files used to develop the ranking tables, are scored manually, or by a validated automatic system, according to conventional criteria (e.g. the 2007 American Academy of Sleep Medicine guidelines). Each file is divided into consecutive bins of the same duration used to develop the ranking table. The Bin Code for each Bin is calculated from the Ranking table. For each Bin Code the fraction of occurrences of this Code in periods scored as awake by the expert technologists, or by the validated automatic system, is determined. For example, if there were 280 instances of Bin Code 1422 in the entire reference dataset and only 20 occurred in epochs staged as awake, the probability of Bins with this Code occurring in awake periods is given a value of 20/280, or 0.07 (or 7%). On the other hand, a Bin number that occurred only in epochs staged as awake by experts would be assigned a probability of 1.0 (or 100%).

In the preferred embodiment, we obtained conventional manual scoring of 40 files from two academic institutions. The scorer was a very senior certified technologist. She was asked to score each 30-sec epoch as carefully as possible, with no time constraints, using the latest scoring guidelines (AASM 2007 guidelines). The scoring of sleep stages and arousals was reviewed by the inventor and a consensus was reached in epochs where there were differences. The files were broken into 3-sec Bins for an approximate total of 400,000 Bins. Bin Codes were assigned as per step 2. The probability of each of the Bin Codes occurring during epochs scored manually as awake or within scored arousals was determined for each Bin Code. The average number of occurrences of any Bin Code in this data set was 400,000/10,000 or 40. However, as may be expected, there were some Bin Codes that were very frequent (e.g. Bin Codes 0000 and 9999, which occurred several thousand times) and others that were absent or extremely rare. 6200 Bin Codes occurred >10 times in the dataset and their probability could be determined directly (# awake/total #), while 1000 Bin Codes were completely absent and 2800 Codes occurred only 1-10 times. For these, arbitrary probability values were assigned manually based on their spectral pattern (BIN Code) and the probability of fairly similar Bin Codes that have directly determined probabilities. For example, Bin Codes 1190, 1191, 1192 and 1193 were very poorly represented in the data set (0 to 8 Bins out of 400,000). However, the immediately following bin code (1194) with only slightly higher beta power had good representation (209) and its ORP was 2.5 ($P_W$=100%). Furthermore, Bin codes with the same beta rank (0, 1, 2 and 3) but slightly lower alpha rank (namely 1180, 1181, 1182, and 1183) also had a very high ORP values thereby indicating that Bins with very low Delta and Theta powers and high Alpha power occur almost invariably in awake epochs, regardless of Beta rank. Accordingly, the four Bin Codes with little or no representation were assigned a probability of 95%. Clearly with time, the number of files subjected to this process can be increased to obtain a much larger dataset in which fewer Bin Codes are poorly represented. It must be pointed out that because these Bin Codes are quite rare, errors in the assigned arbitrary probabilities would have minimal consequences. Thus, as an alternative to assuming ORP values in poorly represented bin codes, it may be reasonable to not assign any ORP value to such bin codes or to assign a default value that would indicate that this 3-sec epoch should not be considered in any subsequent analysis.

From the above steps, a table was generated that contained the probability of being awake for each of the 10,000 Bin Codes. Although the probability values can be used as such (0 to 1.0 or 0 to 100%), we elected to use a different scale where a probability of 40% is assigned a value of 1.0 and other probabilities are assigned a value of (Probability %)/40. This was because we found that 40% of all 30-second epochs in the reference files were scored awake. So, the odd of being correct if awake is scored at random is 40%. We arbitrarily decided to express all probability values as a ratio (ORP). Thus, a probability of 100% of being awake is given an ORP of 2.5 and a probability of 10% of being awake is given an ORP of 0.25. Clearly which of the 3 scales to use (fraction, percent, or ORP) is optional as they all reflect the same thing.

10015) A table was developed that contained the ORP value for each of the 10,000 Bin Codes (ORP table; FIG. 14). Table 2 below shows the ORP values for the first and last 300 bin codes. Clearly the higher the ORP value the greater the likelihood of the Bin occurring in an epoch that would manually be scored as awake, and vice versa. Further, the ORP (or probability) value should reflect the depth of sleep. For example, an ORP value of 1.25 (probability of falling in an epoch scored awake=50%) means that a Bin with such a spectral pattern occurs equally in epochs scored as awake or asleep. Such Bin Code must, therefore, reflect very light sleep because sleep depth is typically a gradual process. It is true that in some 30-second epochs deep sleep can suddenly change to awake. However, these instances are quite infrequent when viewed within the context of several hundred thousand Bins in representative files. Conversely, an ORP that is close to zero indicates that such a spectral pattern is only seen in sleep and, hence, occurs only in very stable sleep, which is typically deep sleep.

Once the Bin Codes are assigned as per step 2, the software converts the Codes into probabilities by use of the Probability Look-up table. An example of such conversion for bin code 0126 is shown in Table 2. It is theoretically possible to express the results of Table 2 as a mathematical formula through complex regression analysis. In such case, the formula can be used to convert the Code into probability instead of the look-up table. We have found that such an exercise of attempting to fit the data of Table 2 by a formula is not warranted in view of the ease and speed of utilizing a look-up table. However, use of formulae or other decoding instruments to convert the Codes into probabilities is covered by the present invention.

The ORP table given here is unique to the reference files we used, the scorers who scored these files, the frequency bands and frequency domain analysis used, bin width (3-seconds), the ranking method used (Table 1), and the output form (ORP). We have obtained excellent results using this combination of techniques and look-up tables (Kuna S T, Benca R, Kushida C A, Walsh J, Younes M, Staley B, Hanlon A, Pack A I, Pien G W, Malhotra A. Agreement in Computer-Assisted Manual Scoring of Polysomnograms Across Sleep Centers. SLEEP 36:583-589, 2013). However, and as mentioned earlier, a software manufacturer may choose to apply the general method described here using other reference files, other scorers, other methods of frequency domain analysis, other frequency bands, another ranking system or output form (e.g. % awake) and generate their own look-up tables. In such cases the Ranking and Probability tables should be constructed from reference files that were analyzed using the same methods (i.e. frequency ranges, bin width, frequency domain analysis . . . etc). Such different applications of the general method fall within the scope of this invention.

TABLE 2

Representative ORP Values For the First and Last 300 Bin Codes

| Bin Code | 0 | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| 0000 | 0.92 | 1.80 | 1.88 | 1.95 | 2.05 | 2.13 | 2.27 | 2.39 | 2.50 | 2.50 | 1.33 | 1.72 | 2.02 | 2.14 | 1.97 | 2.08 | 2.26 | 2.42 | 2.43 | 2.50 |
| 0020 | 1.81 | 2.21 | 2.28 | 2.24 | 2.32 | 2.24 | 2.30 | 2.39 | 2.46 | 2.50 | 2.30 | 2.30 | 2.31 | 2.39 | 2.37 | 2.39 | 2.34 | 2.41 | 2.45 | 2.50 |
| 0040 | 1.98 | 2.38 | 2.40 | 2.47 | 2.44 | 2.42 | 2.45 | 2.41 | 2.46 | 2.49 | 2.50 | 2.39 | 2.46 | 2.46 | 2.48 | 2.50 | 2.49 | 2.45 | 2.49 | 2.50 |
| 0060 | 2.30 | 2.27 | 2.50 | 2.49 | 2.49 | 2.47 | 2.49 | 2.49 | 2.48 | 2.49 | 2.30 | 2.37 | 2.41 | 2.50 | 2.50 | 2.47 | 2.49 | 2.48 | 2.49 | 2.50 |
| 0080 | 2.30 | 2.50 | 2.43 | 2.44 | 2.50 | 2.49 | 2.49 | 2.50 | 2.50 | 2.50 | 2.30 | 2.30 | 2.30 | 2.50 | 2.50 | 2.50 | 2.50 | 2.50 | 2.50 | 2.50 |
| 0100 | 0.26 | 0.52 | 0.78 | 0.78 | 1.03 | 1.38 | 1.64 | 1.93 | 2.20 | 2.50 | 0.48 | 0.80 | 0.78 | 0.95 | 0.97 | 1.15 | 1.63 | 1.97 | 2.32 | 2.50 |
| 0120 | 1.10 | 1.11 | 1.34 | 1.51 | 1.68 | 1.52 | 1.85 | 2.13 | 2.32 | 2.50 | 1.50 | 1.60 | 1.71 | 1.85 | 2.08 | 1.94 | 2.18 | 2.21 | 2.39 | 2.41 |
| 0140 | 1.60 | 1.60 | 1.90 | 2.24 | 2.28 | 2.27 | 2.25 | 2.24 | 2.30 | 2.47 | 2.00 | 2.00 | 2.16 | 2.40 | 2.29 | 2.48 | 2.34 | 2.45 | 2.42 | 2.50 |
| 0160 | 2.20 | 2.20 | 2.32 | 2.39 | 2.42 | 2.43 | 2.33 | 2.44 | 2.48 | 2.50 | 2.30 | 2.30 | 2.50 | 2.47 | 2.44 | 2.43 | 2.45 | 2.49 | 2.47 | 2.49 |
| 0180 | 2.50 | 2.50 | 2.50 | 2.50 | 2.47 | 2.50 | 2.49 | 2.49 | 2.48 | 2.50 | 2.50 | 2.50 | 2.50 | 2.50 | 2.50 | 2.50 | 2.50 | 2.48 | 2.50 | 2.50 |
| 0200 | 0.19 | 0.28 | 0.35 | 0.66 | 0.63 | 0.46 | 0.80 | 1.60 | 2.00 | 2.20 | 0.24 | 0.28 | 0.37 | 0.62 | 0.48 | 0.58 | 0.80 | 1.80 | 2.35 | 2.50 |
| 0220 | 0.50 | 0.56 | 0.81 | 1.00 | 1.15 | 1.30 | 1.45 | 1.60 | 2.15 | 2.30 | 0.80 | 0.80 | 0.80 | 1.04 | 1.28 | 1.52 | 1.76 | 1.96 | 2.03 | 2.50 |
| 0240 | 1.28 | 1.40 | 1.52 | 1.64 | 2.04 | 1.97 | 1.81 | 2.00 | 2.31 | 2.50 | 1.55 | 1.65 | 1.75 | 1.85 | 2.19 | 2.29 | 2.11 | 2.21 | 2.30 | 2.50 |
| 0260 | 1.82 | 1.90 | 1.98 | 2.08 | 2.34 | 2.29 | 2.23 | 2.42 | 2.47 | 2.47 | 2.09 | 2.15 | 2.21 | 2.20 | 2.43 | 2.39 | 2.45 | 2.37 | 2.48 | 2.48 |
| 0280 | 2.36 | 2.40 | 2.44 | 2.37 | 2.44 | 2.46 | 2.46 | 2.44 | 2.47 | 2.50 | 2.50 | 2.50 | 2.50 | 2.50 | 2.50 | 2.50 | 2.50 | 2.47 | 2.49 | 2.50 |
| 0300 | 0.16 | 0.30 | 0.15 | 0.31 | 0.16 | 0.80 | 1.00 | 1.19 | 1.38 | 1.57 | 0.14 | 0.25 | 0.32 | 0.18 | 0.24 | 0.36 | 1.17 | 1.35 | 1.52 | 1.69 |
| | | | | | | | | Example: ORP for Bin Code 0126 = 1.85 | | | | | | | | | | | | |
| 9700 | 0.00 | 0.00 | 0.00 | −0.14 | 0.02 | 0.18 | 0.34 | 0.51 | 0.67 | 0.83 | 0.00 | 0.00 | 0.00 | 0.00 | 0.08 | 0.24 | 0.41 | 0.57 | 0.74 | 0.91 |
| 9720 | 0.00 | 0.00 | 0.00 | 0.00 | 0.00 | 0.30 | 0.47 | 0.64 | 0.81 | 0.99 | 0.00 | 0.00 | 0.00 | 0.10 | 0.00 | 0.35 | 0.54 | 0.71 | 2.22 | 2.50 |
| 9740 | 0.00 | 0.00 | 0.00 | 0.00 | 0.00 | 0.16 | 0.28 | 0.78 | 2.13 | 2.50 | 0.00 | 0.00 | 0.00 | 0.00 | 0.04 | 0.05 | 0.14 | 0.85 | 1.04 | 2.47 |
| 9760 | 0.00 | 0.00 | 0.00 | 0.00 | 0.12 | 0.04 | 0.16 | 0.50 | 1.11 | 2.44 | 0.00 | 0.00 | 0.00 | 0.10 | 0.15 | 0.00 | 0.17 | 0.47 | 1.18 | 2.40 |
| 9780 | 0.80 | 0.00 | 0.00 | 0.00 | 0.06 | 0.04 | 0.19 | 0.40 | 1.19 | 2.44 | 0.00 | 0.00 | 0.13 | 0.00 | 0.53 | 0.13 | 0.28 | 1.13 | 1.49 | 2.44 |
| 9800 | 0.00 | 0.13 | 0.00 | 0.00 | 0.00 | 0.00 | 0.11 | 0.28 | 0.44 | 0.60 | 0.00 | 0.00 | 0.00 | 0.12 | 0.00 | 0.00 | 0.18 | 0.34 | 0.51 | 0.68 |
| 9820 | 0.00 | 0.00 | 0.04 | 0.00 | 0.00 | 0.21 | 0.17 | 0.41 | 0.58 | 0.75 | 0.00 | 0.00 | 0.00 | 0.02 | 0.07 | 0.04 | 0.05 | 0.48 | 0.66 | 2.35 |
| 9840 | 0.00 | 0.00 | 0.04 | 0.00 | 0.00 | 0.21 | 0.17 | 0.55 | 0.73 | 0.91 | 0.00 | 0.00 | 0.00 | 0.02 | 0.07 | 0.04 | 0.05 | 0.62 | 0.80 | 2.35 |
| 9860 | 0.00 | 0.00 | 0.00 | 0.00 | 0.03 | 0.04 | 0.10 | 0.11 | 0.65 | 2.35 | 0.00 | 0.00 | 0.00 | 0.02 | 0.01 | 0.08 | 0.11 | 0.14 | 0.58 | 2.34 |
| 9880 | 0.00 | 0.00 | 0.00 | 0.00 | 0.05 | 0.04 | 0.04 | 0.10 | 0.46 | 2.28 | 0.00 | 0.00 | 0.00 | 0.00 | 0.03 | 0.03 | 0.09 | 0.15 | 0.63 | 2.38 |
| 9900 | 0.00 | 0.00 | 0.00 | 0.00 | 0.00 | 0.00 | 0.00 | 0.05 | 0.21 | 0.37 | 0.00 | 0.00 | 0.00 | 0.00 | 0.00 | 0.00 | 0.00 | 0.11 | 0.28 | 0.45 |
| 9920 | 0.00 | 0.00 | 0.00 | 0.00 | 0.00 | 0.00 | 0.01 | 0.18 | 0.35 | 0.52 | 0.00 | 0.00 | 0.00 | 0.02 | 0.04 | 0.00 | 0.05 | 0.19 | 0.43 | 0.60 |
| 9940 | 0.00 | 0.00 | 0.01 | 0.01 | 0.03 | 0.02 | 0.03 | 0.26 | 0.50 | 0.68 | 0.00 | 0.00 | 0.00 | 0.00 | 0.00 | 0.04 | 0.06 | 0.16 | 0.64 | 2.26 |
| 9960 | 0.00 | 0.00 | 0.00 | 0.00 | 0.00 | 0.02 | 0.03 | 0.13 | 0.50 | 2.23 | 0.00 | 0.00 | 0.00 | 0.00 | 0.01 | 0.01 | 0.03 | 0.07 | 0.29 | 1.98 |
| 9980 | 0.00 | 0.00 | 0.00 | 0.01 | 0.01 | 0.01 | 0.03 | 0.07 | 0.16 | 1.94 | 0.00 | 0.00 | 0.00 | 0.02 | 0.00 | 0.03 | 0.04 | 0.12 | 0.17 | 2.35 |

This Patent application is about generating a probability estimate of an electroencephalogram interval (Bin) falling in an epoch that would be scored independently, by expert scorers or systems, as awake. Clearly, rather than estimating the probability of being awake, one may choose to estimate the Probability of the epoch being scored as asleep. (this would simply be (2.5-ORP), or (100 Probability %)).

The probability value generated by the current invention can be used in many different ways:

A) The average Probability Estimate (e.g. ORP) for the entire file can be displayed in the scoring report, and used as a measure of overall sleep quality.

B) The average Probability Estimate for periods scored as specific sleep stages (manually or automatically) can also be displayed in the scoring report. It is generally recognized that a given sleep stage is not homogeneous. Within each sleep stage there is a spectrum of EEG patterns with some being closer to awake patterns while others are closer to deep sleep. Stage N2 in one patient may, for example, have a predominance of deeper sleep Bins or epochs while in another patient lighter sleep epochs predominate. These differences are not currently captured by conventional scoring, which classifies sleep into 4 stages only. By reporting the quality of sleep within each of the four stages, it may be possible to explain why some patients symptoms (fatigue, sleepiness) are not in keeping with the results of conventional scoring. We have found that the $P_W$ in stage N1 sleep ranges from 24% to 72% (ORP 0.6 to 1.8) among different subjects, for N2 the range was 7% to 55% (ORP 0.17 to 1.4), and for N3 it was 2% to 28% (ORP 0.04 to 0.7). It is thus clear that within the same stage defined by visual criteria, there is a wide range of ORP values that reflect different levels of sleep quality.

C) Likewise, within what is conventionally scored as awake time, the average $P_W$ can range from 62% to 96% (ORP 1.55 to 2.40), thereby reflecting different degrees of vigilance during what is conventionally called awake. It can be easily envisioned that a limited EEG monitoring device, attached to the forehead for example, can be equipped with the current software and be used to monitor $P_W$ or ORP in real time in subjects engaged in critical activities. Such a system can also sound an alarm or notify monitoring stations when $P_W$ or ORP falls below a specified level (e.g. 2.2).

D) The probability estimates can be averaged over periods on and off therapy and the averages reported to show the effect of therapy on sleep quality.

E) The probability estimate can be used on its own to score sleep if all that is required is to determine whether the epoch(s) being scored are simply awake or asleep. For example, the average probability estimate for all Bins within a 30-second interval can be calculated. I have found that by using the simple rule of scoring an epoch awake when average ORP is >1.6 (probability >64%), and vice versa, the scoring is accurate in 95% of epochs. This is acceptable accuracy for that purpose.

F) Alternatively, the distribution of probability estimates within an epoch (e.g. 30 seconds) can be utilized to improve accuracy, particularly in epochs in which the average ORP is equivocal. For example, a 30-second epoch that contains four 3-second Bins with an ORP <1.0 and six 3-second Bins with an ORP >2.0 might have an ambivalent average ORP of 1.4. However, it would be scored as awake since this was clearly an epoch split between a longer period with a dominant awake pattern (ORP>2.0) and a shorter period with sleep pattern. Several other algorithms that examine the pattern of ORP values within a 30-second epoch can clearly be utilized to improve the accuracy of distinguishing between awake and asleep in an epoch. While we prefer that the software make a decision in every 30-sec epoch, one option is to not score epochs where it is difficult to decide. For example, if all ORP values within an epoch are in the mid-range (1.2 to 1.8) and the average is also equivocal (e.g. 1.2 to 1.6), one may elect to identify the epoch as un-storable by the current system. This would affect only a small minority of epochs.

G) The current invention can be used as an accessory to the current manual scoring systems. Thus, the file would be run first with the software of the current invention to automatically classify epochs as awake or asleep, to be followed by manual scoring of the different sleep stages.

H) The probability estimate can be incorporated within software that performs comprehensive sleep staging. Here, after the overall status of an epoch (sleep vs. awake), epochs scored as sleep are further identified as one of the standard four stages (Rem, N1, N2, N3) using additional algorithms to detect features used for classifying sleep stages (e.g. eye movements, spindles, K complexes, chin EMG). Such steps that aim to further identify the different stages of sleep are not part of this invention.

I) The current invention can be incorporated in portable devices that measure the EEG. The results can be displayed or transmitted (wirelessly or through cable) in real time. In this way the results can help evaluate the state of vigilance of the subject being monitored.

Accordingly, in one aspect of the present invention, there is provided a method method for generating a Probability index (Index) that reflects where an electroencephalogram (EEG) pattern lies within the spectrum of wakefulness to deep sleep, which employs a computer/microprocessor that performs frequency domain analysis of one or more discrete sections (Bins) of the EEG to determine the EEG power at specified frequencies, optionally calculates the total power over specified frequency ranges (Ranges), assigns a rank to the power at each frequency, or frequency Range, assigns a code to the Bin that reflects the ranking of the different frequencies or frequency ranges (Bin Code), and determines an index that reflects where said EEG pattern within said Bin(s) lies within the spectrum of wakefulness to deep sleep by use of a Reference Source, such as a look-up table or other suitable decoding instrument, where such Reference Source is obtained by calculating the probability of Bins with different Codes occurring in epochs scored as awake or asleep in reference files scored by one or more expert technologists or by an automatic scoring software.

In that method, material of calculating power, frequency domain analysis is used to calculate signal amplitude, or other measure of signal strength, in the specified frequency ranges and where the Ranking method and the Reference Source are based on use of the method of calculating signal strength.

In another aspect of the present invention, there is provided software for estimating the Probability that the electroencephalogram (EEG) pattern reflects a sleeping or awake state, said software executing the following functions performing spectral analysis of one or more discrete sections (Bins) of the EEG to determine the EEG power at different frequencies, optionally calculating the total power over specified frequency ranges (Ranges), assigning a rank to the power at each frequency, or frequency Range, assigning a code to the Bin that reflects the ranking of the different frequencies or frequency ranges (Bin Code), and determining the probability of the EEG pattern within said Bin(s) of reflecting an awake or sleep state by use of a reference source, such as a look-up table or other suitable decoding instrument, where such reference source is obtained by calculating the probability of Bins of different Codes occurring in epochs scored as awake or asleep in reference files scored by one or more expert technologists or by a properly validated scoring software.

. . . claim 9.

In a further aspect of the present invention, there is provided a device for carrying out the method and utilizing the software.

BRIEF DESCRIPTION OF DRAWINGS

FIGS. 11a-d shows details of the Front End Analog Circuitry of the instrument of FIG. 10;

FIGS. 13a-d shows details of the power supply and associated circuitry for the instrument of FIG. 10; and FIGS. 14a-q is the ORP Table.

DESCRIPTION OF PREFERRED EMBODIMENTS

1) Analysis of Pre-Existing Records:

This form of implementation is particularly suitable when this invention is used on pre-existing files or when the generation of the Probability Value is a preliminary step to be followed by more detailed analysis of the EEG that require examination of large sections of the file (e.g. as an aid to scoring sleep stages). This form of implementation is preferably done on standard computers.

The software of the preferred embodiment was developed in C# (C sharp) on a standard desktop computer with the following specifications:

1) Processor: 3.4 GHz
2) RAM: 4 GB

Figure 1:
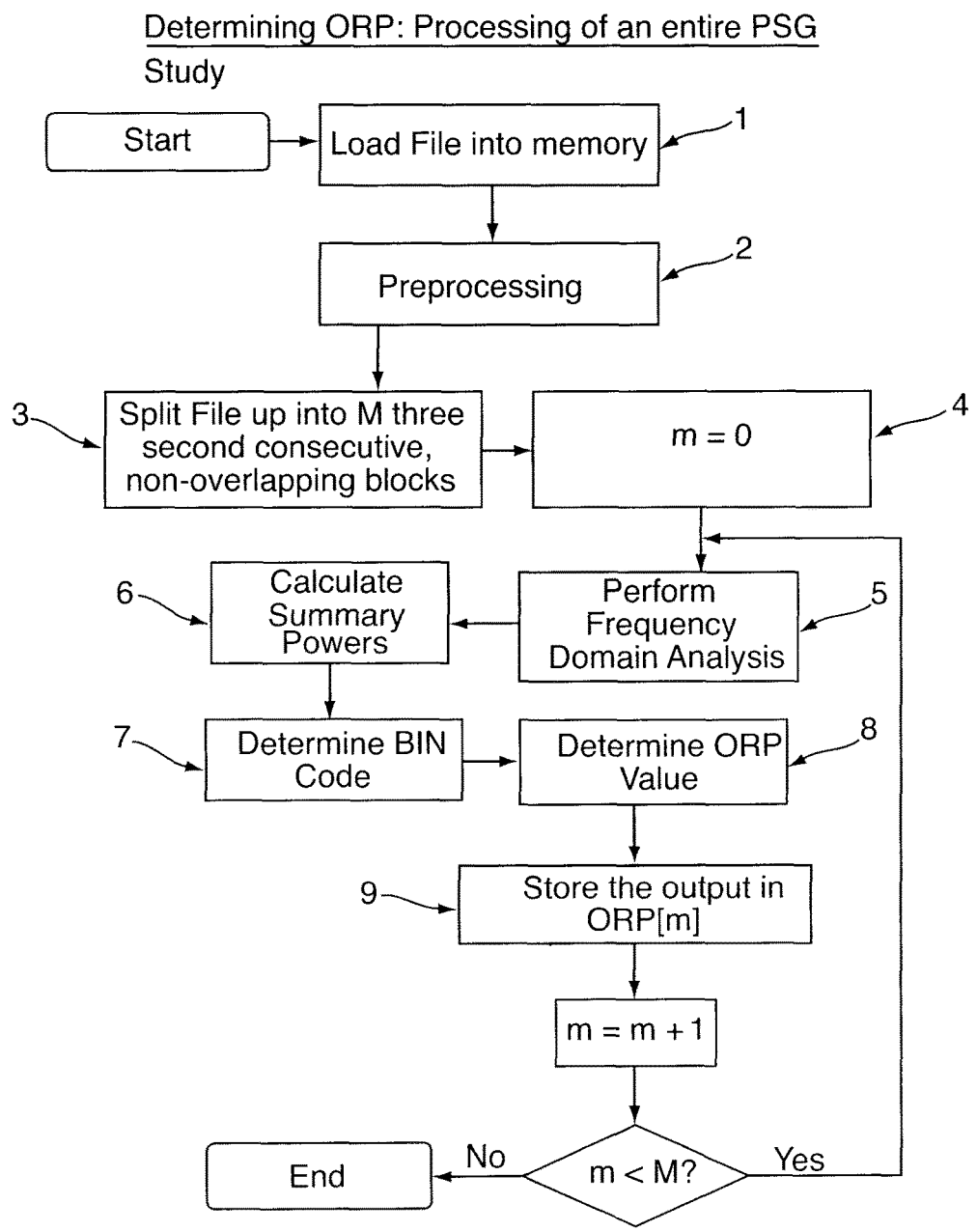
FIG. 1 is a block diagram of the major components of software and the data flow in the analysis of processing records to determine ORP.

3) Operating System: Windows XP, 32-bit
4) Development Environment: Visual Studio 2008
5) Hard Drive Size: 1.00 TB FIG. 1 is a block diagram of the major components of the software and the data flow. The file is loaded in memory (1). The next step involves optional pre-processing (2) (See FIG. 2). The file is then split into 3-sec bins (3) with a total number, M, corresponding to ⅓ file length in seconds. Beginning with the first bin (4) frequency domain analysis is performed (5) (sec FIG. 4) followed by calculation of total power in different frequency ranges (6) (see FIG. 5). From this, bin code is assigned (7) by reference to lookup table 1, which is stored in memory. This is followed by determination of ORP for the 3-sec bin (8) (see FIG. 7), by reference to the stored ORP lookup table. The ORP value is stored (9). Bin number is increased by one and the process repeats until the end of the file.

Figure 2:
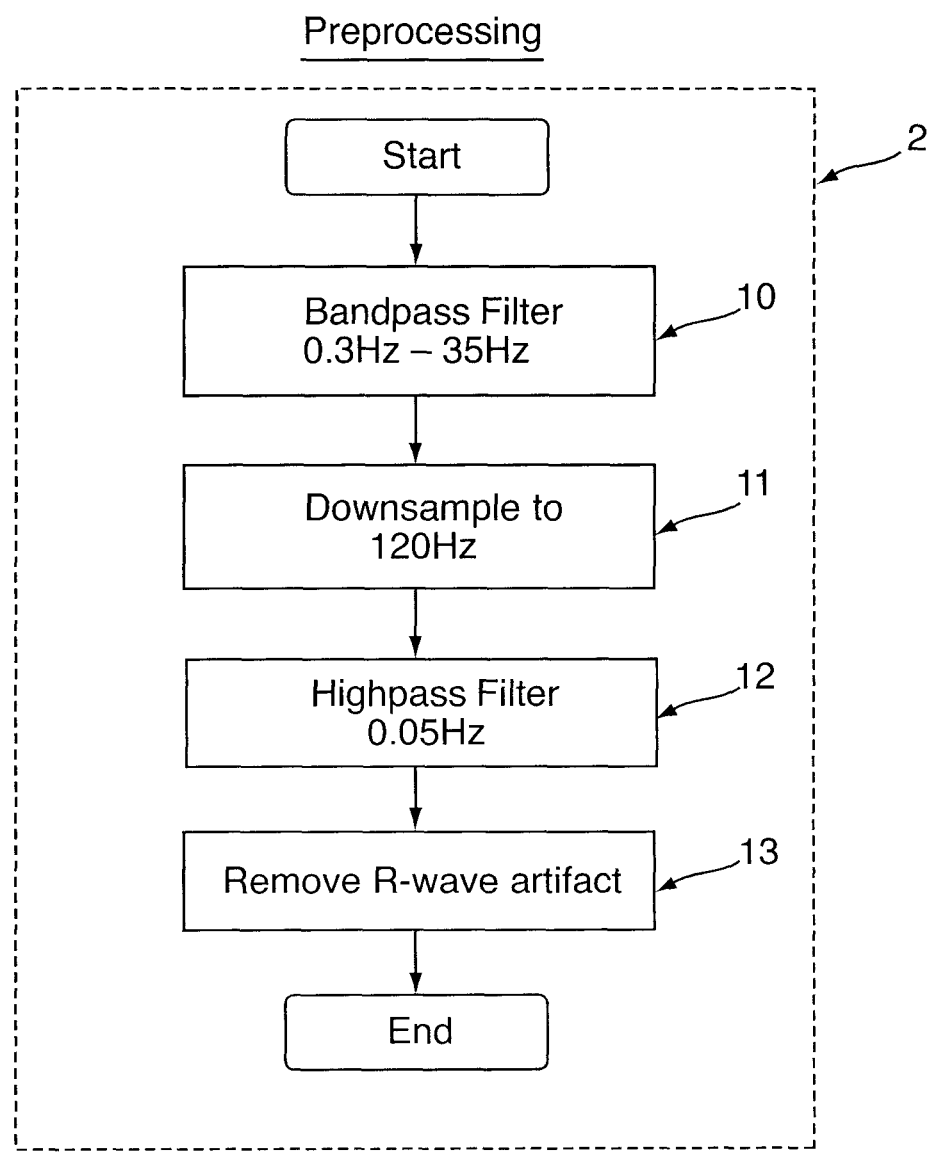
FIG. 2 is a block diagram showing various pre-processing options.

FIG. 2 shows the various pre-processing options (2). One or more of these is executed depending on the pre-existing properties of the file. These properties are inputted into the computer along with the file.

The hand-pass filter (0.3-35.0 Hz) option (10) is applied if the file in memory is not pre-filtered. This is to comply with recommended standards for processing of the EEG. The current software operates on the assumption that the sampling frequency in the file is 120 Hz. If the sampling frequency is <120 Hz, the file is rejected. If >120 Hz, the data is re-sampled at 120 Hz (11) using the "Nearest Neighbor Approximation" (the value of the data point nearest the time required for 120 Hz is used). This is followed by a 0.05 high-pass filter (12). Finally, if the R wave artifact of the electrocardiogram (EKG) has not been filtered out in the stored file, an R-wave artifact removal algorithm is applied to the EEG signal (13). This requires the presence of an EKG channel in the file.

Figure 3:
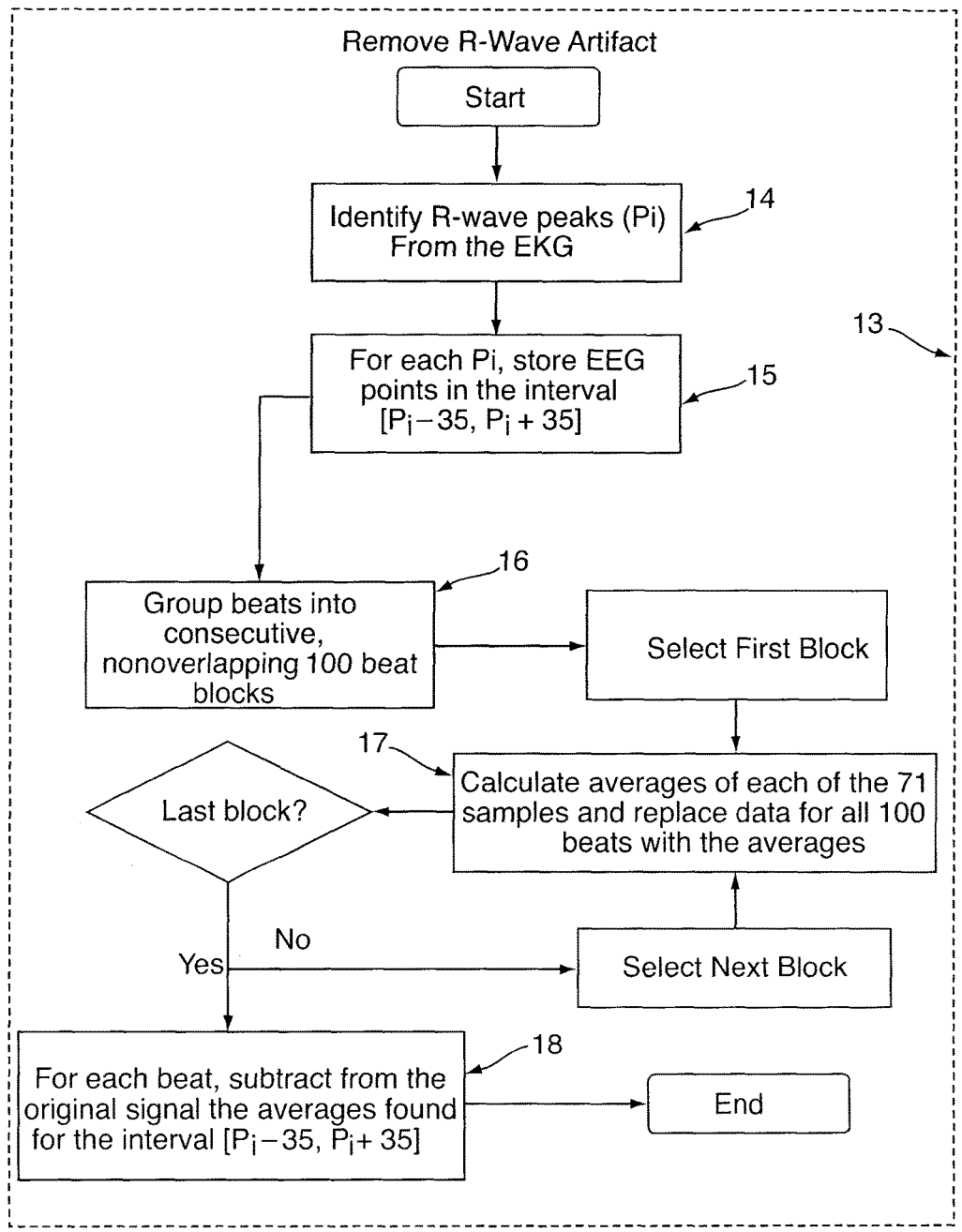
FIG. 3 is a block diagram of the algorithm for removing the R-wave artifact.

Details of this R-wave artifact removal algorithm are shown in FIG. 3. Briefly, the times of R wave peaks (Pi) are located for each cardiac beat in the file (14). Any of a number of standard R wave detection algorithms can be used. For this embodiment, a 5-point derivative of the EKG signal is obtained and then squared. An 11-point integral is performed on the squared derivative (IFRDi). A 10-sec integral of the IFRD is obtained (IFRD$_{10s}$) and the difference between IFRDi and IFRD$_{10s}$ is calculated. Peak R wave is identified as the highest point in a transient in which IFRDi >IFRD$_{10s}$ for >100 ms. Subsequent steps are performed on the EEG channel from which the R wave artifact is to be removed. EEG data in the interval Pi±35 points (≈0.6 sec) of each R wave are stored (15). These stored values are then broken into consecutive blocks, each containing 100 beats (16). The average of the 100 sets of 71 points is then obtained for each block and this 71-point average replaces all 100 sets in the block (17). This process is performed for each block in the file. Finally, the stored averages are subtracted from the original EEG data (18).

Figure 4:
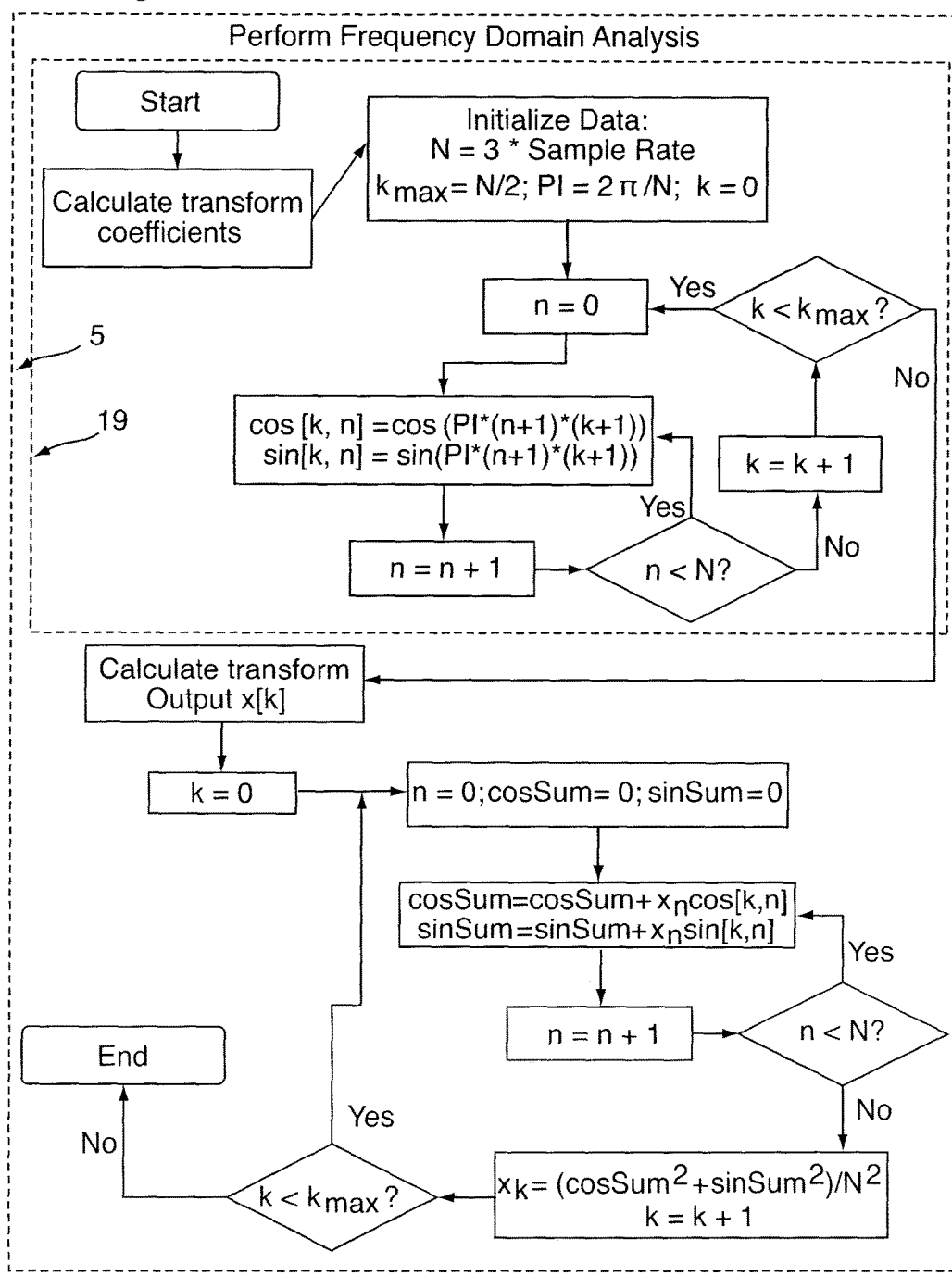
FIG. 4 is a block diagram showing the steps used for Frequency domain analysis.

FIG. 4 shows the steps used for Frequency domain analysis (5). Our software, which uses a variation of the Fourier transform, calculates the power X[k] at frequency k as:

$$\left[A[k] = \sum_{n=0}^{n-1} x n \cos\left(\frac{2\pi}{N}(k+1)(n+1)\right)\right]$$

$$\left[B[k] = \sum_{n=0}^{n-1} x n \sin\left(\frac{2\pi}{N}(k+1)(n+1)\right)\right]$$

$$X[k] = ((A[k])^2 + (B[k])^2)/N^2$$

For integer values of k, $$k = \left[1, \frac{N}{2}\right]$$

$$k = \left[1, \frac{N}{2} - 1\right]$$

Where;
$f_s$=Sample Rate of the EEG window=120 Hz
N=Length of input EEG window, in samples=$3f_s$=360
n=Current sample index in EEG window
$x_n$=Value of the EEG signal for sample n
k=Index of the frequency we are examining. The actual frequency is:

$$f_k = \frac{(k+1)}{3} Hz$$

$$f_k = \frac{(k+1)}{3} Hz$$

X[k]=The power at a frequency index of k
C=Scaling coefficient, equal to $$\frac{1}{N} = \frac{1}{360}$$

To save computation time, since the following two terms $$\cos\left(\frac{2\pi}{N}(k+1)(n+1)\right)$$

$$\sin\left(\frac{2\pi}{N}(k+1)(n+1)\right)$$

are independent of $x_n$, and as shown in the top of FIG. 4 (19), they are calculated ahead of time and stored in memory.

Figure 5:
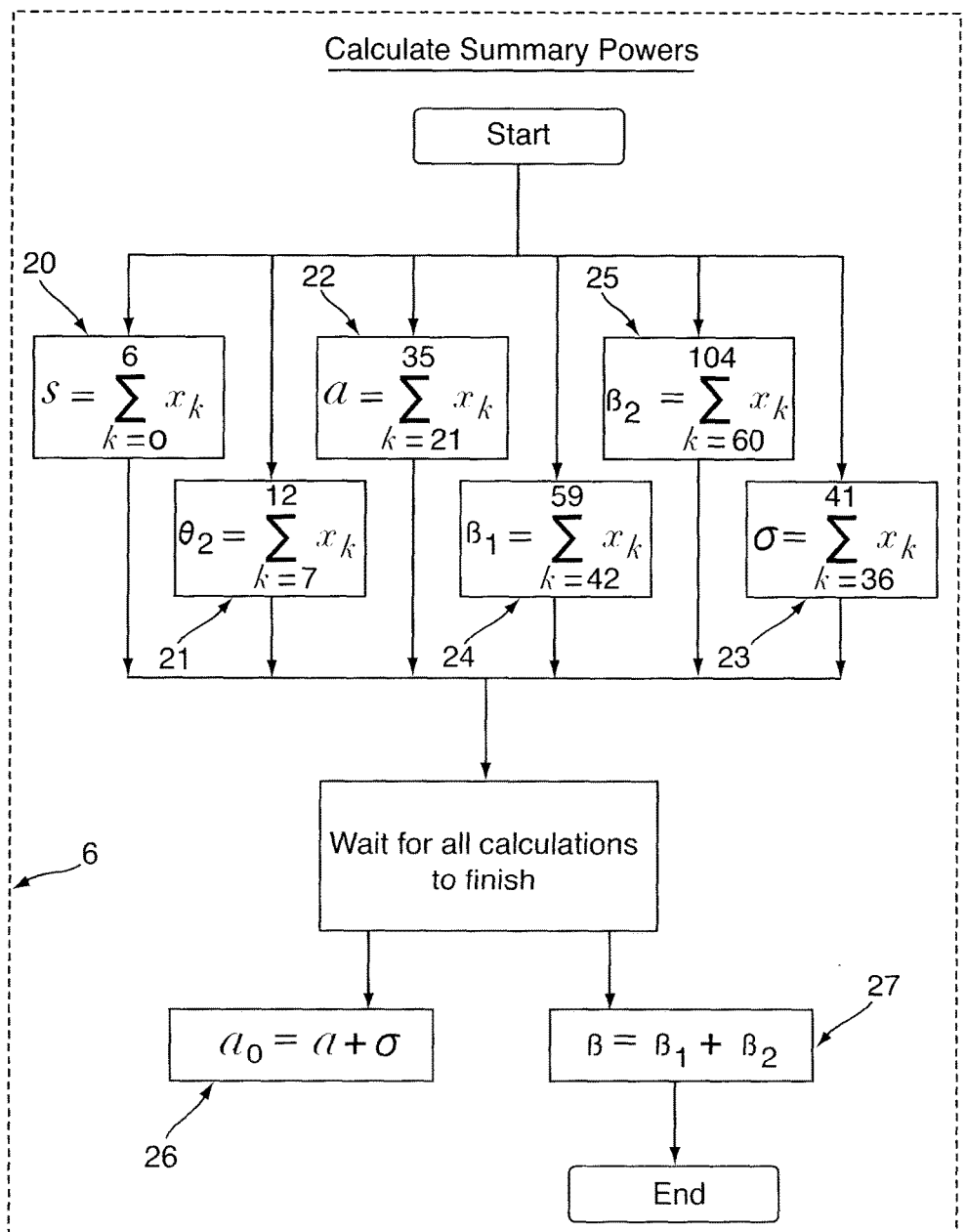
FIG. 5 is a flow chart of the step of "Calculate Summary Powers"

FIG. 5 is a flow chart describing the step "Calculate Summary Powers" (6). In this step the sum of powers in specified frequency ranges is calculate in each 3-sec bin. The frequency ranges used in this embodiment were (6):
  0.3-2.3 Hz (k=0-6): corresponding to conventional delta range (20);
  2.7-6.3 Hz (k=7-18): corresponding to conventional delta range, excluding frequencies 6.7 and 7.0 Hz (21);
  7.3-12.0 Hz (k=21-35): corresponding to conventional alpha range (22),
  12.3-14.0 Hz (k=36-41): corresponding to conventional sigma range (23), 14.3-20.0 (k=42-59): corresponding to conventional Beta1 range (24), and 20.3-35.0 (k=60-104): corresponding to conventional Beta2 range (25).

For the sake of ORP determination, alpha and sigma powers were combined (alpha/sigma power (26)) and beta 1 and beta 2 powers were also combined (beta power (27)), resulting in 4 frequency ranges.

Figure 6:
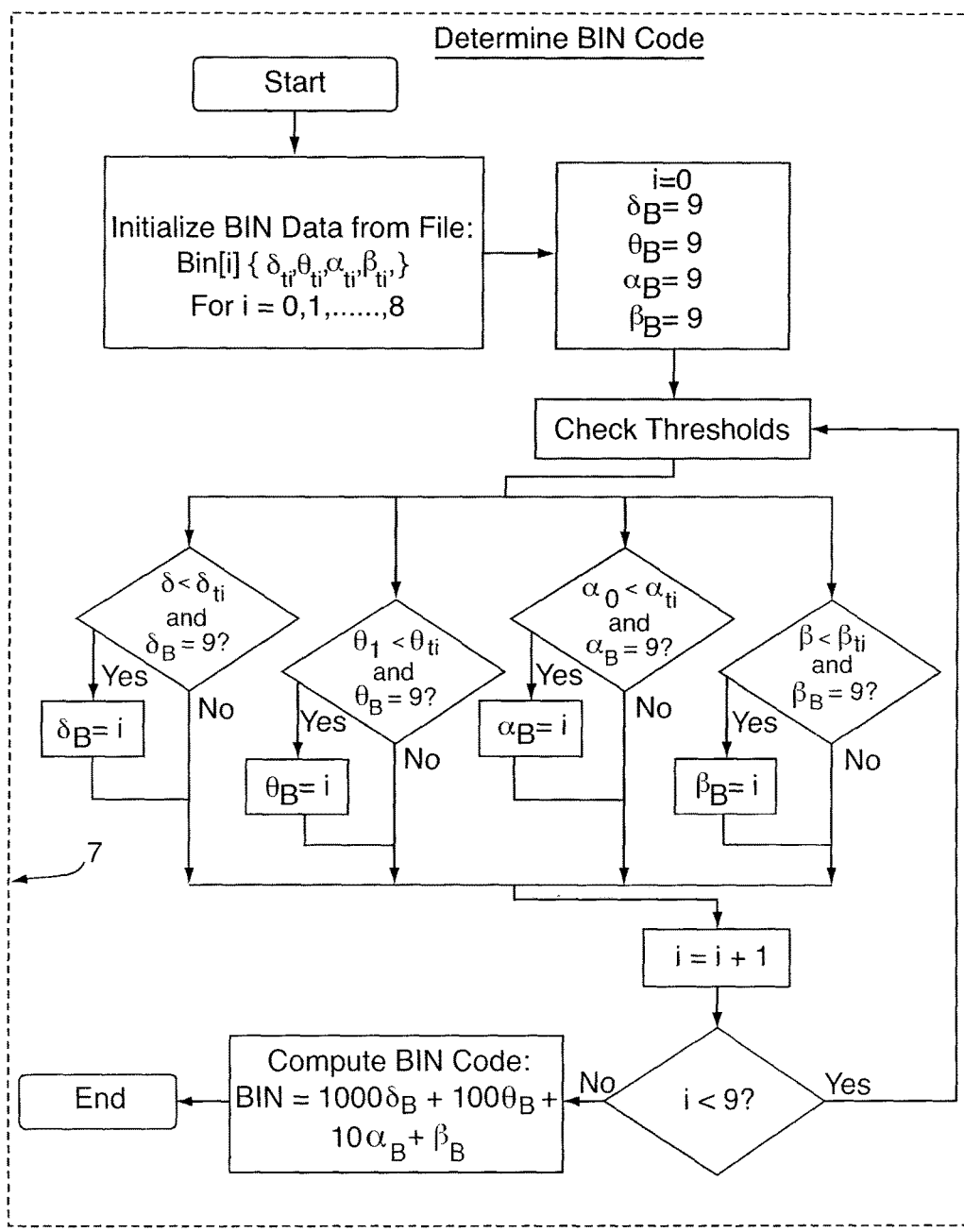
FIG. 6 is a block diagram showing the assign Bin Code.

FIG. 6 shows the approach used to assign Bin Codes (7). The algorithm checks the delta power in the 3-sec bin against the thresholds for the 10 ranks in the delta column of the stored Table 1 and assigns the appropriate rank to the delta power. The same process is repeated for theta, alpha/sigma and beta power, assigning a rank to each. Finally a 4-digit number is generated having the delta rank, followed by the theta rank, followed by the alpha/sigma rank and finally the beta rank. The process is repeated for each 3-sec bin.

Figure 7:
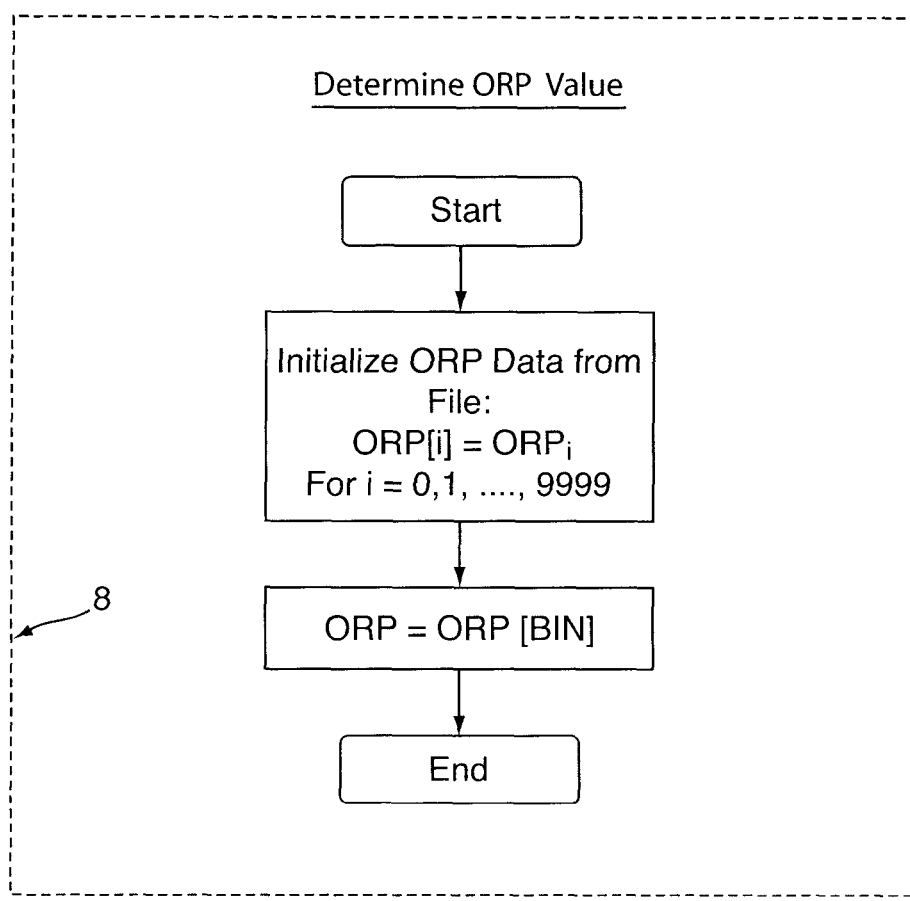
FIG. 7 is a flow chart showing the step of assigning the ORP values

FIG. 7 shows the step of assigning the ORP value (8). This simply consists of checking the ORP code in the ORP table and obtaining the ORP value associated with the code.

Figure 8A:
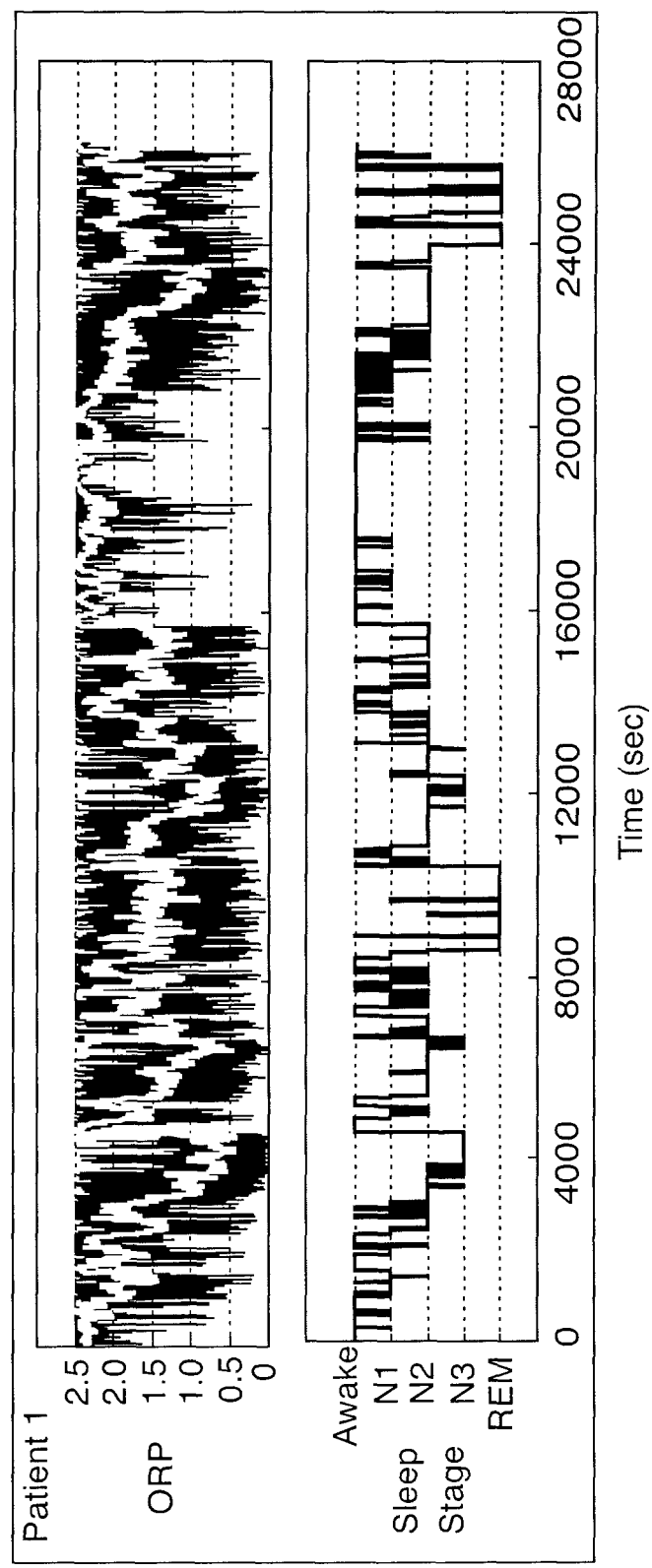
FIGS. 8a-b shows the typical results of ORP values over several hours of recording for two patients with the results of conventional sleep scoring into five stages (awake, N1, N2, N3, REM)
Figure 8B:
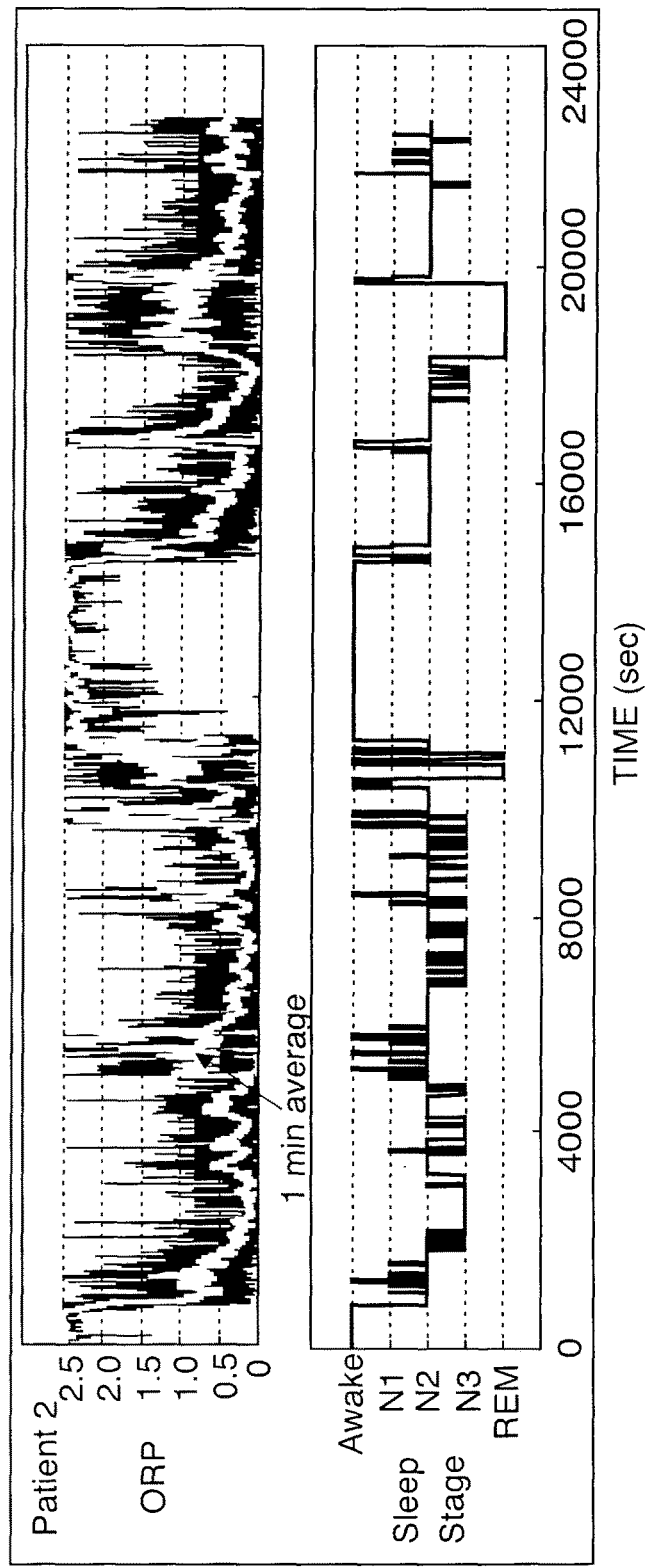

FIG. 8 shows results of ORP values (generated according to the preferred embodiment) over several hours of recording in two patients along with the results of conventional sleep scoring into five stages (awake, N1, N2, N3, REM). By conventional criteria, the main difference between the two patients was a somewhat greater awake time in patient 1 (Table 3 below). However, by looking at the ORP values in FIG. 8, it is clear that even when patient 1 was technically staged asleep, the ORP was highly unstable, reflecting extensive and frequent intrusion of awake features within the EEG, and that the average ORP (white line within the ORP panel) was substantially higher inpatient 1 than in patient 2 for all sleep stages (see also Table 3). Thus, not only was there more awake time in patient 1 but, when he slept, his sleep quality was quite poor. FIG. 8 also shows that during awake periods in both patients ORP was not fixed at 2.5 (the highest level) but there were frequent decreases in ORP, reflecting intrusion of sleep features during awake time. Thus, the awake state is not a constant but incorporates different levels of vigilance that can be reflected by the ORP value.

TABLE 3

|  | Patient 1 | | Patient 2 | |
| --- | --- | --- | --- | --- |
|  | Time (min) | ORP | Time (min) | ORP |
| Awake | 155 | 2.28 | 85 | 2.28 |
| N1 | 59 | 1.84 | 16 | 0.86 |
| N2 | 147 | 1.39 | 195 | 0.42 |
| N3 | 24 | 0.72 | 55 | 0.18 |
| REM | 52 | 1.59 | 29 | 1.00 |
| Total Sleep | 282 | 1.46 | 294 | 0.45 |
| Total Recording Time | 436 | 1.75 | 378 | 0.86 |

2) Generation of the Probability Index from Streaming Data (i.e. in Real Time):

The same procedure, with minor modifications, is used to generate the probability index on a continuous basis by analyzing short segments of recording and outputting the result as the data flows in. It is particularly suited for applications that require rapid feedback about the patient's sleep state or state of vigilance. It can also be utilized as a preliminary step in other software that performs simultaneous scoring of sleep stages concurrently with data acquisition. This application can be implemented on standard desktop computers, laptops or other mobile computing devices depending on the clinical indication. With all such devices the EEG output of the data acquisition system is channeled to the computer via a USB port or other suitable means. The data is then streamed into memory using existing or custom software.

Figure 9:
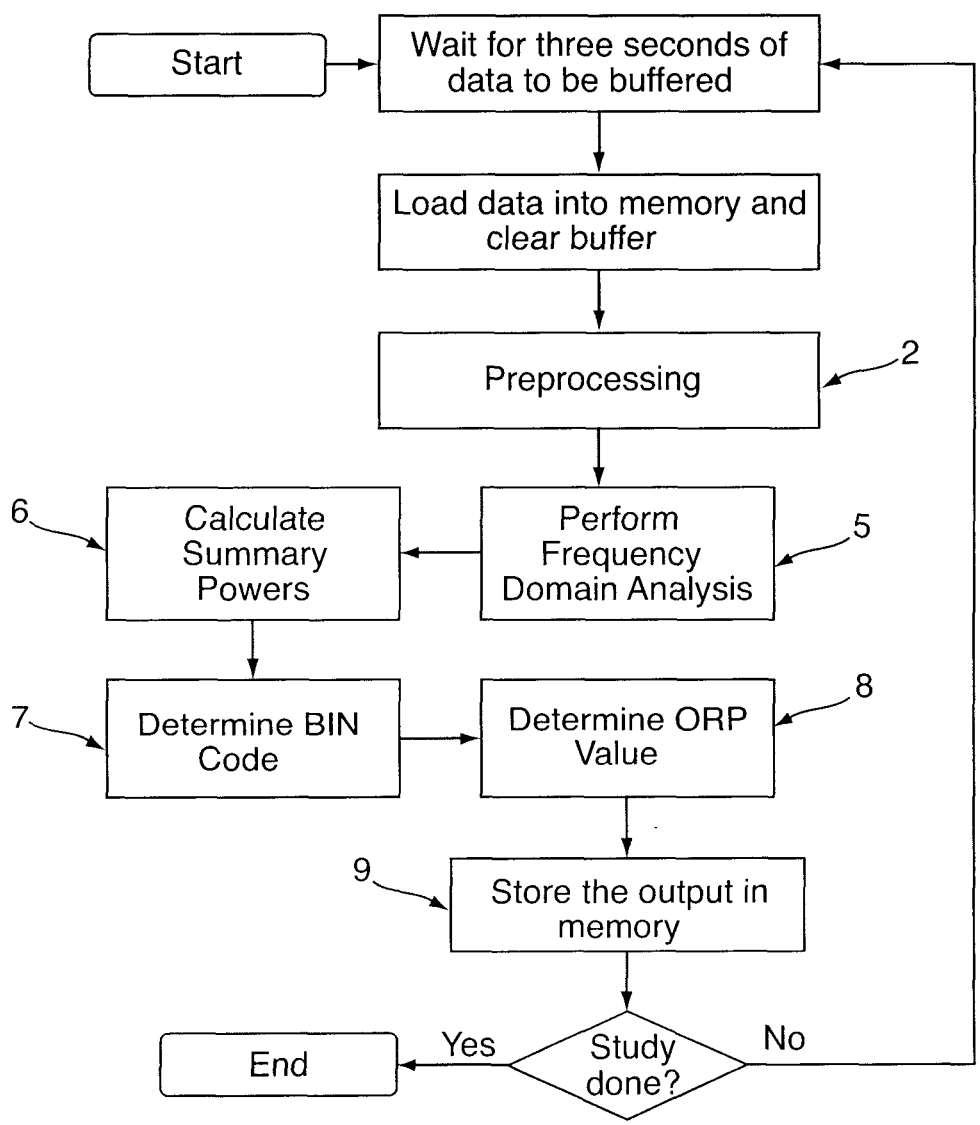
FIG. 9 is a flow chart showing the processing of streaming data for ORP determination.

FIG. 9 is a flow chart showing the processing of streaming data. Here, each specified interval (bin; for example 3 seconds) is treated as a separate file. When data for such interval has been received, the software goes through the same process described in FIGS. 1 to 7, including preprocessing (2, FIG. 2), frequency domain analysis (5, FIG. 4), Calculate Summary Powers (6, FIG. 5), Determine Bin Code (7, FIG. 6), and finally Determine ORP value (8, FIG. 7). A single ORP value is generated and displayed. The process repeats until the end of the study.

Figure 10:
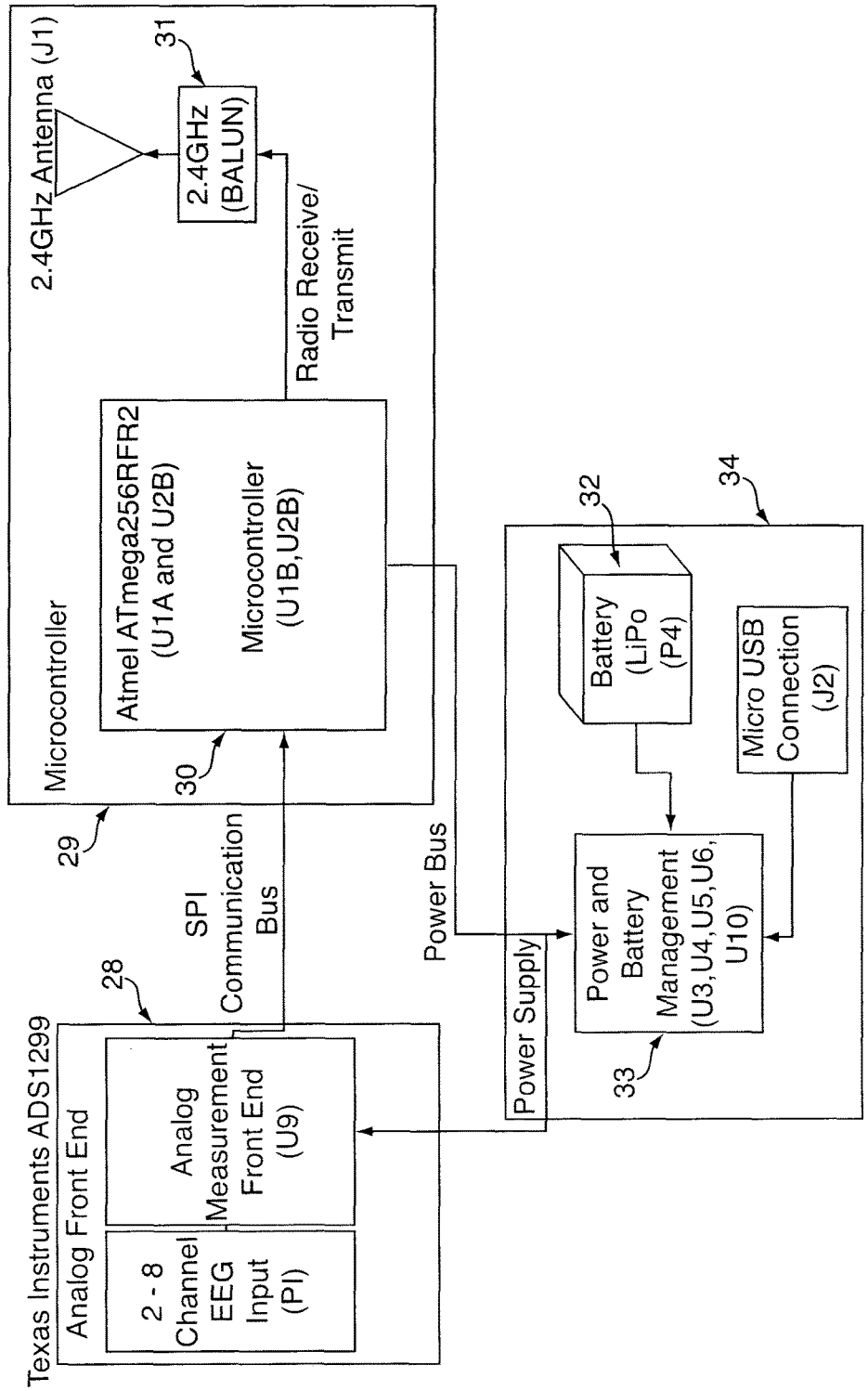
FIG. 10 is a block diagram of the components of a mobile device that implements the present invention.

FIG. 10 is a block diagram of the components of a mobile device that implements the present invention. A data acquisition chip (Texas Instruments ADS1299; 28) is used for collecting up to eight channels, any of which can be an EEG channel. The output is conveyed, via an SPI communication Bus, to a micro-controller (29) that incorporates Atmel ATmega256RFR2 (U1A and U2B) microcontroller (30) and a radio receiver/transmitter (BALUN; 31). The system is powered by a Lithium ion battery (32) with associated battery and power management circuitry (33).

Figure 11B:
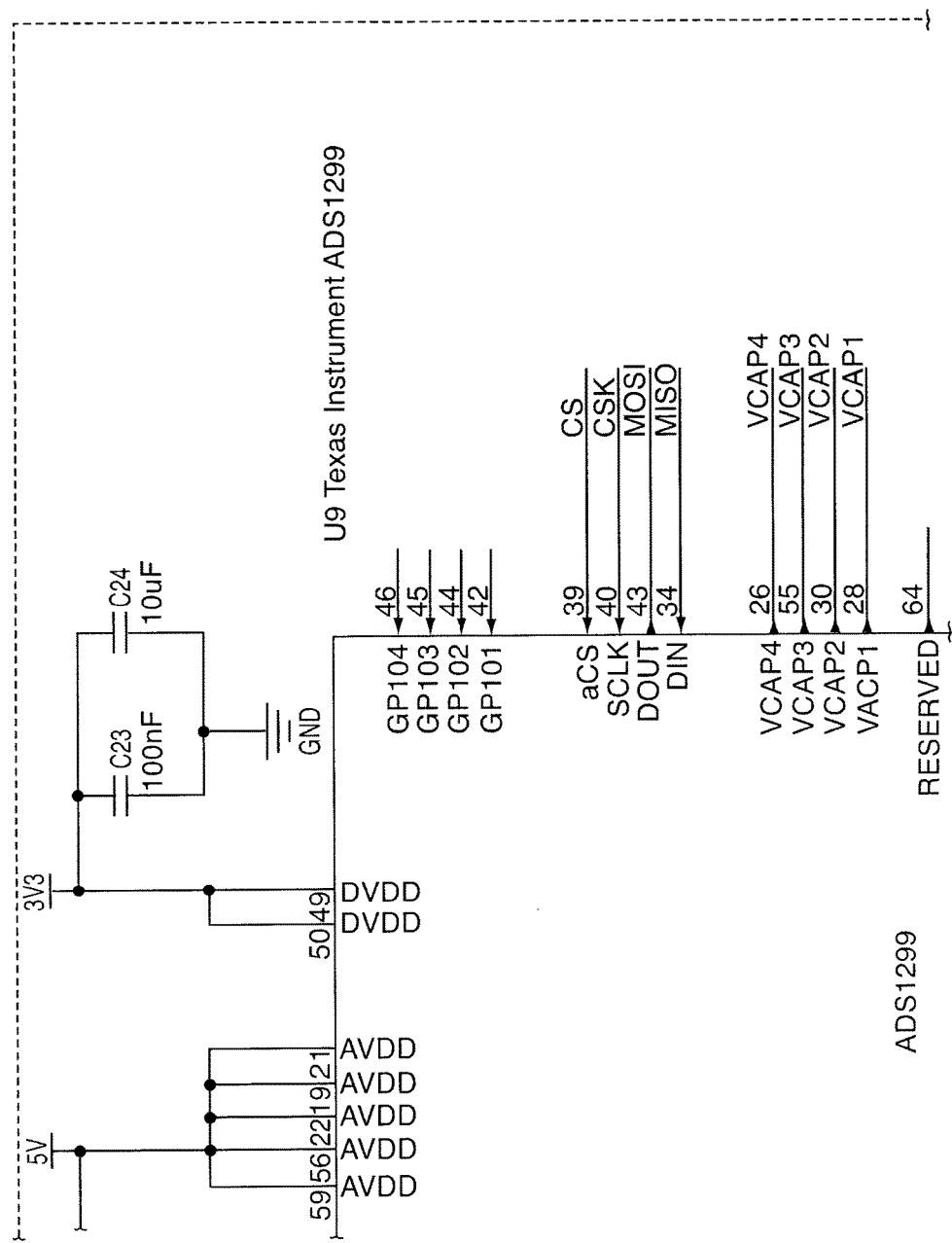
Figure 11C:
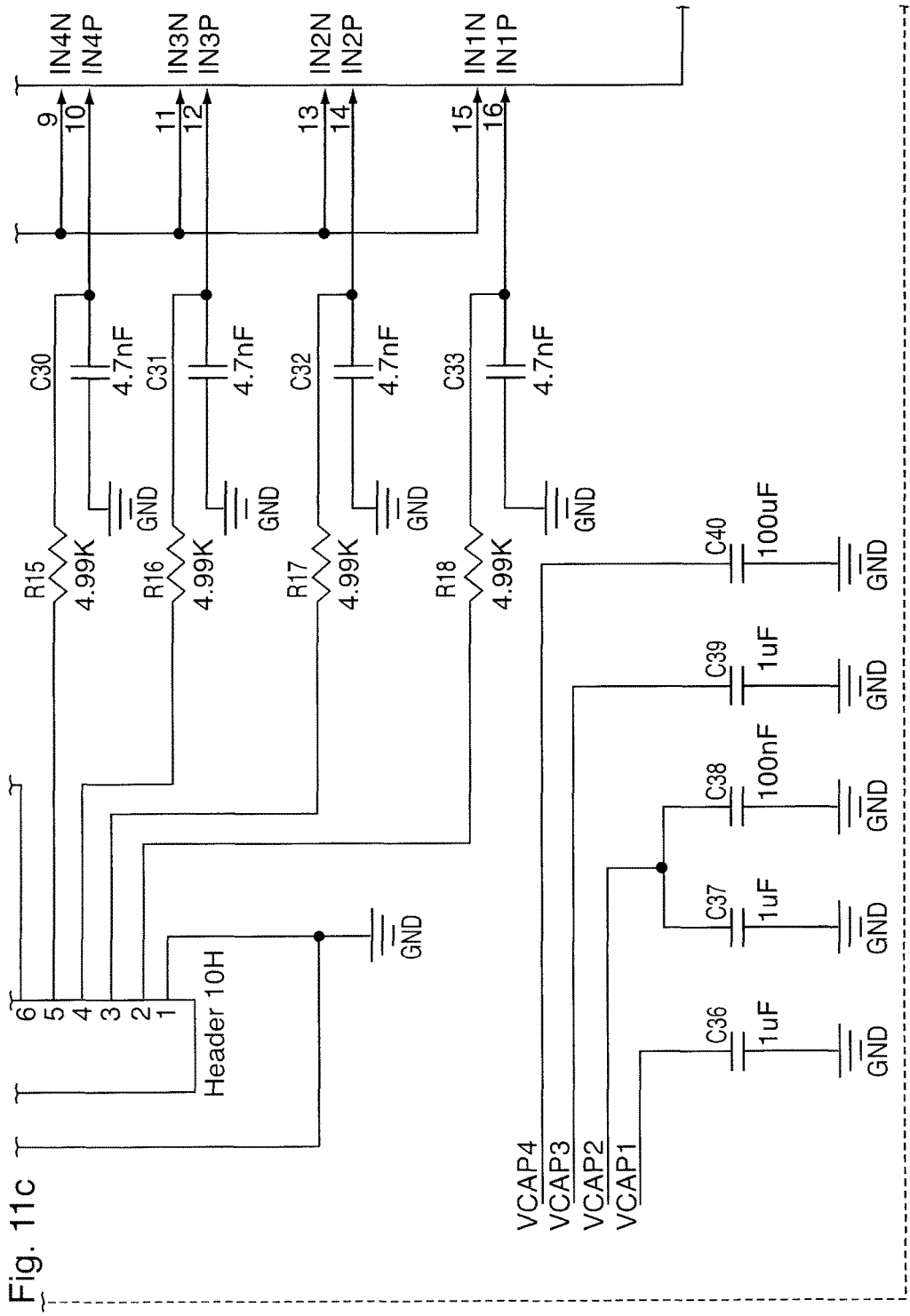
Figure 11D:
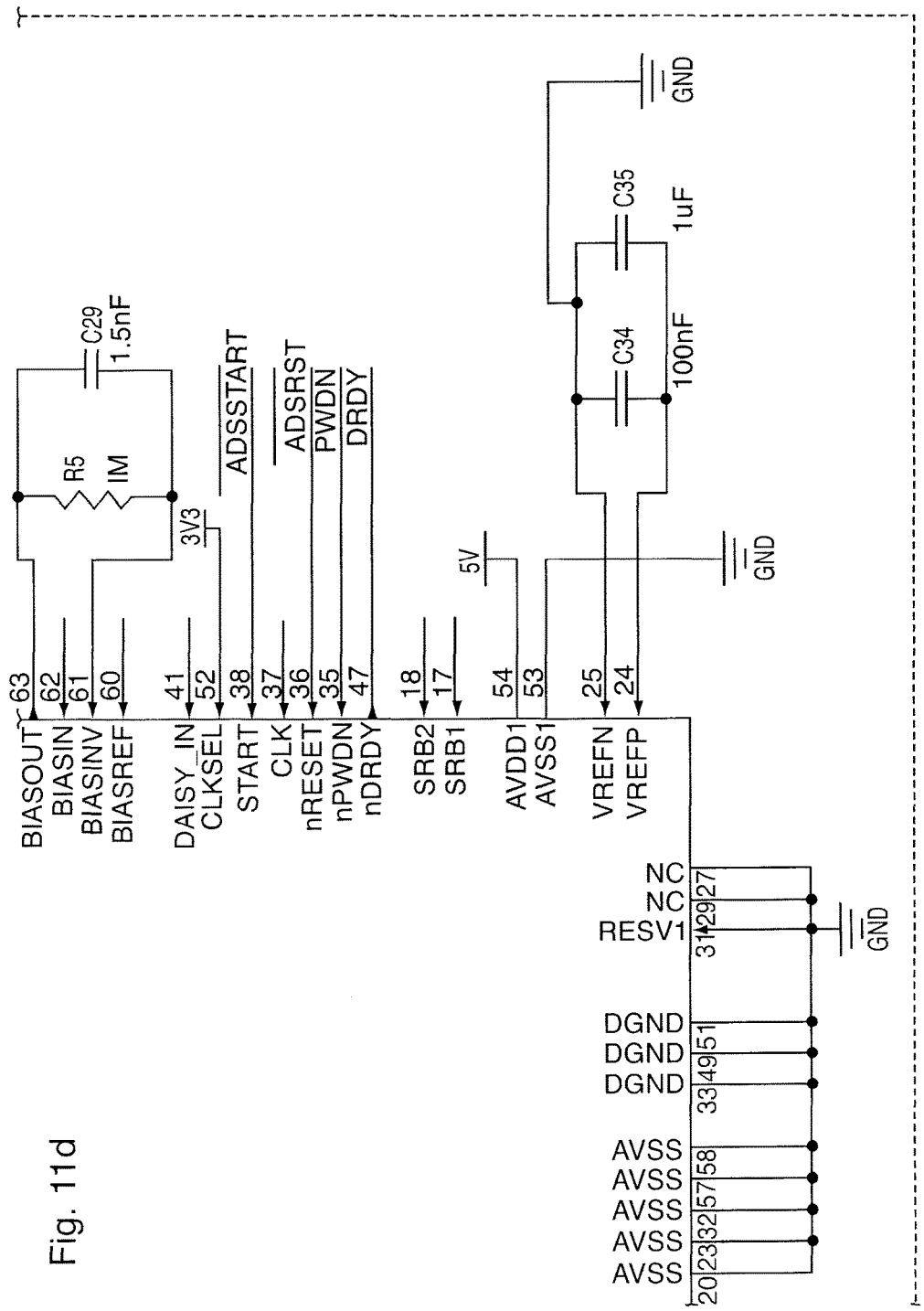
Figure 12A:
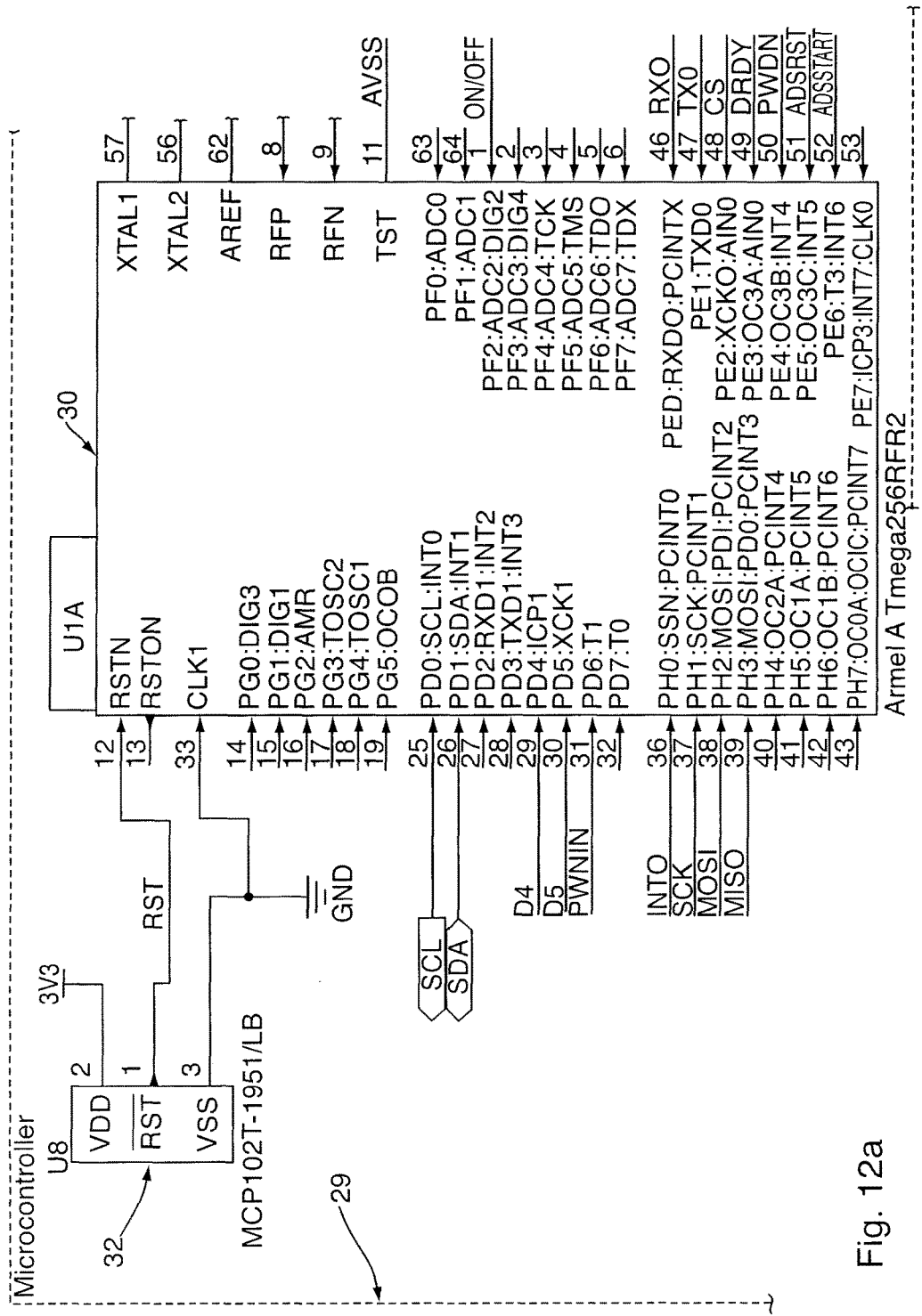
FIGS. 12a-c shows details of the micro-controller and associated circuitry of the instrument of FIG. 10.
Figure 12B:
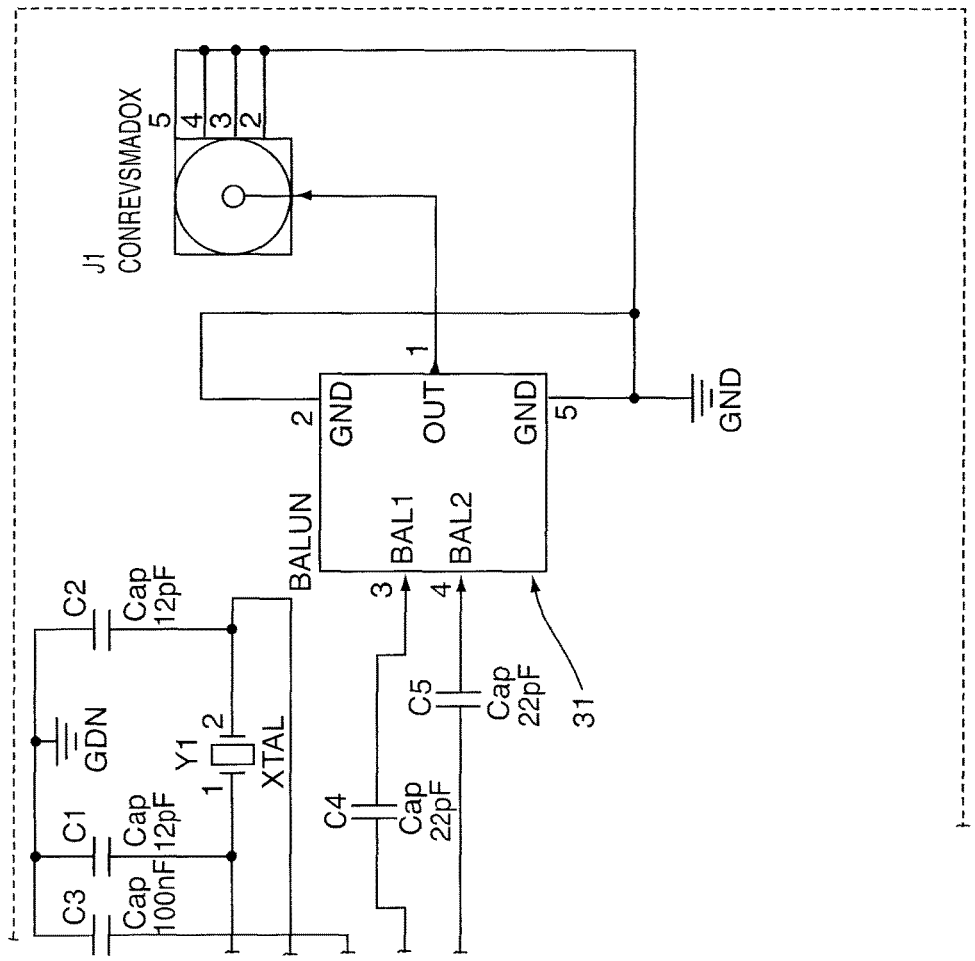
Figure 12C:
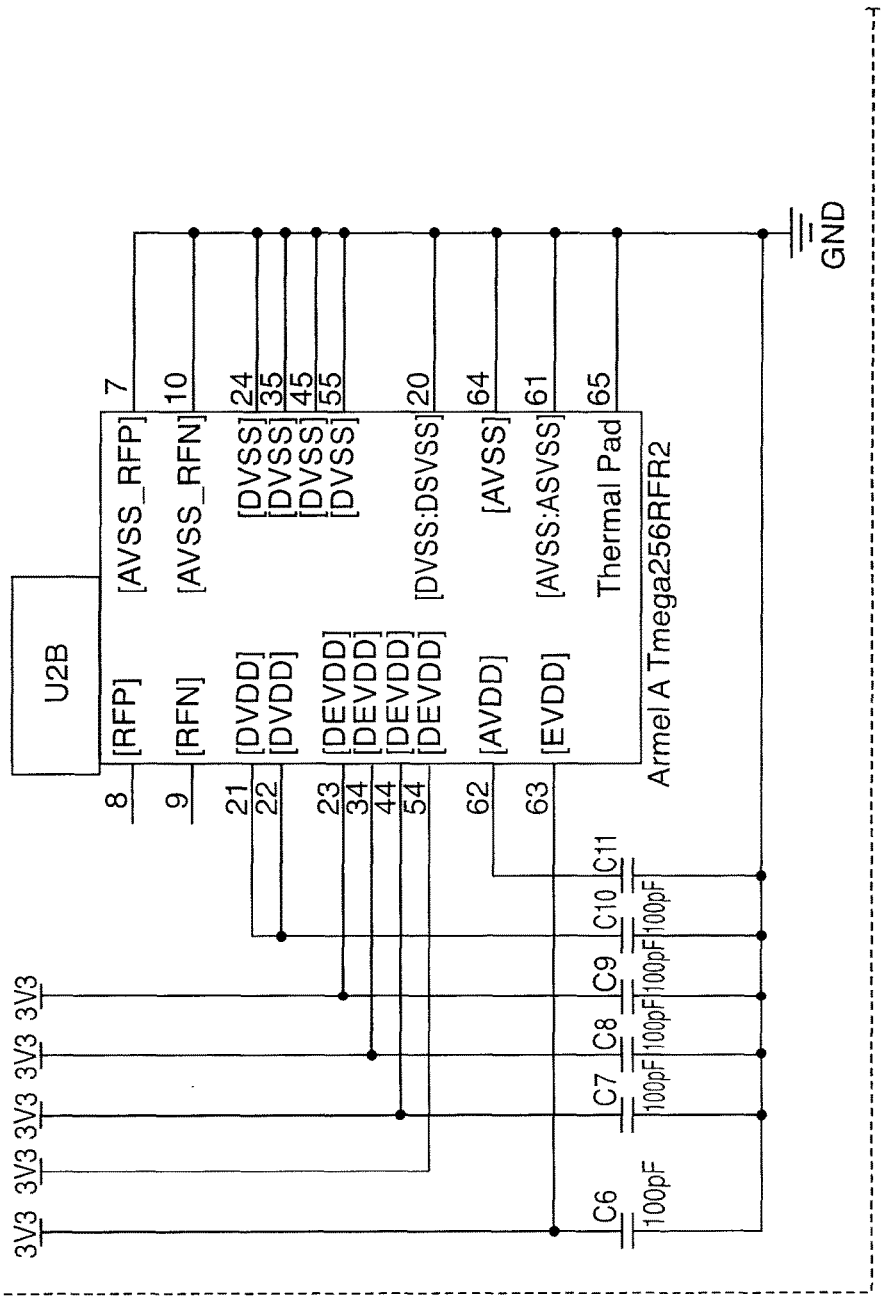
Figure 13B:
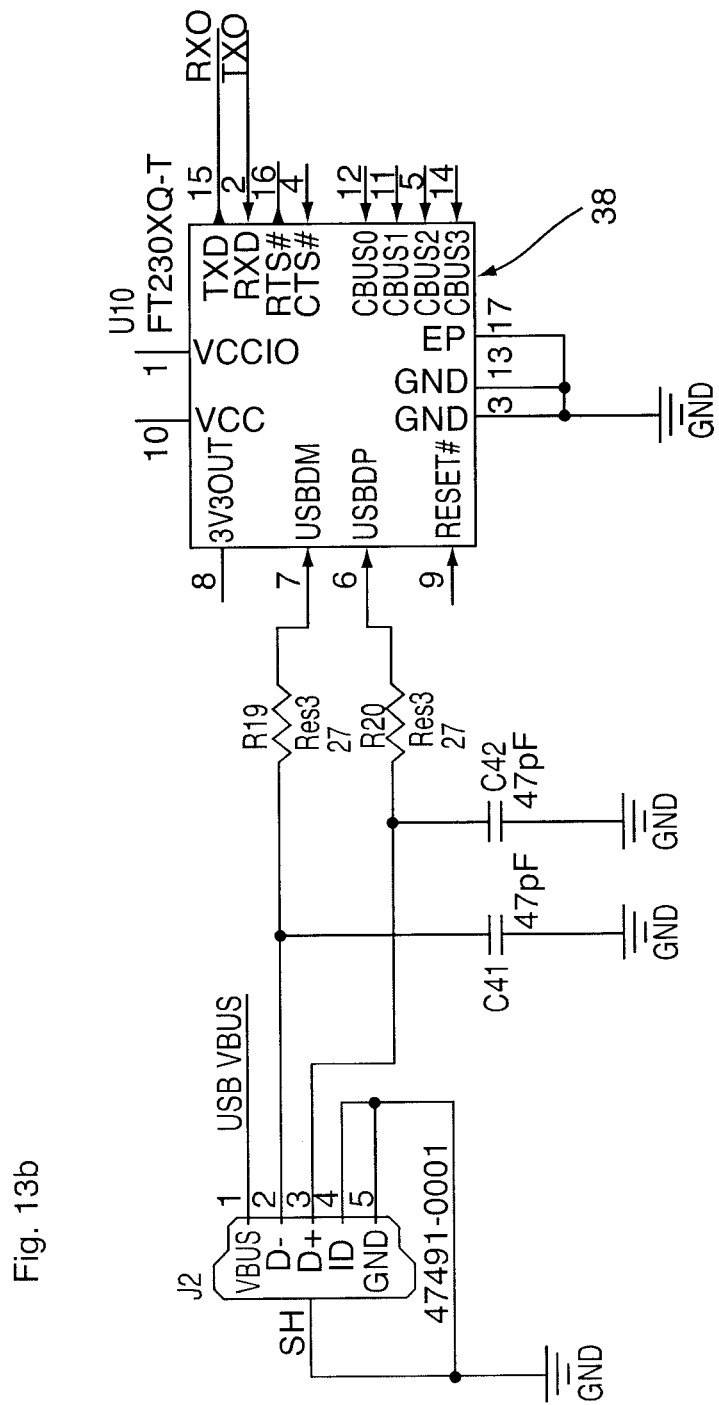
Figure 13C:
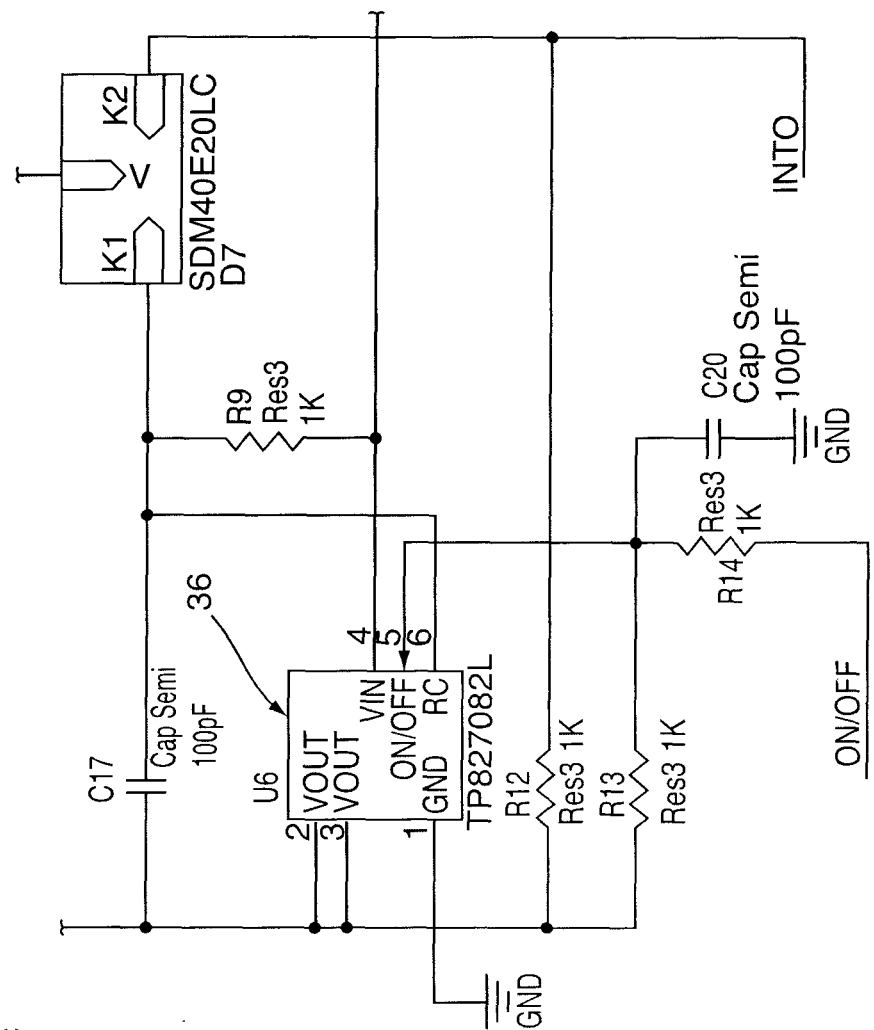
Figure 13D:
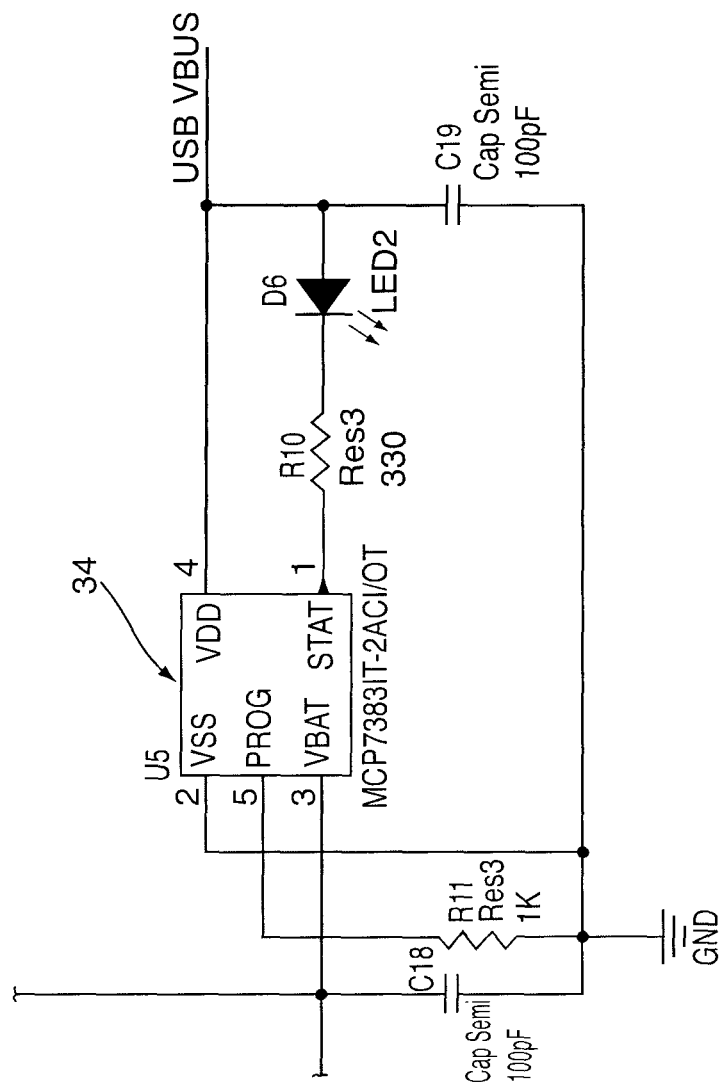

FIG. 11 shows details of the Front End Analog Circuitry (28) associated with Texas Instruments ADS1299 chip comprising:

Analog front end for biopotential measurements
Low noise delta sigma analog to digital converter
8 channels, simultaneous sampling
24-Bit analog precision
Sample rates from 250SPS (samples per second) to 16 kSPS FIG. 12 shows details of the micro-controller (29) and associated circuitry comprising:

Atmel ATmega256RFR2 (U1A and U2B)(30) with:
8-bit Microcontroller at 16 MHz
256 KB Flash Memory
32 KB Program RAM (random access memory)
Fully integrated RF Transceiver for the 2.4 GHz ISM Band (industrial, scientific and medical)
RF Data rates from 250 kb/s up to 2 Mb/s
ZigBee and IEEE 802.15.4 RF compliant
Wurth Electronics—732-2230-1-ND (BALUN) (31)
BALUN—Balanced to unbalanced converter
blocks common mode waves and allows only differential mode waves to the antenna.
Microchip—MCP102T (32)
Micropower voltage supervisor
Prevents unnecessary microcontroller resets due to brown out conditions FIG. 13 shows details of the power supply (33) and associated circuitry comprising:

Lithium ion battery (32)
Microchip—MCP73831T (34)
Li-Polymer Charge Management Controller
Employs battery charging algorithms and measurement logic
Maxim Integrated—MAX1704 (35)
Battery fuel gauge and low battery alert
Provides battery data to the microcontroller
Alerts the microcontroller in case of low battery percentage Texas Instruments—TPS27082L (36)
PFET Load Switch
Provides Fast Transient Isolation and Hysteretic control
Linear—LT3971-3.3 (37)
38V, 1.2 A, 2 MHz Step Down Regulator
Switching power supply for the system
Converts battery power to 3.3V for microntroller and analog front end power supply
FTDI—FT230XQ (38)
USB to UART (serial) converter
Allows for data transfer between computer and onboard micro-controller.

SYSTEM OVERVIEW

Power is applied to system
Microcontroller enters bootloader which loads the firmware
Firmware initializes all system settings to allow for operation between the ADS1299 and itself
Firmware initializes radio connection between receiver and itself
START command issued to ADS1299 to start sampling 2 to 8 channels
Analog signal is converted to digital via the ADS1299
Digital data is sent over a serial protocol interface (SPI) to the microcontroller
This process repeats until a STOP command is issued
Appropriate signal conditioning and data analysis: As per steps 2, 5, 6, 7, and 8 (FIGS. 2, 4, 5, 6, and 7)
Algorithm output is sent over a wireless radio link

SUMMARY OF DISCLOSURE

In summary of this disclosure, the present invention provides a method of generating a probability index that reflects where an electroencephalogram (EEG) pattern lies within the spectrum of wakefulness to deep sleep, which employs a computer/microprocessor that performs the steps of method. Modifications are possible within the scope of the invention.

The invention claimed is:

1. A method for determining the probability of an electroencephalogram (EEG) pattern within an EEG test record of a subject having occurred in sections of reference EEG records scored previously as awake or EEG arousals, said method employing a computer/microprocessor that:
performs frequency domain analysis of one or more discrete sections of the EEG test record to determine EEG test record power at specified frequencies,
calculates EEG test record power over specified frequency-bands,
assigns, for each specified frequency band, a rank to the calculated power-in each discrete section of the specified frequency band, each rank being determined based on values of power encountered in a plurality of the previously scored reference EEG records,
assigns a code to each discrete section that reflects the ranking of the calculated powers in different frequency bands,
incorporates a database/lookup table constructed from previously scored reference EEG records that indicates the probability of each code to occur in sections of said reference EEG records scored previously as awake or EEG arousals,
determines, for each assigned code, the probability indicated in the database/lookup table that corresponds to the assigned code, and
reports the determined probabilities that reflect the probability of the electroencephalogram (EEG) pattern within the EEG test record of the subject having occurred in sections of reference EEG records scored previously as awake or EEG arousals.

2. The method of claim 1 wherein probabilities of codes assigned to more than one discrete section are averaged over specified intervals.

3. The method of claim 1 further comprising using the reported probabilities as a component of another system that determines stages of sleep, respiratory events, arousals, cardiac arrhythmias, or motor events during sleep.

4. The method of claim 1 further comprising outputting the probabilities after the EEG test record has been analyzed.

5. The method of claim 4 wherein the probabilities are outputted in real time as streaming data and loaded in computer memory.

6. A non-transitory computer readable medium embodying program code that when executed by a computer or microprocessor, performs the operations of:
performs frequency domain analysis of one or more discrete sections of the EEG test record to determine EEG test record power at specified frequencies,
calculates EEG test record power over specified frequency bands,
assigns, for each specified frequency band, a rank to the calculated power in each discrete section of the specified frequency band, each rank being determined based on values of power encountered in a plurality of the previously scored reference EEG records,
assigns a code to each discrete section that reflects the ranking of the calculated powers in different frequency bands,
determines, for each assigned code, a probability indicated in a database/lookup table that corresponds to the assigned code, the database/lookup table being constructed from previously scored reference EEG records that indicates the probability of each code to occur in sections of said reference EEG records scored previously as awake or EEG arousals, and
reports the determined probabilities that reflect the probability of the electroencephalogram (EEG) pattern within the EEG test record of the subject having occurred in sections of reference EEG records scored previously as awake or EEG arousals.

7. The non-transitory computer readable medium of claim 6 wherein the operations further comprise averaging probabilities of codes assigned to more than one discrete section over specified intervals.

8. The non-transitory computer readable medium claim 6 wherein the operations further comprise using the determined probabilities as a component of another system that determines stages of sleep, respiratory events, arousals, cardiac arrhythmias, or motor events during sleep.

9. The non-transitory computer readable medium of claim 6 wherein the operations further comprise outputting the determined probabilities after the EEG test record has been analyzed.

10. An apparatus comprising:
memory embodying computer executable code; and
a microprocessor configured to communicate with said memory and to execute said code to cause said apparatus to:

perform frequency domain analysis of one or more discrete sections of an EEG test record of a subject to determine EEG test record power at specified frequencies, calculate EEG test record power over specified frequency bands, assign, for each specified frequency band, a rank to the calculated power in each discrete section of the specified frequency band, each rank being determined based on values of power encountered in a plurality of reference EEG records scored previously as awake or EEG arousals, assign a code to each discrete section that reflects the ranking of the calculated powers in different frequency bands, determine, for each assigned code, a probability indicated in a database/lookup table that corresponds to the assigned code, the database/lookup table being constructed from previously scored reference EEG records that indicates the probability of each code to occur in sections of said reference EEG records scored previously as awake or EEG arousals, and report the determined probabilities that reflect the probability of an electroencephalogram (EEG) pattern within the EEG test record of the subject having occurred in sections of reference EEG records scored previously as awake or EEG arousals.

11. The apparatus of claim 10 wherein the apparatus is further caused to average probabilities of codes assigned to more than one discrete section over specified intervals.

12. The apparatus of claim 10 wherein the apparatus is further caused to use the determined probabilities as a component of another system that determines stages of sleep, respiratory events, arousals, cardiac arrhythmias, or motor events during sleep.

13. The apparatus of claim 10 wherein the apparatus is further caused to output the determined probabilities after the EEG test record has been analyzed.

14. The apparatus of claim 13 wherein the determined probabilities are outputted in real time as streaming data.

15. The apparatus of claim 10 wherein said apparatus is a portable device that measures EEG activity of the subject.

* * * * *